United States Patent
Novick et al.

(10) Patent No.: US 11,149,269 B2
(45) Date of Patent: Oct. 19, 2021

(54) COMPOSITIONS AND METHODS FOR NON-ANTIBIOTIC TREATING OF BACTERIAL INFECTIONS BY BLOCKING OR DISRUPTING BACTERIAL GENES INVOLVED IN VIRULENCE OR VIABILITY

(71) Applicant: New York University, New York, NY (US)

(72) Inventors: Richard Novick, Bayside, NY (US); Hope Forer Ross, New York, NY (US); Geeta Ram, Woodside, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 16/613,322

(22) PCT Filed: May 15, 2018

(86) PCT No.: PCT/US2018/032754
§ 371 (c)(1),
(2) Date: Nov. 13, 2019

(87) PCT Pub. No.: WO2018/213301
PCT Pub. Date: Nov. 22, 2018

(65) Prior Publication Data
US 2020/0199570 A1 Jun. 25, 2020

Related U.S. Application Data

(60) Provisional application No. 62/506,546, filed on May 15, 2017, provisional application No. 62/543,343, filed on Aug. 9, 2017.

(51) Int. Cl.
| | |
|---|---|
| *C12N 15/09* | (2006.01) |
| *C12N 15/10* | (2006.01) |
| *A61K 31/7105* | (2006.01) |
| *A61K 31/711* | (2006.01) |
| *C12N 9/22* | (2006.01) |
| *C12N 15/113* | (2010.01) |

(52) U.S. Cl.
CPC .......... *C12N 15/102* (2013.01); *A61K 31/711* (2013.01); *A61K 31/7105* (2013.01); *C12N 9/22* (2013.01); *C12N 15/113* (2013.01); *C12N 2310/11* (2013.01); *C12N 2310/20* (2017.05); *C12N 2320/32* (2013.01); *C12Y 304/24075* (2013.01)

(58) Field of Classification Search
CPC ...... C12N 15/102; C12N 9/22; C12N 15/113; C12N 2310/20; C12N 2310/11; C12N 2320/32; A61K 31/7105; A61K 31/711; C12Y 304/24075
See application file for complete search history.

(56) References Cited

FOREIGN PATENT DOCUMENTS

| | | |
|---|---|---|
| WO | 2014/124226 A1 | 8/2014 |
| WO | 2014/160418 A2 | 10/2014 |

OTHER PUBLICATIONS

Ram et al. (Nature Biotech. (2018); vol. 36, pp. 971-976). (Year: 2018).*
Vipra, A.A., et al., Antistaphylococcal activity of bacteriophage derived chimeric protein P128, BMC Mirobiology, Mar. 11, 2012, vol. 12, No. 41, pp. 1-9.
Damle, P.K., et al., The roles of SaPI1 proteins gp7 (CpmA) and gp6 (CpmB) in capsid size determination and helper phage interference, Virology, Jun. 17, 2012, vol. 432, No. 2, pp. 277-282.
Chen, J., et al., Pathogenicity Island-Directed Transfer of Unlinked Chromosomal Virulence Genes, Molecular Cell, Dec. 11, 2014, vol. 57, No. 1, pp. 138-149.
Verco, R.B., et al., Cylotoxic Chromosomal Targeting by CRISPR/Cas Systems Can Reshape Bacterial Genomes and Expel or Remodel Pathogenicity Islands, PLoS Genetics, Apr. 18, 2013, vol. 9, No. 4, e1003454, pp. 1-13.
Santiago, M., et al., A new platform for ultra-high density *Staphylococcus aureus* transposon libraries, BMC Genomics, Mar. 29, 2015, vol. 16, No. 252, pp. 1-18.
Kim, W., et al., Identification of an Antimicrobial Agent Effective against Methicillin-Resistant *Staphylococcus aureus* Persisters Using a Fluorescence-Based Screening Strategy, PLoS One, Jun. 3, 2015, vol. 10, No. 6, e0127640, pp. 1-15.
Park, J.Y., et al., Genetic engineering of a temperate phage-based delivery system for CRISPR/Cas9 antimicrobials agains *Staphylococcus aureus*, Scientific Reports, Mar. 21, 2017, vol. 21, No. 7, pp. 1-13.

* cited by examiner

*Primary Examiner* — J. E. Angell
(74) *Attorney, Agent, or Firm* — Hodgson Russ LLP

(57) ABSTRACT

Provided are modified *Staphylococcus aureus* pathogenicity islands of a variety of types and origins. The pathogenicity island are characterized as having a polynucleotide comprising a bacterial pathogenicity island nucleotide sequence (a "B-PINS") that contains one or more modifications ("modified B-PINS"), that include i) a deletion or disruption of at least one virulence determinant of the B-PINS; and ii) an insertion of at least one cargo sequence. The polynucleotide are capable of being packaged within a bacterium into a phage-like particle that comprises a bacteriophage capsid, tail and tail fiber proteins in the form of an antibacterial drone ("ABD"). The ABD is capable of infecting bacteria such that at least one cargo sequence is introduced into bacteria infected by the ABD. Pharmaceutical and other compositions the ABDs are also included. Bacteria that make the ABDs are provided, as are isolated and/or purified ABDs. Methods of killing or otherwise modifying bacteria using the ABDs are also provided.

15 Claims, 41 Drawing Sheets

Specification includes a Sequence Listing.

Figure 2  Packaging of phage and SaPI DNA

Figure 7
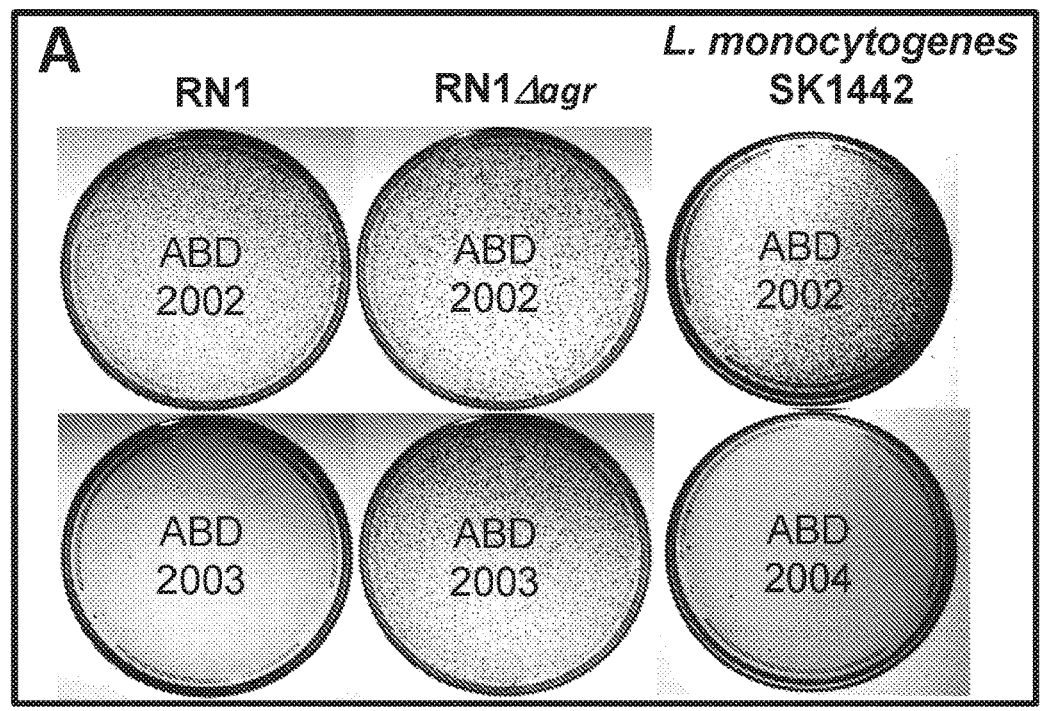
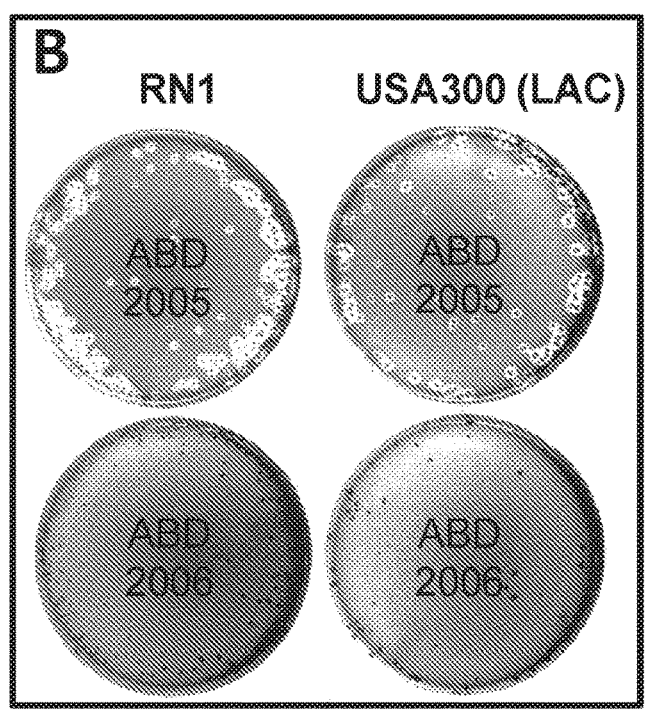

Figure 8
A
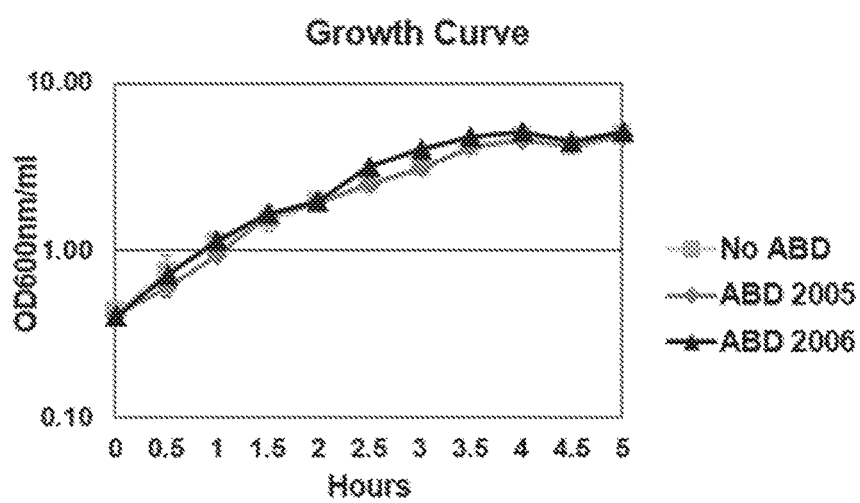
B
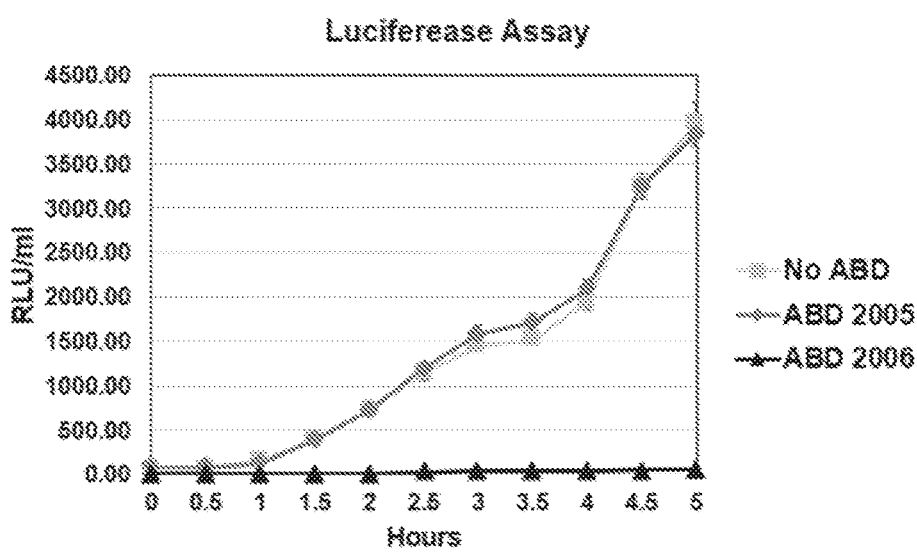

Figure 12
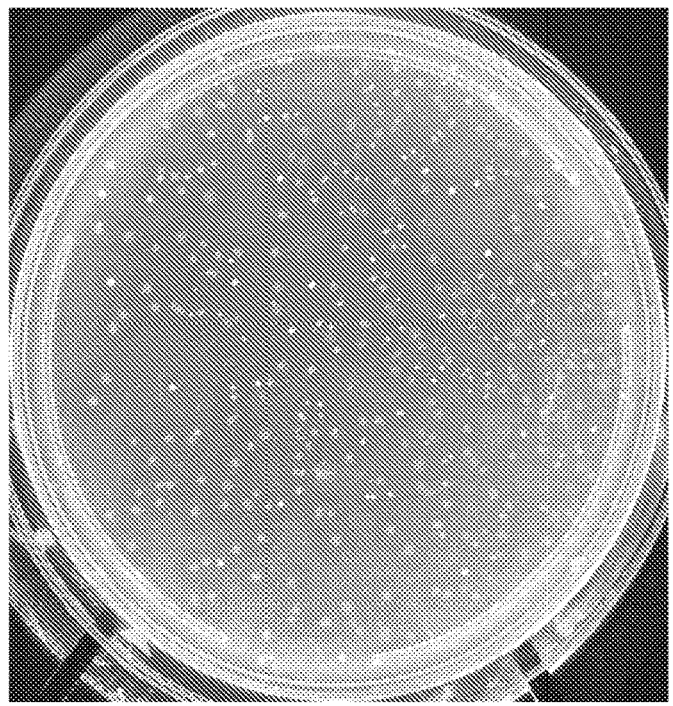
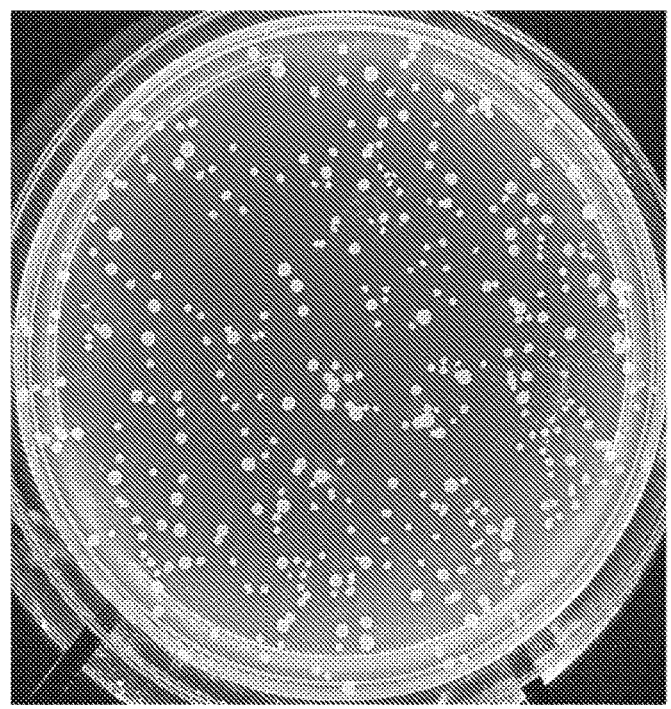

```
aaaagctaatgttgcaatcgagcgttcaggacttcagactctccac
catttcggttcttcaacgattgattcttaaaccagtgtagctgttttggtgat
ttcaagcgaggatgcatgcgttccgtgccgtcaggagtgtacgctgtacagatgaat
gagcagaattctcatgtgaattcgatgacaggagacgtgtcagctggcggccac
cttctctatgatcttgcaaatggttgaatccctgccggaagccctctcggaggcggatgga
cggttccttccaattgtacggatcattcaagagttctgtctaatcgcaatccaagcactct
tgccaccgctgaatgtcatttacctttaaatccggatcattcaaacaaagcgttctcattat
gacgcggagtgcctgattaccttcactactttcaagaaggcaacttggcaatgcctctcattat
gaggaccgatggccatggccttgaatcaaccagcatgccttttccatcgcgcgatttcattat
cttctcgccattaacccttaagctgtaagctgaatttgaattgtattttaagtcaaccgaaat
gcttggccaggccaagtcttttttataaaatgaaaggtgtactaaaggaggaaaac
acataaaaacagaactactgtttctccgcattcttcgccctctcagtgtcctcagtgattttaaggag
ttttggaaacggatttgaaattctccgcattctggatttcttctacagcaagcatagagaatcc
ttatcaagcgaagcaacactgtttaaggatttacacaagcaactcattttacacaagtagag
gccaggtcaatggccatggacctttatgaactcattttacacaggatcgcaacttgccgtagggc
tgccaccgttgccatcagcgattatcctaagactcaaagatcaagattgactctcaggaaa
tactcaacggacggaaattcgccatttactccaatttggctaaacaggctgatgactcaggaaa
aaacaaaagccgccgtaccttccctcaaagaattaacggatcacaccgagagaatgcc
tcaattctgaagagtttaaaggaattacagaagcttgcaagaaatcacgcaaatccctcatt
taagcaaggcggtcattgaatacagcggttgattttcaatagctgaagtcgatt
caccggacggaattggaagcctgtccctgatcatgccgtttgcgttggcttcggtcgaaaca
tagaaatgcaaggcaaaccgtatagaccgaagaaccgcagactgtaactttcctaaacca
atttgcatgcaagcccttcagtgccctagccttggtcgcgagccggtttcgagtcgacaga
acctgattgatccagccaagcccggagtaaccggaccggagattagccccaccatttaa
aatcgttaaccaagcggtagcaaccgccaactggccggatcacagacagactggatttaa
cgattgctcttatcattatcagattccaatgtaactaaacaccggattatcatcatcttggaa
gcacctggcctgcatcaagacaaataaaacaaaaagttgtacttttggactctgtgctgctt
atttcccaac
```

*com* sequences are black on a white background.
*rgg* sequences are white on a black background ccmA BSU31680 ccmA2 BSU31670

SEQ ID NO:1

CCCTCTAAATGAGCGAATAAGTCGAGATGATTATCCTAAATAATATACAAAGTATTAGCAATAAAATTGCCCATAAAG
TGGATGAAGGTTCATATCAGCCAAGTAGATAGAGTGTTTGCGTTATGCTCCAAGAAAAGGACACACATATTTATTAACGTGA
GTGAATGACTGCCCAATTATGATCGATATGTTGATATGCCTCGAACAGTGGTCGAAGGAGTTGAACAATCAAATGCTAGTCC
TAATGTCATAAGATACACTCGACGCGATAGTGAGTACTGGCGTGAGCTATGCTTTGAACAACTGAAGGAATGGTA
ACAATGCCACTAGCTAGCTTAATTGGGCATTTATTAAGATCCACGTTAATGATATATGTTTATTCATTGCTTTA
CTATGGGGCAATTCGCATGTAAACCACTATGAAAGAACAAGAAATCAACGCCACTTTCAATCGATATTAAATAA
ACACTATAACAATTAGAAAGGGCGTTTGTATGGAAACCAGTAAAAGTGATGTACTTTGATAAAATTGAAAAAATTAAT
AAAAAGATAGTGCCTTACAGAATTATACCAAAAGTTATGAATTGAACATCATCAATGGGTATTGCTTAAA
TCAACTTATACCAAGTAAAAAAGAAGCGAGCCAGTAAAAAAGTTTTATCACAAGTACAATCCTCAAATCACTG
AACGCTTTGAAGATATTGAGAGTAACGAGTCAGCTCAGTTTATATGCTTTTCTATGACAATAAAACCCAGTAAATATA
GCTGTGAGTGCCGAAGAAATTTCAGATAGTCGTCGTCAACTCTTGAAATTGGTTAATAAAAAGCTGATGTAAAGTGCAACGC
GACATCACTAAACTTGTTGATTATATTAATGCATCTAAACGGTATAATCCACCATTGAATGTTAAAGTTGCAACGC
GTTTGGGCAGTGTGAAAGTGAATTGATTTAATAGACTCTTTCAAAGCAAAGGAACATTGAGAGGTTACTCTAAAAGTGTT
AATGAAAAGGATTTCAAAGATTACCAATGGTAATGTTATATGCCCTCTTTATGTTGGTTTTATTAAGAGAATTG
CGGTCAAATAAAAGATTACCAATGGTAATGTTATATGCCCTCTTTATGTTGGTTTTATTAAGAGAATTG
GATTACAGCCCCTTTATTGTAGAAATACAGGTAGTACATCTACAGGTAAACATCACACTCAACTTAGTATCAAGT
GTTTGCGGAACGAGCGACCTTATCGACATGGAGTTCTACTCAAAATAGTATTGAATGCATGCATCATTTTGAA
CTCATTTCCAATGCGTTAAAGATGATACACGTTAATTAACACATAATCCTAAGTTGTTGTTGTTACCAGTGCCACATATAACTTCTA
GTGGTGAAAGTAAATCAAGAAGTAATAATCAAGAAGCGGGTAAAAAGAATGGCGAAATATTAATTTCT
ACTGGTGAATCATCTATCGCAAATAATTTTGATTTTGAATGCGTGATGAAAAAGCGGGTGTATCAGCACGTGTAGGTAGAGCTATCAAGATCC
ACCATATCCAGATAATTTTGATTTTGAATGCGTGATGAAAAAGCGGTATATCAGCACGTGTAGGTAGAGCTATCGTTAGGCGAACATCGTTAGGACGAACTATCGAACGGTATTAATCAAAA
TTATTAAACAATATGAGTCTAAAAAGTCTAAAAAAGTTTAGGAGAGCTATCAACGGTATTTAATCAAAA
GGTAGTAATGAAATCATGCAACATTGGAGGACGTGCGTTCCGTTACTACAAGTTACCGGTGAGTTTTGAATGATAT
TGATGGTTTGAACAATGACCATTTAAAATATCGAACAGCCTATGACACGTTAAAACAATAAGACGATTG
ATAAACTAAGCAACTCTTTAGAGGAACTATTACAATATTAGATGCAAATAGAAATAATATGCTGGTCATGGCTAT
AGTTCAGTCAAAAATGGTGACATCAAAGCTATATATAAACGTGATTATTTATGTATATTAGTGCAAACTGTACACGA
TAATTAGTCGATGAAATGCCAGACTATAACAGGTCAATGGGCAAAAAGGATATTTAATTAACAAACAAGGTGAAAAGATC
GCTTGCAAAAAGGTGAGTCACAAAAACATTAAGTATAGAGGATTGCTATAAACAAGAATAAGCTTGAAGAATTA
GGATTTGATTTCTCGAATTCTATAATGAAAACAATGTTCTTAGCTTTATACATATATGACTAGTTCCGAAGTTCCGCG
AAAACATACAAAGCGGAACTAAGACTATAAGTTAATTAAAGCAATTAAAGTAATAGTTCCGATAAGTTCCAATA
AATAATATTATTAATTGAACGGGAACTAAGTTTATTAATTGAAAGTTTATATATCAATGGTTTGACTAGTTCCGATAAGTTTAAC
GGTACAACGGGAACTAAGTTTATTAATTGAAAGTTTATATATCAATGGTTTGACTAGTTCCGATAAGTATTTAAGTCG

Figure 18, continued

GGAATCAACGGGGACTAGTTCCAATTAAAAATATTGGAGGTAACACATGGATAAAGAGCAACTAAAAGTATAT
ATACGATTATGTAAAGATAAGGAGATATCAGTTAGAAGATTTGTTAAAGAAATGAATGAACACT
ATATAGGAGAACCAGTGTCACACACGATAAGGATGAGAATATTGTGTTTGGAGTGGATGGAACAAAATTACAATG
TTTGCGCTGATTGAATTAGTTAAAAGTGAACAACTTGATTTAGTGTATAGAGATGACAACAAATATCGTTATTGTT
GGATGGTAGAGTTCCTACATTAGTAACTAATTGTTATCCAGAAGATGGACAACCAAATATCGTAAACCAATTCAAACAC
TGCCTATGGTATTAAGAATAAATAAAGAGGAGAAAATCAAATGACATAGAAACTATCGTAAACCATGTTGCTTAAGTATTAC
GAGCAGGCACGTTACTAAGTACTACACAGATTATTAGAACATAGTAAGTGCAACCATGTTGCTTAAGTTGTAAAGT
AATGATCCATTTGATAPGGCATACAGGTCACCTGATGATGGAAGTTATTCGGTCATGTATATATTTAAAGATTGTAAAGT
AAGGCAAATCATTTGAATTGGCGTAAACAGCTTTCTATTAGTGATATGATGGCCAGTCAATTATTTGAAGATGAGTATTTATG
TATGGATTACAAACATGCAGAATCAAATATGGCAGATTAGTGTGTTGAGTACCTAGAAAATGGATTTGATACCGATAC
ACTTGAGGGCATTCAATCGAGTAATACTGATCTGATGAGGGTTCAGATTAGTGTACAAGATGAGAATGCGACACAAGAG
ATGAACCAGACCAGATTAGTTGAGGGTTCAGATTAACTGAGTTGAAGTCATCTTATTACAGTTGAATAAGTAATAAAATATGGA
GATTACAAGGCTTTAGAGACATAAGTTCCTAATATATTAATAGATAGGTACGCAAATTCAAAAAGTCTGAAATGTTGATATT
GTCTCACGTGCTGTGTGGCTTGAAATTTGTGTTTTGTCATAGGTAAGTTAAGTTTGTGCAAGTTGTGAGAACTTGTAAC
GAGCTGTTTATGCTTGAAATTTGTGTTTTGTGCATAGGCCTAAAATTAAGTTTGTCGCTGTTGTTCGTAAAGTATA
GCTAATACAACCTAAAGTTTTAAATGTAAGTTGCAACATAGTGAGGTTATTTATCGAACTTAGTTCTATATTAGGTT
AGTATAGAGAGTTTAAAAGCCTAACGTTAAGTTTTATAAGTTTATAAGTGTTAAGGTAAAAATAAGCTATAACAATTGATAAA
AATGTGAAAAGCCTAACGTTAAGTTTTATAAGTTTATAAGTTGATAAGTGTTAACCTGTATAATTAGGTATGAAATAATTAAAGAAA
CGGGCTATAAGCGAACGAACGTTAGTCTGTTTTAGACCTGTAAAAATGGTATATAATTAGGTATGAAATAATTAAAGAAA
GAGGTGTAGAGAATGCAAAGTA*TCAA*TTAGCTAAGCAAACAGCATTATTAAATACGATTGCCTATCAAT
TCGGGTAGGCTCTGTTATAGGGGTGAATAAATAAGAAACTGCTAAAACGAAGAATTGTTTATATATTCGTAATGGCG
ACAATAAACTATCTGAGTATCAACTATTAACCCAGCATTTATTAATAAAAATTAGAGATGTGAA
TTCCAAATGAAAGTATGTACCACATGAGTGCGTCGACCACAACAAAGCAGGTTACAACAAGCAGGTTACAAAAACTATAAAGATAGATCTATA
ATATCCGATTGAAAAATTAGTTAPCAAATTATTGAAACAAAAGCAGGTTACAACAAGCAGGTTACAAACTATAAAAATAGATCTATA
ATAATATGGCGTTGTTGAAAAGCTACTAAAATCTAAAATCATTGAACGTCATTGAACGCTTACAAGTTGATTTGTATCAAGACTAAAAGTCATTCAACAACG
TCAAATGGACGATATAAGCCTTACAACGTCATTGAACGCTTACAACGTTGATTTGTATCAAGACTAAAAGTCATATAAACAACG
TTCAGAACGTCAAAAATGGTGTAACAATGGATAAAAGCCAATAAAAAGCAATAAAAAACGAATTCGTTTGTCATTAGTGATGAAAATTCTATGAATGGATG
CATATGTAAAAGTGGTGTAACAATGGATAAAAAGCCAATAAAAAACGAATTCGTTTGTCATTAGTGATGAAAATTCTATGAATGGATG
GTGATGTGTTGATAGATGATGAAATAATAACGGGAATAATCATTGATCATATTGTAAAGAATCATTGTTGACCAAGTGTAATGCAAGA
GCAGACGATAACATTGATGATCATATTGTAAAGAATCATTGTTGACCAAGTAGCAATGACAAGA

Figure 18, continued

GTTTTATATTTCGATTCTTTAATACAAGGAGTAGTTTTAAAGATATATTAGCAATGTCTTAGAGTGTTCAGAACAAT
CTGTAAGATTATGGTATGAAACCTTATTAGATATAAAATTGTGGAGGTGATAGAATGAGTGAGTTAACGGCAAAACAAG
CGCGTTTTGTGAATGAGTATATAAGAACACTTAATGTAACACAAAGTGCCATAAAAAGCAGGCTATAGCGCAAATAGT
GCACATGTGACAGGATGTAGTTTATTAAAGAAGCCACACATATATACAAGAACAAAAAGATAAGATTAT
AGATGAGAATGTATTAACGGCAAAAGAGTTACTACATGTCCTTACGAATGCGGCAGTCGGTGATGAGACAGAAACGA
AAGAAGTGTAGTGCAAGCGAGGGAATATAAAGAGAATCCACAAAGTGGCAAAGTACAGCTAGTCTATAACGAACAT
GTTGAACTGATAGAGGTACCAATAAACCTAGTGATCGTTTAAAAGCTCGTGATATGTGGGTAAATACCATAAGTT
ATTTACAGATAAGCATGATATATTAACGGGAATGTGCCTATATTCATTAATATTGGTGAATGGGATGGCGATGATGAAG
ATTTACAGATAAGACCGGTTACAAGCGTATCTAACGCTAAGAGGATTAGTTTACTAATTCACCCTAGCTTTATATTAA
GATTGATTACAGTAAAAACCATTATCATATTGAGTGAGTTAGTTTACTAATTCACCCTAGCTTTATATTAA
ACGTTATAAAGATAAAGGAGAACGCTTATTAATAACGACTCCCTTATTAATATGATTATTACAGAAAAAGT
GTAAAGTTAATGGATTAATATCATGTTTGTTTCGGGAAATATATGACGATGTTATACGTATTAATATATAATCAC
CAGTATAATACGTGATTACAACGTTGAATATAAAATATGACGATGTTATACGTATTAATATATAATCAC
AGTTGCAGGCATCAAACGCTTATTTATTAATCAAAAATGGGTGGACAAATTTATATAGTTTATCAATTTAATAT
TTTACACTAACTTATTATTAGGTGATATAAGATGCTGAGATAAGCATTATATTGCAATGAAAAGCATTATATGGATAA
TCATATATCTATCATTGCAAATATACTTATAGAGATTTATGTGTGTGATAATTGGTGGTCATAATTGGTCATAATGAA
ATAAAAAACTAAAAAAATTGAATGCATAAAGAATACCATGCTGATTTAATAGGATTTTGTATATGATTTATTAT
CTATTTCATACTGCCCTTAAATGCCAGGAATGCATGTAAAAT

SEQ ID NO:2

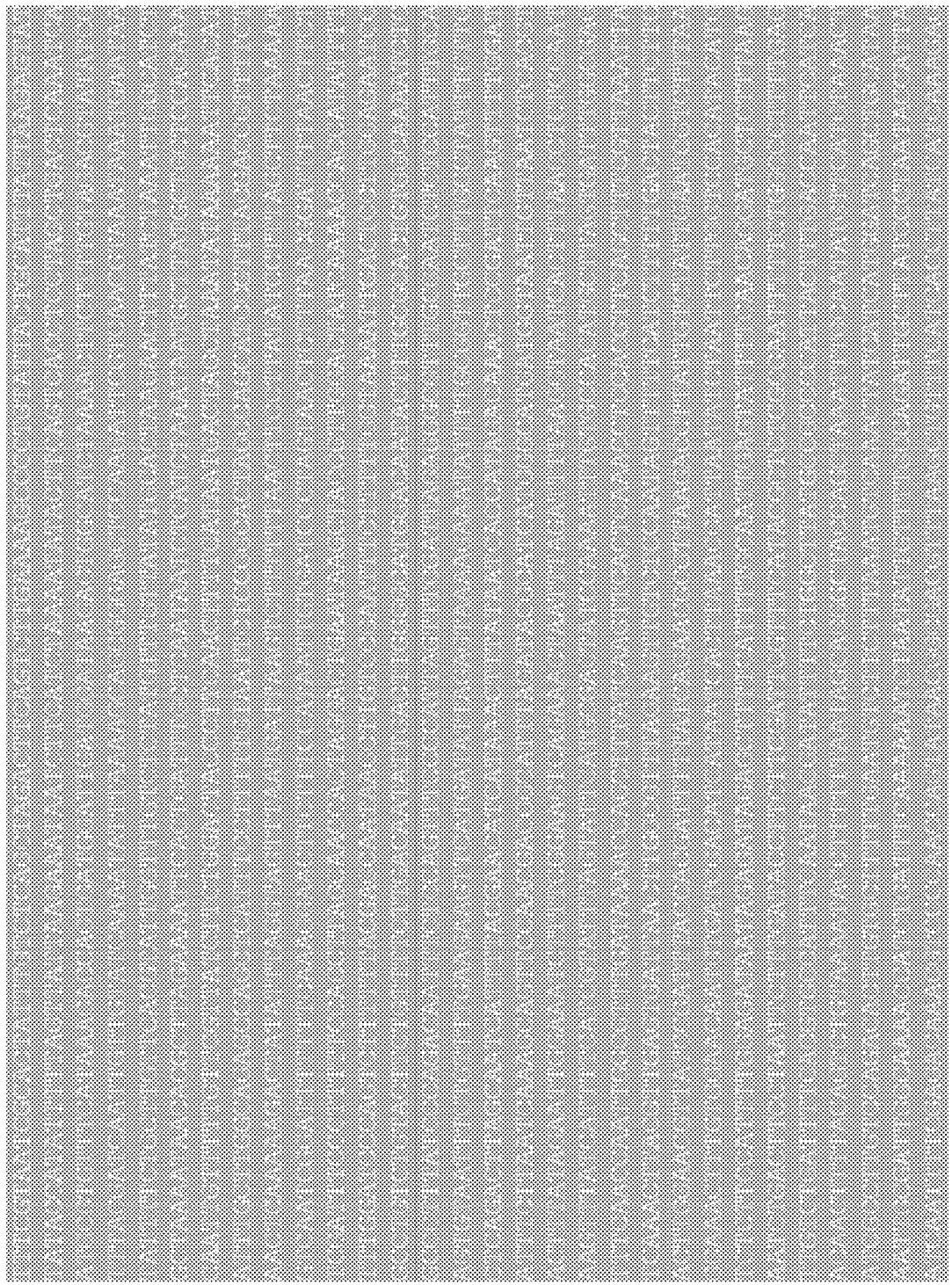
Figure 19, continued

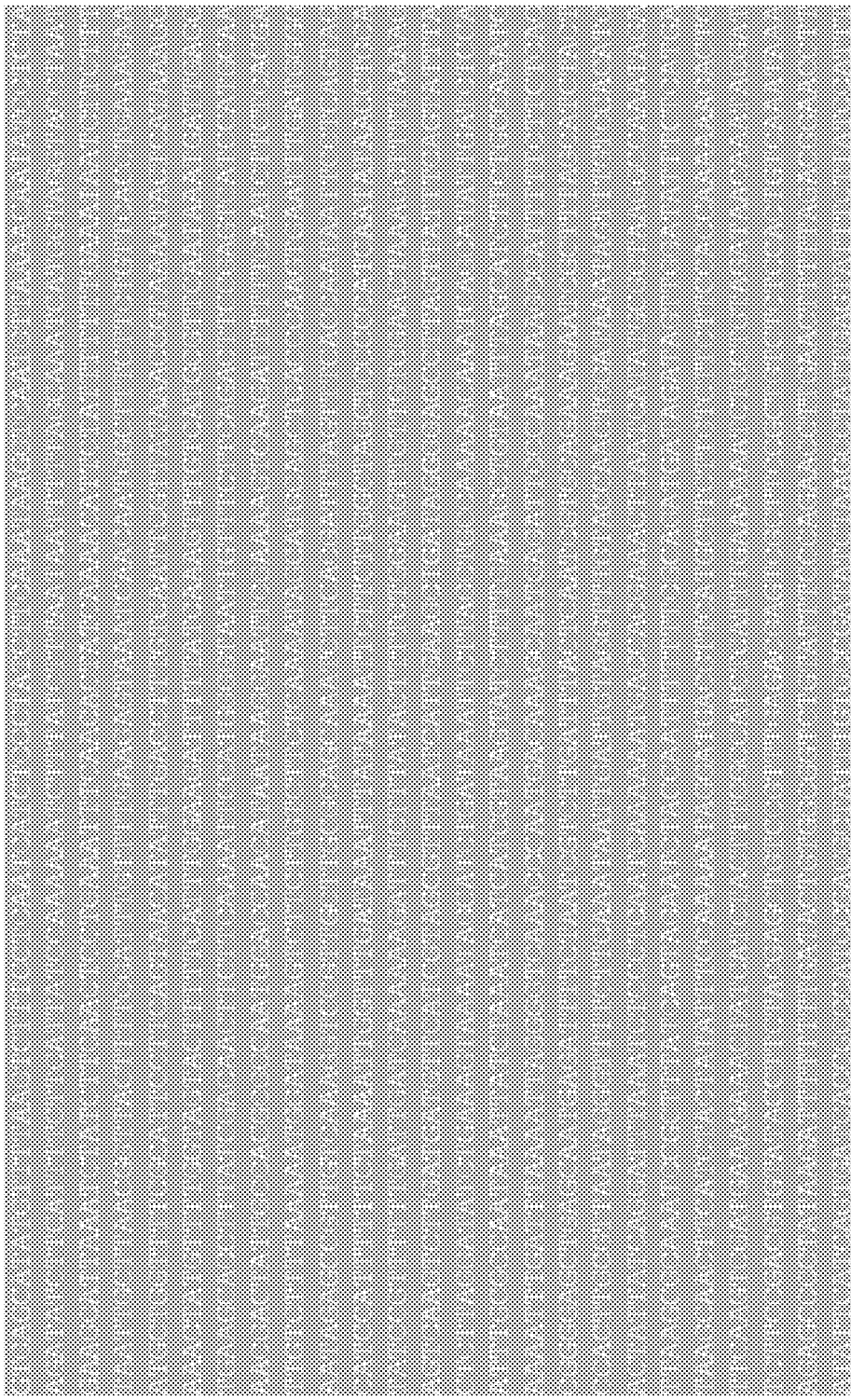
Figure 19, continued

Figure 19, continued

ABD2002: SaPI2 with deletions of *ptiB, cpmAB, tst, & eta*, insertions of *tetM* and CRISPR/cas9

SaPI2, tetM,

SEQ ID NO:3

Figure 20, continued

```
TTTGCCTATTATCTAATTCGACGTCTACTAAAATTTCAAAGTCAAAATTTTCAAT
CGAAAAAGCGTGAGTAATGTTTGCAGTTACTTCAAATCCCTCGAAAACATCATTA
ATTTTATAATTCGGTTCTTCATCAAAAGTAAAGTCAAAATTGATCGGATTATGT
CAAAAAATTCTGAAGGAGATATGTGCAGATAACTACATAATTTATCTATAGCATC
ATATCTTATCATTTCAGAATCATTTTGTGCCATTGAAGTAAGTGAACTTCTTGCT
ATTTTACATCTTTGCAACACGGAGATATTTTAGTCCTCTTTCTGACAGTAGTT
CAGACAATCTATTTCTAATCATTACAAACCTCCTAATTATGTTAATAATAGCATT
TTTTGGACGTTTATGTACAAAAAAATAAAAAATGATTGAGAAGTCAGTCGAAAA
ACTATTGCAAAAGAAAAACGATTATGTATAATAAAGTTATAAATTGATTGAGAAG
TCAGTCAAAAACGAAGGAGGATTTTAATTATGACTATTTAGCGAATACTAGAAA
GTTTAAAGAAGCCATGTTCTTAAAAGGCTTTAATTTATCTGATTTATCACGTGAA
ACAGGTCTTGGAATTTCTTATTTAAGCCAAATTATTAATGCTAAAAAGATTCCAA
GCCCTAAATTAGCTAAGAAAAATGGCAGAAGTTTTACAAGTTGAGGTAAATGAATT
ATTTGAATTTGAAGTAAAGGAGGCATAAACCAATGTTCAACATTAATATTGATGA
AGATGAAGCACGTGAGTTACTTGAGCAGGCTATCAATGCACGTGTGGACGAATTA
GCGAAAGAGAAATATTTTATGACTTACAAAGAGTTGTCTAACTATCTCAATTTAA
GTAAGCCTACTATTGAAGAATTACTTATTAATAATGGCATGAAATATTATATGGT
CGGATCTACGTACAGATTCAAAAAGTCTGATGTAGATGAATTCATGGAACAGCTT
ACTGCTCATATGAATATCCAGAATAACGACTTTAAACAAGTCAATATCAAAAAGT
TATGGAGGCAAGGCAATGAAAAATCTACTTAACTTATATCTGCTTAGTTTCATTG
TTAACAATATTATTACTAGCAATATCTAAGATGTATGTTGCTTTTAGCGTTTATG
CTTGGCTAATAACTTTAGGATGTAATTTAACAGGAGAGATTACAACGTGCGAAAA
CAAGTGATTATTACAAAAACAGTAGTTGGCTGGTACAACATTAAAGATACTCAAC
ATAATTAATGTTAAATATACCGCCAAAAGTATTGAACAGTACTTTCCTGATGT
TAGTAAAGATGTTCAAGTTGTGTGTTTAGAAATGGATTTATCAAAAATTACAGAA
ATTAAAAATAACAAAAAAGTAGGTAGTTAAGATGGGAATCAAACAAAAATATCAA
TTATCAAAAGTGGTTAAAATATTAGAAGTAGTATTATACGAGGAAGATAAGTTTC
AATCCGATAAGGACTATCATTATCAGGATAAAGCATTATATGAATATGCTTTAAA
GTTAGTTCATAATGGATTGTTCAATATTCTTGCTGAATTAGATTTTGAAGATGAA
GCATTTTTAATTCTTGATGAAGTAACAATGACGCTAAGTGATGTCATGAAAGAAA
CACAACACGTTTACCGTTATAGTCTCATAGATGAAAAAGGTGAACACAAACATAC
AACAGATCGCAAAGGACACGTGATTGGAATGTTAGAGTGGGCATTAGATTACATT
GCGGGAAATATTGAAGTGGAGGAATTATAAAATGAATTGGGAAATTAAAGATTTAA
TGTGTGATATTGAAGCGGTAAAAGAAAAAATCAATGATGTAGCTATCAAACATGC
TTGGTTTGTTGAAGATAGATTTGTAAAAAATGAATTAGAAACAAAACGGGAACAT
```

```
AATCGATGGCATCATTTTTGAACTCATTTCCAATGTTTAAAGATGATACACGTAA
TACACATCCTAAGTTTGTTACCAGTGCCACATATAACTTTTCTAGTGGTGAAAGT
AAATCAAGAAGTAATATTAATTTAACACTAAACGCTAAAAAAGAATGGCCAAATA
TTTTAATTTCTACTGGTGAATCATCTATCGCAAATATGGCTGATGAAAAAGCGGG
TGTATCAGCACGTGTAGTTACACTACAAGATCCACCATATCCAGATAATTTTGAT
TTTACCACATTAGACAAATCGTTTAGGGAGAACTATGGAACGTTAGGGTTGGCAT
TTATTAAACAATATGAGTCTAAAAAAGACGTGTATAAGAACGCTTTTGAGAGCTA
TCAACGGTATTTAATCAAAAAGGTACTAATGAAATCATGCAACCTTTAGGACGT
GCCTTTGCGTTACTACAAGTTACCGGTGAGGTTTTGAATGATATTGATGGGTTTG
AACATGACCATTTTAAAATTATCGAACAAGCCTATGACAGCATGGTTAAAAACAA
TAAGACGATTGATAAACCTAAGCAACTGTTAGAGGAACTATTACAATATTTAGAT
GCAAATAGAAATAATATCGCTGGTGATGGCTATAGTTCAGTCAAAAATGGTGACA
TCAAAGCTATATATAAACGTGATTATTTATGTATATTAGGTCAAACTGTACACGA
TAAATTAGGTCATGAAATGCAGACTATAACAGGTCAATGGGGCAAAAAAGGATAT
TTAATTAAAGGTGAAAAAGATCGCTTGCAAAAAAGGTGAGTCACAAAAACATTA
AGTATAGAGGATTTGCTATAAACAAAGAAATGCTTGAAGAATTAGGATTTGATTT
CTCGAATTCTCATAATCCTTATTCAGATTATTAAATAGTTGCCAAAGTTCCCGAT
AAGTTCCCCGCGAAAAACATACAAACGGGAACTATAAGACTACTTTAACCACAAGC
AATTAAAGTTAATAGTTCCCGAAGTTCCCAATAAATAATATTATTATTTATTATT
TGAAAACGAACAAATGTTGTTAGCTTTATACCATATATGATAGAAAATTTTTAAC
GGGTACAACGGGAACTAAGTTTATTTAAAGTTTATATATCAATGGTTTGACTAGT
TCCCGATAAGTATTTTAAGTCGGGAATTCAACGGGGACTAGTTCCCATTTAAAAA
TATTGGAGGTAACACATGGATAAAGAGCAACTTAAAAAGTATATATACGATTATG
TAAAAGAATATAAGGAGATACCGATATATCAGTTAGAAGATTTGTTTAAAGAAAT
GAATCACGACTATATAGGGAGAACCAGTGTCACACACGATAAGGATGAGAATATT
GTGTTTGGAGTGGATGGAACAAAATTACAATGTTTGCGCTGATTGAATTAGTTA
AAAGTGAACAACTTGATTTAGTGTATAGAGGTACTTTTGTAATGCGTTATTTGTT
GGATGGTAGAGTTCCTAACTTACCATTAGCAATTGTTATCCAGAAGATGGACAA
CAAACGGACGTGCCCTCATGCGTGCCTATGGTATTAAGAATAAATAAAGAGGAGA
AAATCAAATGAACATAGAAACTATCGTAAACCAATTTGAAACACGAGCAGGCACG
TTACTAAGGTACTACACAGCATTATTAGAACATAGTAAAGTGCAACCATGTTGCT
TTAAGTTATACAATGATCCATTTGATATGGCATACGTGATGATGAATGGGAAGTT
ATTCGGTCATGTATATATTAAAGATTCTAAAGTAAGGCAATCATTTGAATTAGCG
TCACCTAAGCACACTGAGGGCGCTTATAAGAACTATAGAAGGTCATTATGTACGTT
ATGAATTACATGACGGTAAACAGCTTTCTATTAGTGATATGATGGCCAGTCAATT
```

Figure 20, continued

```
ATTTGAAGATGAGTATTTTATGTATGGATTACAAACATATGCAGAATCAAATAAT
AGTGATGTGTTTGAGTACCTAGAAAATGGATTTGATACCGATACACTTGAGGGCA
TTCAATCGAGTAATACTGATGTGATAGCGAATATTGAAATGTTGTATCAGTTAGC
TACAGGAATCAATGAACCAGCACCAGAGTTAGTTGAGGGGTTGAGATTAGTAACT
GAGTTTGTACAAGATGAGAATGCCGACACAAGAGGATTACAAGGCTTTAGAGCATA
AGTTAACTGAGTTGAAGTCATCTTATTACAGTTTGAATAAGTAATTAAATATGGA
GTCTCACGTGGTGTGTGGCTCCTAATATAAAAGTATAAGGTATAGAAGTTTTAAA
ATGTAAAGGTTGCAACAATAGTGAGTTAATAGATAGGTAGGCGAAATTCAAAAAA
GTGTGAAATGTTGATATTGAGCTGTTTTATGGCTTTGAAAATAATAAGGTTATAT
AAAGGTGTTAGCTTTTAACATCGGAAGGTATACAGTGTTTGAGAATTGAAAAAAT
GGCAAGATTTGTGCAAGGTGTGAGAACTTTGTTAACGCTAATACAAGCTAAAGTT
TGTGTTTTGGCATAGGCCTAAAAGTTAAGTTTGTTCGCTGTTTGTTCGTGTTAT
TTTATCGAACTTAAGTTCTATATTAGGTTAATGTGAAAAGCCTAACGTTAAGTTT
ATAACATGATTTATAAGTGTTATATATGATAAGCTAAACAATTGATAAAACGCG
CTATAAAGCGAACGTAAGTTTGTTTTAGACCTGTAAAAATGGTATAATTTAGGTA
TGAAATAATTAAAAGAAAGAGGTGTAGAAATGCAAAGTATCAATTTAGCTAAGCA
AAACAGGATTATTAAATAGCAATGATTGCCTATCCAAGTCGGGTAGGCTCTGTTT
ATAGGGGTGAATAAATCAAACTGCTTAAAAACGAAGAATTGTTTATATTATCGTAA
TGGCGACAATAAACTATCTGAGTATCAACTATTAACGCAATTTAACCCAGCATTT
ATTTAATAAAAAAATTAAGATGTGTGAATTCCAAATTGAAAGTATGTACCATATGA
GTGCGTCGACCACAACATGTGATGAAATAATGGGGGTCGTGTCTGTCTCATATCC
GATTGAAAAATTAGTTATCAAAATTATTGAAACAAAAGCAGGGTTACAAAACTAT
AAAAATAGATCTATAAATAATATGGCGTTGTTTGAAAAAGGTACTAAATCATTATA
CAGAAAAAGAGCAGAAGTAAGTTGTAAAATATATGCGTTCAAATGGACGATATAA
GCCTTACAACGTCATTGAACGCTTACAAGTTGATTTGTATCAAGCAAGTATTAAA
CAACGTTCAGAACGTCAAAAACAAAGAAATACAGCAATTGAAAACAGTAAGATTG
CACGACTAAATGCATATCACCAATCTTCATATGTAAAAGTGGTGTAACAATGGAT
AAAAAGCAAATAAAAGACTTCGTTTGTGATTATCATAAGCGAACTAGAAGTGATG
TGTTGATAGATGATGAAATAAATACCGATGAATTCTTTTCAATAGGTGATGAAAA
TTCTAATGAATGGATGGCAGACGATAACATTGATGATCATATTGTAAAGAATCAC
TTAGAAATGATTGTTGACCAAGTAGCTAATGACAAAGAGTTTTATATTTTCGATT
CTTTAATACAAGGACGTAGTTTTAAAGATATTAGCAATGTCTTAGAGTGTTCAGA
ACAATCTGTAAGATTATGGTATGAAACCTTATTAGATAAAATTGTGGAGGTGATA
GAATGAGTGAGTTAACGGCAAAACAAGCGCGTTTTGTGAATGAGTATATAAGAAC
ACTTAATGTAACACAAAGTGCCATAAAAGCAGGCTATAGCGCAAATAGTGCACAT
```

```
GAAAATGGGGATTCCCACAATCTTTTTTATCAATAAGATTCACCAAAATCGAATT
GATTTATCAACGGTTTATCAGGATATTAAAGAGAAACTTTCTGCCCAAAATTGTAA
TCAAACAGAAGGTAGAACTGTATCCTAATATGTGTGTGACGAACTTTACCGAATC
TGAACAATGGGATACGGTAATAGAGCGAAACGATCACCTTTAGAGAAATATATC
TCCGGTAAATCATTAGAAGCATTGGAACTCGAACAAGAGGAAAGCATAAGATTTC
AGAATTGTTCTCTGTTCCCTCTTTATCATGGAAGTGCAAAAAGTAATATAGGGAT
TGATAACCTTATAGAAGTTATTACTAATAAATTTTATTCATCAACAGATCGAGGT
CCGTCTGAACTTTGCGGAAATGTTTCAAAATTGAATATACAAAAAAAGACAAC
GTCTTGCATATATACGCCTTTATAGTGGAGTACTACATTTACGAGATTCGGTTAC
AGTATCAGAAAAGAAAATAAAGTTACAGAAATGTATACTTCAATAAATGGT
GAATTATGTAAGATTGATAGAGCTTATTCTGGAGAAATTGTTATTTTGCAAAATG
AGTTTTTGAAGTTAAATAGTGTTCTTGGAGATACAAAACTATTGCCACAGAGAAA
AAAGATTGAAAATCCGCACCCTCTACTACAAACAACTGTTGAACCGAGTAAACCT
GAACAGAGAGAAATGTTGCTTGATGCCCTTTGGAAATCTCAGATAGTGATCCGC
TTCTACGATATTACGTGGATTCTACGACACATGAAATTATACTTTCTTTCTTAGC
GAAAGTACAAATGGAAGTGATTAGTGCACTGTTGCAAGAAAGTATCATGTGGAC
ATAGAACTAAAAGAGCCTACAGTCATTTATATGGAGAGACCGTTAAAAAATGCAC
AATATACCATTCACATCGAAGTGCCGCCAAATCCTTTCTGGGCTTCCATTGGTTT
ATCTGTATCACCGCTTCCGTTGGGAAGTGGAATGCAGTATGAGAGCTCGGTTTCT
CTTGGATACTTAAATCAATCATTTCAAAATGCAGTTATGAAGGGATACGCTATC
GTTGCGAACAAGGATTATATCGTTGCAATGTCACCGATTCTAAAATCTGTTTTAA
GTACGGTTTATACTTATAGCCCTGTTAGTACTTCAGCAGATTTCGGATGCTTACT
CCTATTGTACTGGAGCAAGCCTTTAGAAAAGCTGGAACAGAATTGTTAGAGCCAT
ATCTTAGTTTTAAAGTTTATGCACCACAGGAATATCTTTCACGGGCATATAACGA
TGCTCCCAAATATTGTGCAAATATCGTAAATACTCAACTGAAAAATAATGAGGTC
ATTATTATGGAGAAATTCCTGCTCGATGTATTCAAGATTATCGCAATGATTTAA
CTTTTTTACAAATGGGCTTAGTGTTTGTTTAGCAGAGCTAAAAGGATATCAGGT
TACCACTGGCGAACCTGTTTGCCAGACCCGTCGTCTAAATAGTCGGATAGATAAA
GTAAGATATATGTTCAATAAAATAACTTAGTGCGTTTATGTTGTTATATAAATA
TGGTTTCTTATTAAATAAGATGAAATATTCTTTAATATAGATTTGAATTAAAGTC
GAAAGGAGCAGATTGTTATTATAAACTACAAGTGGATATTGTGTCCTATTGTGC
AAATAAAACAAGACTACGAATACGAGTGGATACTATACTTAAAAATTTCCCTTTA
TACTGCCCAAATGTAAGAACCAAACTTTAATTAATGTTCAAAAAATGAACATAA
TAACAATCAAAGAGCCAGACGCCAAGACGCAGAGCCGATAATTTGAGAAATGAAA
TCTCATCTTATCGGCTCTTTTGTTATCTGAATTTTACTGACTAGCCTTCAAT
```

Figure 20, continued

ATTTCTTGCTTCATTGATACCTTTGCTAGTGCTTCCATTAAGGATAGTTCTTTC
TCTGTAAAGCTATCCATGTATTTTCTACCTGTAACCTTCCAGTGCTTTTAATCA
AATTATCTGTAGGTAAGAAAATTCATCAATACATACATGGAGTAATGATACAAG
ATCCCCTAAGGAATTATCTAAAACTTCACTATTTGTA

Figure 20, continued
SEQ ID NO:5

SEQUENCE LISTING

<160> NUMBER OF SEQ ID NOS: 37

<210> SEQ ID NO 1
<211> LENGTH: 3850
<212> TYPE: DNA
<213> ORGANISM: artificial sequence
<220> FEATURE:
<223> OTHER INFORMATION: ABD cargo sequence

<400> SEQUENCE: 1

```
cttttttttc gttctaccga tacaataaat ggataaagta ttatatgatt gttaaaaaac      60
gaaaaacctg ctgtccttta aatgtcccat ttagtaaaat ggaatgggag ggggaagtc     120 gttattgagc agatatgttt agattctgtc cggatcaaga attcggagag tagtgaacaa     180
gtgaaaataa tagatacaaa aattgatcaa tttgccaact acttacaacg tagaaataac     240
ttggatcgca tacaatttct aaaagttcgt ttaggtatgc aagttgtagt aagtaatata     300
gcgaaattta tagtaactta tgggttagcg ataatattcc atattttctg gtatacgtta     360
actatgcatt tagcatatat gattttgagg ttttatgcgc atggtgcaca tgctaaatca     420
tcattactgt gtcatattca aaacatcatt attttttctat tgatgccatg gcttatcgta     480 tattttttcaa taagtaaatt tgagatgctt ttctttgctt taatcggtta ctttatagta     540
attgcctttg cacctgctgc aacgaagaag caacctatac ctaaacgctt agtgaaaaag     600
aaacgaatac tctccattgt agtttacatg ttattagtat taatatcgtt tataattaaa     660
gagccatatt cacaattaat tttatttgga attattgttg aatcaattac attattacct     720
atctttttcc ctaaggagga ttaacattat ggaattttta gtcaatttat tttttaaatt     780
tttcacttca atcatggaat ttgttggttt tgtagctggt tatagtcctt gtactaactt     840
ctttgatgag ccagaagtac ctagcgaatt aactaagata tacgaataac atcatttaat     900
ttagaaagcg tgtattaaat ggaattaatc aataatatac cgtttgctat tttgcaatta     960 atttatact tttgggttac aaaattaata tcgtttatca aatatacaag aagagattat    1020
tttatcatca tagggattat aatctcttct cttgtattat acgaattatt tggtacgaaa    1080
```

```
tctttactat ttgtagtaat atctagccta attttcttat ataggaaaat taaattttat    1140
tctattttgg ctgttttaat tacttcattg ataatgtatt tgagcaactt cactacttta    1200
gtattgtacg taacagtttt agataaaatc actgatacat atatactact tacaatatac    1260
atgctagtat ttttttatagt ttctttgata acttctctag ttctgagatt tttattacaa   1320
aaactaaaaa catcatacct ttcaatgaat aaaacatata atattatcat cgccttagta    1380
ttagtaatat cgtttgtatt ttttttactct tattctttag ttaatacttc tgcattcgaa   1440
agcttaagaa gttatggaat tattttttgtt ggtttaatta tctttttaag catcattatt   1500
ttcattcttt caatgggtac caaagaggtc atggatttta aatttcggtt aaaacgtttc    1560
tccgaaaaat tcaactatca ggacagtatt tttaaatata ctcagctaat gagggggtgta   1620 acttctcttc aacaagtttt taaagaactg aaaaatacta tactggatgt tttgcttgta   1680
agcaaagctt ataccttttga ggttactcct gatcacaaag tgatattttt agataagcat   1740
gaagttggac cggactggaa tttttatcaa gaggaatttg aaaacgtaac ttcagaaatt    1800
gggaaaatta tagaagtcaa tcaaggcttt cttatgaaag ttggtgaacg aggcggtagt    1860
tcttatgttc tgctttgttt atctaatatt aacactcccc ggctaacacg tgatgaaata    1920
tcgtggctga aaacactgtc ttttttataca agtgtgtcca tggaaaatgt cctgcatatt   1980
gaggagctca tggaacattt gaaggactta aaacaagagg gaaccaaccc catctggctg    2040
aaaaagctaa tgtttgcaat cgaagaaaaa cagcgttcag gactcgcccg cgatctccac    2100
gattcggttc tcaggatttt gatttcctta aaacgccagt gtgagctgtt tttgggtgat    2160
ttcaagaagg atgataatcc gtgccgtgaa gaggtgcagg acaagcttgt acagatgaat    2220
gagcagatgt ctgatgtgat ttcgatgacg agggagacgt gtcatgagct gcggccgcag    2280
cttctgtatg atcttggatt ggtgaaggcg ctgtcgaagc tggtggcgca gcagcaggag    2340
cgggttccgt ttcatatccg tttaaatacc gggagattta cggcttccct tgatctggat    2400
tcgcagctga atttgtaccg gatcattcaa gagtttctgt ctaatgcggt caagcactct    2460
caggcgacgg atgtgctgat tatgctcatc agtattcaaa acaaaatcgt tcttcattat    2520
gaggacgatg gcgttgggtt tgatcaagaa aaaaatactg agcattccat gagcatgggg    2580
ctttctggca ttaaggagag agtcagggct ttagatgggc gccttcggat tgaaacaagt    2640
gaaggaaagg gctttaaggc tgatattgaa atcgaattgt aatggattta taacggaaac    2700
gacttggcac aggccaagtc ttttttataa aatggaaaag agtgagtaaa agggaggaaa    2760
acatgaaaaa gatactagtg attgatgacc atccggctgt catggaaggc accaagacaa    2820
ttttggaaac ggattcgaat ttgtctgttg attgtctcag tcctgaaccg agcgaacagt    2880
ttatcaagca gcatgatttc tcgtcatatg atctcatttt aatggatctg aatctaggcg    2940
gcgaggtcaa tgggatggag cttctaaac agattttaca agagaatcct cattgtaaaa    3000
ttatcgtgta taccggttat gaggtcgagg attatttcga ggaagcgatt cgtgcgggtc    3060
tgcacggtgc catcagcaaa acggaatcta agaaaaagat cacccaatac atataccacg    3120
tactcaacgg agaaatttta gtcgattttg cttactttaa acagctgatg actcagcaaa    3180
aaacaaagcc ggctccttcc tctcaaaaag aacaagatgt gctcacacct agagaatgcc    3240
tgattcttca agaagttgaa aagggatttta caaaccaaga aatcgcagat gcccttcatt    3300
taagcaagcg gtccattgaa tacagcttga catcgatttt caataagctg aatgtcggtt    3360
cacgacggaa agcggttttg attgcgaaat cagacggtgt actttaaatg ttgggggggtg    3420 tagagatgga tatgaagcac acattgcttg aagcgcttgg tattgagatt gttgaaaaca    3480
```

```
cagcggaacg atgcgttgcg gtcatgccgg tggatcatcg gacggtacag ccgttcggat    3540
atttgcatgg aggcgcttca gtggccctgg cggaaaccgc ggcgagcgca ggtgcacaga    3600
acctgattga tcatacaacg caagcttgtg ttggtttgga gattaacgcc aaccatttaa    3660
aatctgtaaa ggaaggaacg gtaaaggcga tagccgagcc cgttcatata ggcagaacga    3720
cgattgtcta tcatattcac atatatgacg agcaagagag gctgatctgt atatccagat    3780
gcacgctggc tgtcatcaag aaataaaaaa acagccggaa ctctgcctgt ccggctgctt    3840
atttctcgag                                                            3850

<210> SEQ ID NO 2
<211> LENGTH: 10355
<212> TYPE: DNA
<213> ORGANISM: artificial sequence
<220> FEATURE:
<223> OTHER INFORMATION: ABD vector

<400> SEQUENCE: 2
atgccaggaa tgatgtaaaa tgactgttaa acgccgattt tataacgttt gtaatattgg      60
gtggtcataa tttggtcata gaaattttaa aataaatctt ttgagacgtt ttccatgagt     120
ttactaaact tttgagaagc gtctttttg tatgagttcg taatcttagc gtagatgttc     180
atagtggtat ttatatcttt atggcgcaag cgttcttgta tttccttaat atgcacacca     240
gcctctataa gtaacgcaca atgagtatga cgaaatgaat gagtgcttat tgtttattta     300
gttatgtcag tctttttaag tatagctttt atccataatt gtagtttttt aattacaaga     360
gggtagccgt taacatcagt aaaaacgaaa ttattatcta catacaattc gttttttccat    420 gtgtcctgca cgtcggtttt ataatttta agtaatttaa tcacatgagg atccactgaa     480
atttttccga ttgagctttc agtttttggt gtaagtattt gaaattgctt tttattgtta     540
ttcggattgt aataagtctt tgtaatattg attgtgttat tctcaaagtc tatatcagac     600
catttcaatg ccaataattc acctgcacgc atgcctgtat atgctaatgt acaaaacacc     660
tcaaagctgt tttggggtga atggtgattt ttagcaacct ccaggaattg aaataattca     720
tctttttcaa gaaacttttt atgtatctca gtatcttcta attcttccac actaattttc     780
tttttaggtc gtttaatacc ctcgctaggc attattctta ttaatttcat atcgtatgcg     840
tacttaaata tcatatttgt agaggctata atgctatcaa cataattctt gctatactgt     900
gcgcttatat cgtttacaaa acgttgatat tcatgtttat tgatagtttg tattggttta     960
ttgttaaagc gttctatggc gtggtttatg ctttctcgc gtgctctgac actacttact    1020
tttacttcgt tagcatattg tgatatccaa tcgtcagcaa cctgtttaaa tgtagatgtg    1080
gacggtgcga taatcgcc atttcttaac tgacgctcaa ccatttcagc gtgatgttta     1140
gcgtctgatt tgcgtttaaa acctgagttt gaaatatatt tatatttgcc cgttctgcg    1200 tcttttccta gtgatatacg atagcgccat gtatttccgc gttttcata acttgccatt    1260 tgatcacctc gattaatatt ctttaaaaat atcactagat aaacggctat cagtttgtaa    1320 aatttctttta tgtagagtcg tacttttttc gcctttattt ggaaaaagct cttcaatatc    1380
gtctatattt tttactatta tttcagaaac atacccactt aacttttggt taattttttt    1440
aaataacaag ttttaaggc ctgcagataa actatcaacg tattttttta atccgatatt    1500
ttcatcttca ttttaatcg tgaaaataaa tctatgttgt gaattagtta tcttttcagt    1560 ttcttatat gagacgtcta agtcaaaatt taatttttgc ctattatcta attcgacgtc    1620
```

-continued

```
tactaaaatt tcaaagtcaa aattttcaat cgaaaaagcg tgagtaatgt ttgcagttac    1680
ttcaaatccc tcgaaaacat cattaatttt ataattcggt tcttcatcaa aagtaaagtc    1740
aaaattgatc ggattatgtt caaaaaattc tgaaggagag atgtgcagat aactacataa    1800
tttatctata gcatcatatc ttatcatttc agaatcattt tgtgccattg aagtaagtga    1860
acttcttgct atttttacat cttttgcaac acgagatatt tttagtcctc tttctgacag    1920
tagttcagac aatctatttc taatcattac aaacctccta attatgttaa taatagcatt    1980
tttttggacg tttatgtaca aaaaataaaa aaatgattga gaagtcagtc gaaaaactat    2040
tgcaaaagaa aaacgattat gtaataaaa gttataaatt gattgagaag tcagtcaaaa     2100
acgaaggagg attttaatta tgactatttt agcgaatact agaaagttta aagaagccat    2160
gttcttaaaa ggctttaatt tatctgattt atcacgtgaa acaggtgttg gaatttctta    2220
tttaagccaa attattaatg gtaaaaagat tccaagccct aaattagcta agaaaatggc    2280
agaagtttta caagttgagg taatgaatt atttgaattt gaagtaaagg aggcataaac     2340
caatgttcaa cattaatatt gatgaagatg aagcacgtga gttacttgag caggctatca    2400
atgcacgtgt ggacgaatta gcgaaagaga atattttat gacttacaaa gagttgtcta     2460
actatctgaa tttaagtaag cctactattg aagaattact tattaataat ggcatgaaat    2520
attatatggt cggatctacg tacagattca aaaagtctga tgtagatgaa ttcatggaac    2580
agcttactgc tcatatgaat atccagaata acgactttaa acaagtcaat atcaaaaagt    2640
tattggaggc aaggcaatga aaatctactt aacttatatc tgcttagttt cattgttaac    2700
aatattatta ctagcaatat ctaacatgta tgttgctttt agcgtttatg cttggctaat    2760
aactttagga tgtaatttaa caggagagat tacaacgtgc gaaacaagt gattattaca     2820 aaaacagtag ttggctggta caacattaaa gatactcaac ataatttaat gttaaatata    2880
ccgccaaaag tatttgaaca gtactttcct gatgttagta agatgttca agttgtgtgt     2940 ttagaaatgg atttatcaaa aattacagaa attaaaaata agaaaaagt aggtagttaa     3000 gatgggaatc aaacaaaaat atcaattatc aaaagtggtt aaaatattag aagtagtatt    3060
atacgaggaa gataagtttc aatccgataa ggactatcat tatcaggata agcattata     3120 tgaatatgct ttaaagttag ttcataatgg attgttcaat attcttgctg aattagattt    3180
tgaagatgaa gcatttttaa ttcttgatga agtaacaatg acgctaagtg atgtcatgaa    3240
agaaacacaa cacgtttacc gttatagtgt catagatgaa aaaggtgaac acaaacatac    3300
aacagatcgc aaaggacacg tgattggaat gttagagtgg gcattagatt acattgcggg    3360
aaatattgaa gtggaggaat tataaatgaa ttgggaaatt aaagatttaa tgtgtgatat    3420
tgaagcggta aaagaaaaaa tcaatgatgt agctatcaaa catgcttggt tgttgaaga    3480 tagatttgta aaaaatgaat tagaaacaaa acgggaacat attaattttt ctgctagcta    3540
tttagaacat cgtatacaaa atgaacatac agttgagtta ttacatgtgt acttaaaaga    3600
attcggtgaa cttatacaaa aatttcatga atagaaaaa gcatcatctg agaactttgg    3660
cgaggtatca gatgacgcac aaaaattaaa aatcacagag taatttagaa attacacatg    3720
tttattataa catttttac tctgtgaatc actagaggtg caaaaaatga atgaaattaa     3780
attagaatat gacacacatg tttcagtggt acattatgaa agtttagact cacgttcatt    3840
taatagcttt tcaaaaatta attggagtaa gttggttaat aaactgtctg tacctataga    3900
agcaaattat aagtatgcac gtggtgttgc tgtttacggt gatattaaaa acggtgcaaa    3960
tgatcaaggt gaaattatca aaaagcatcg aaacgataaa aatgtcatat acagagatgt    4020
```

```
gattgtactt gattatgatg aaataaatga tttaaagcaa ttacatgaag caatcagctc    4080
agctttaagc aatgttgcat ggttttggca cacaagttac tcgcacagaa ctgaacaagc    4140
tagaatacgc ctgtatatcc ctctaaatga gcgaataagt gcagatgatt atcgtaaata    4200
tacaaaagta ttagcaaata aaattggcca taaagtggaa gaaggttcat atcagccaag    4260
tagatgtttt gcgttaccag ttattcaaaa aggacacata tttattaagc gagtgaatga    4320
ctgtccaatt atgaatgttg atatgctcga acagtggtcg aaggagtttg aacaatcaaa    4380
tgctagtcct aatgtcatag gatacactcg acgcgatagt gagtactggc gcgagctatg    4440 cttttggaaca accgaaggca atcgtaacaa tgcactagct agcttaattg gcatttatt    4500 aagatgtcac gttaatgatt atattgttta ttcatttgct ttactatggg ggcaattcgc    4560
atgtaaacca cctatgaaag aacaagaaat caacgccact tttcaatcga tattaaataa    4620
acactataac aattagaaag gggctttgta tggaaacagg taaaagtgat gtacttgata    4680
aaattgaaaa aattaataaa aaagatagtg cctacaagaa aattatacca aaaggttatg    4740
aaattgaaca tcatcaatgc ggtattgcct taaatcaact tataccaagt aaaaaagaag    4800
gcgagccaga taaaaaggtt tttatcacaa gtacaatccc tcaaatcact gaacgctttg    4860
aagatattga gagtaacgaa gtcagcttta atatgctttt ctatgacaat aaaacgccag    4920
taaatatagc tgtgagtgcc gaagaaattt cagatagtcg tcaactcttg aaattggtta    4980
ataaaaagct ggatgtaaca tcgtcgacat ctactaaact tgttgattat attaatgcat    5040
ctaaacggta taatccacca ttgaatgtta aagttgcaac gcgtttgggg catgtgaaag    5100
gttattttat ttatccttat caagaagtga tgaaagacag caatatcaag ttgtttagta    5160
atgataaagg atttcaaaag ttaatagact cttttcaaag caaggaaca ttagaaggtt    5220 actctaaaaa agtgttcggt caaataaaag atctaccaat ggtaatggtt atgttatatg    5280
cctctttagg ttcggtttta ttaagagaat ttggattaca gcccttttatt gtagaaatat    5340 caggtagtac atctacaggt aaaacattca cactcaactt agtatcaagt gtttggggaa    5400
cgagcgacct tatcacgaca tggagttcta ctcaaaatag tattgaatcg atggcatcat    5460
ttttgaactc atttccaatg tttaaagatg atacacgtaa tacacatcct aagtttgtta    5520
ccagtgccac atataacttt tctagtggtg aaagtaaatc aagaagtaat attaatttaa    5580
cactaaacgc taaaaagaa tggcgaaata ttttaatttc tactggtgaa tcatctatcg    5640
caaatatggc tgatgaaaaa gcgggtgtat cagcacgtgt agttacacta caagatccac    5700
catatccaga taattttgat tttaccacat tagacaaatc gtttagggag aactatggaa    5760
cgttagggtt ggcatttatt aaacaatatg agtctaaaaa agacgtgtat aagaacgctt    5820
ttgagagcta tcaacggtat tttaatcaaa aggtagtaa tgaaatcatg caacgtttag    5880
gacgtgcctt tgcgttacta caagttaccg gtgaggtttt gaatgatatt gatgggtttg    5940
aacatgacca ttttaaaatt atcgaacaag cctatgacag catggttaaa acaataaga    6000 cgattgataa acctaagcaa ctgttagagg aactattaca atatttagat gcaaatagaa    6060
ataatatcgc tggtgatggc tatagttcag tcaaaaatgg tgacatcaaa gctatatata    6120
aacgtgatta tttatgtata ttaggtcaaa ctgtacacga taaattaggt catgaaatgc    6180
agactataac aggtcaatgg ggcaaaaag atatttaat taaaggtgaa aaagatcgct    6240
tgcaaaaaaa ggtgagtcac aaaaaacatta agtatagagg atttgctata aacaaagaaa    6300
tgcttgaaga attaggattt gatttctcga attctcataa tccttattca gattattaaa    6360
```

```
tagttcccaa agttcccgat aagttcccgc gaaaaacata caaacgggaa ctataagact    6420
actttaacca caagcaatta aagttaatag ttcccgaagt tcccaataaa taatattatt    6480
atttattatt tgaaaacgaa caaatgttgt tagctttata ccatatatga tagaaaattt    6540
ttaacgggta caacgggaac taagtttatt taaagtttat atatcaatgg tttgactagt    6600
tcccgataag tattttaagt cgggaattca acggggacta gttcccattt aaaaatattg    6660
gaggtaacac atggataaag agcaacttaa aaagtatata tacgattatg taaaagaata    6720
taaggagata ccgatatatc agttagaaga tttgtttaaa gaaatgaatc acgactatat    6780
agggagaacc agtgtcacac acgataagga tgagaatatt gtgttttgga gtggatggaa    6840
caaaattaca atgtttgcgc tgattgaatt agttaaaagt gaacaacttg atttagtgta    6900
tagaggtagt tttgtaatgc gttatttgtt ggatggtaga gttcctaact taccattagc    6960
aatttgttat ccagaagatg gacaacaaac ggacgtgccc tcatgggtgc ctatggtatt    7020
aagaataaat aaagaggaga aaatcaaatg aacatagaaa ctatcgtaaa ccaatttgaa    7080
acacgagcag gcacgttact aaggtactac acaggattat tagaacatag taaagtgcaa    7140
ccatgttgct ttaagttata caatgatcca tttgatatgg catacgtgat gatgaatggg    7200
aagttattcg gtcatgtata tattaaagat tgtaaagtaa ggcaatcatt tgaattagcg    7260
tcacctaagc acactgaggg gcttataaga agtatagaag gtcattatgt aggttatgaa    7320
ttacatgacg gtaaacagct ttctattagt gatatgatgg ccagtcaatt atttgaagat    7380
gagtatttta tgtatggatt acaaacatat gcagaatcaa ataatagtga tgtgtttgag    7440
tacctagaaa atggatttga taccgataca cttgagggca ttcaatcgag taatactgat    7500
gtgatagcga atattgaaat gttgtatcag ttagctacag gaatcaatga accagcacca    7560
gagttagttg aggggttgag attagtaact gagtttgtac aagatgagaa tgcgacacaa    7620
gaggattaca aggctttaga gcataagtta actgagttga agtcatctta ttacagtttg    7680
aataagtaat taaatatgga gtctcacgtg gtgtgtggct cctaatatat taatagatag    7740
gtaggcgaaa ttcaaaaaag tgtgaaatgt tgatattgag ctgttttatg gctttgaaaa    7800
tttgagaatt gaaaaaatgg caagatttgt gcaaggtgtg agaactttgt taacgctaat    7860
acaagctaaa gtttgtgttt ttggcatagg cctaaaagtt aagtttgttc gctgtttgtt    7920
cgtaaagtat aaggtataga agttttaaaa tgtaaaggtt gcaacaatag tgaggttatt    7980
ttatcgaact taagttctat attaggttaa tgtgaaaagc ctaacgttaa gtttataaca    8040
tgattttata agtgttatat atgataagct aaacaattga taaaacgcgc tataaagcga    8100
acgtaagttt gttttagacc tgtaaaaatg gtataattta ggtatgaaat aattaaaaga    8160
aagaggtgta gaaatgcaaa gtatcaattt agctaagcaa aacaggatta ttaaatagca    8220
atgattgcct atccaattcg ggtaggctct gtttataggg gtgaataaat gaaactgctt    8280
aaaacgaaga attgttttata ttatcgtaat ggcgacaata aactatctga gtatcaacta    8340
ttaacgcaat ttaacccagc atttattaat aaaaaaatta agatgtgtga attccaaatt    8400
gaaagtatgt accatatgag tgcgtcgacc acaacatgtg atgaaataat ggggtcgtg    8460 tctgtctcat atccgattga aaattagtt atcaaaatta ttgaaacaaa agcagggtta    8520
caaaactata aaatagatc tataaataat atggcgttgt tgaaaaaggt actaaatcat    8580
tatacagaaa aagagcagaa gcaagttgta aaatatatgc gttcaaatgg acgatataag    8640
ccttacaacg tcattgaacg cttacaagtt gatttgtatc aagcaagtat taaacaacgt    8700
tcagaacgtc aaaaacaaag aaatacagca attgaaaaca gtaagattgc acgagtaaat    8760
```
gcatatcacc aatcttcata tgtaaaagtg gtgtaacaat ggataaaaag caaataaaag    8820
acttcgtttg tgattatcat aagcgaacta gaagtgatgt gttgatagat gatgaaataa    8880
ataccgatga attcttttca ataggtgatg aaaattctaa tgaatggatg gcagacgata    8940
acattgatga tcatattgta aagaatcact tagaaatgat tgttgaccaa gtagctaatg    9000
acaaagagtt ttatattttc gattctttaa tacaaggacg tagttttaaa gatattagca    9060
atgtcttaga gtgttcagaa caatctgtaa gattatggta tgaaacctta ttagataaaa    9120
ttgtggaggt gatagaatga gtgagttaac ggcaaaacaa gcgcgttttg tgaatgagta    9180
tataagaaca cttaatgtaa cacaaagtgc cataaaagca ggctatagcg caaatagtgc    9240
acatgtgaca ggatgtaggt tattaaagaa gccacacatc aagcaatata caagaaca     9300 aaaagataag attatagatg agaatgtatt aaccgcaaaa gagttactac atgtgcttac    9360
gaatgcggca gtcggtgatg agacagaaac gaaagaagtt gtagtcaagc gaggggaata    9420
taaagagaat ccacaaagtg gcaaagtaca gctagtctat aacgaacatg ttgaactgat    9480
agaggtacca ataaaaccta gtgatcgttt aaaagctcgt gatatgttgg gtaaatacca    9540 taagttatttt acagataagc atgatattaa cggggaatgtg cctatattca ttaatattgg    9600
tgaatgggat ggcgatgatg aagatttaga taagacggta caagaggtat ctaacgctaa    9660
tcctaatcat actgtgattg tggatgatat accgttagag gattgattac agtaaaaacg    9720
attatcatat tgagttagtg aggattagtt tactaattca ccctagcttt atattaaagc    9780
gttataaaga taaagggag aacgcttatt ataattaacg gactcccttt attaataatt    9840
attacagaaa aagtggtaaa gtttaatgtg gattaatatg atgttgtttc gggaaatata    9900
tgtatttatc tattttttgat attttatatt cagtataata cgtgattaca acgttgaata    9960
taaaaaaata tgacgatgtt tatacgtatt aatattaata taatcacacg ttgcaggcat   10020
caaacgctta tttattaatc aaaaatgggt ggacaaattt atatagtttt atcaatttta   10080
atattttaca ctaactttat taggtgatat aagatgctga gataagcatt atattgcaat   10140
gaaaaagcat tatatggata atcatatcta tcattgcaaa tacttata gagatttatg     10200 tgtgtgataa ttggtggtca taaattggtc ataatgaaat aaaaaaacta aaaaaattga   10260
atgcataaag aatacacgat gctgatttaa taggattttt gtatatgatt tatatctatt   10320
tcatactgcc cttaatgcca ggaatgatgt aaaat                              10355

<210> SEQ ID NO 3
<211> LENGTH: 18130
<212> TYPE: DNA
<213> ORGANISM: artificial sequence
<220> FEATURE:
<223> OTHER INFORMATION: ABD2002 with Cas9 insert

<400> SEQUENCE: 3
atgccaggaa tgatgtaaaa tgactgttaa acgccgattt tataacgttt gtaatattgg      60
gtggtcataa tttggtcata gaaattttaa aataaatctt ttgagacgtt ttccatgagt     120
ttactaaact tttgagaagc gtcttttttg tatgagttcg taatcttagc gtagatgttc     180
atagtggtat ttatatcttt atggcgcaag cgttcttgta tttccttaat atgcacacca    240
gcctctataa gtaacgcaca atgagtatga cgaaatgaat gagtgcttat tgtttatta    300 gttatgtcag tcttttttaag tatagctttt atccataatt gtagttttttt aattacaaga    360 gggtagccgt taacatcagt aaaaacgaaa ttattatcta catacaattc gttttttccat    420

```
gtgtcctgca cgtcggtttt ataatttta agtaatttaa tcacatgagg atccactgaa    480 attttttccga ttgagctttc agttttggt gtaagtattt gaaattgctt tttattgtta    540
ttcggattgt aataagtctt tgtaatattg attgtgttat tctcaaagtc tatatcagac    600
catttcaatg ccaataattc acctgcacgc atgcctgtat atgctaatgt acaaaacacc    660
tcaaagctgt tttggggtga atggtgattt ttagcaacct ccaggaattg aaataattca    720 tcttttttcaa gaaactttt atgtatctca gtatcttcta attcttccac actaatttc    780 tttttaggtc gtttaatacc ctcgctaggc attattctta ttaatttcat atcgtatgcg    840
tacttaaata tcatatttgt agaggctata atgctatcaa cataattctt gctatactgt    900
gcgcttatat cgtttacaaa acgttgatat tcatgtttat tgatagtttg tattggttta    960
ttgttaaagc gttctatggc gtggtttatg gctttctcgc gtgctctgac actacttact   1020
tttacttcgt tagcatattg tgatatccaa tcgtcagcaa cctgttaaa tgtagatgtg   1080 gacggtgcga tataatcgcc atttcttaac tgacgctcaa ccatttcagc gtgatgttta   1140
gcgtctgatt tgcgtttaaa acctgagttt gaaatatatt tatatttgcc cgtttctgcg   1200
tcttttccta gtgatatacg atagcgccat gtatttccgc gttttcata acttgccatt   1260 tgatcacctc gattaatatt ctttaaaaat atcactagat aaacggctat cagtttgtaa   1320
aatttcttta tgtagagtcg tactttttc gcctttattt ggaaaaagct cttcaatatc   1380
gtctatattt tttactatta tttcagaaac atacccactt aacttttggt taatttttt   1440 aaataacaag ttttttaaggc ctgcagataa actatcaacg tatttttta atccgatatt   1500 ttcatcttca ttttttaatcg tgaaaataaa tctatgttgt gaattagtta tcttttcagt   1560
ttctttatat gagacgtcta agtcaaaatt taatttttgc ctattatcta attcgacgtc   1620
tactaaaatt tcaaagtcaa aattttcaat cgaaaaagcg tgagtaatgt ttgcagttac   1680
ttcaaatccc tcgaaaacat cattaatttt ataattcggt tcttcatcaa agtaaagtc    1740 aaaattgatc ggattatgtt caaaaaattc tgaaggagat atgtgcagat aactacataa   1800
tttatctata gcatcatatc ttatcatttc agaatcattt tgtgccattg aagtaagtga   1860
acttcttgct attttacat cttttgcaac acgagatatt tttagtcctc tttctgacag   1920
tagttcagac aatctatttc taatcattac aaacctccta attatgttaa taatagcatt   1980 ttttggacg tttatgtaca aaaaaataaa aaatgattga aagtcagtc gaaaaactat    2040 tgcaaaagaa aaacgattat gtataataaa gttataaatt gattgagaag tcagtcaaaa   2100
acgaaggagg attttaatta tgactatttt agcgaatact agaaagtta aagaagccat   2160 gttcttaaaa ggctttaatt tatctgattt atcacgtgaa acaggtgttg gaatttctta   2220
tttaagccaa attattaatg gtaaaaagat tccaagccct aaattagcta gaaaatggc    2280 agaagtttta caagttgagg taaatgaatt atttgaattt gaagtaaagg aggcataaac   2340
caatgttcaa cattaatatt gatgaagatg aagcacgtga gttacttgag caggctatca   2400
atgcacgtgt ggacgaatta gcgaaagaga atattttat gacttacaaa gagttgtcta   2460
actatctgaa tttaagtaag cctactattg aagaattact tattaataat ggcatgaaat   2520
attatatggt cggatctacg tacagattca aaaagtctga tgtagatgaa ttcatggaac   2580
agcttactgc tcatatgaat atccagaata acgactttaa acaagtcaat atcaaaaagt   2640
tattggaggc aaggcaatga aaatctactt aacttatatc tgcttagttt cattgttaac   2700 atattatta ctagcaatat ctaacatgta tgttgctttt agcgttatg cttggctaat     2760 aactttagga tgtaatttaa caggagagat tacaacgtgc gaaaacaagt gattattaca   2820
```

```
aaaacagtag ttggctggta caacattaaa gatactcaac ataatttaat gttaaatata    2880
ccgccaaaag tatttgaaca gtactttcct gatgttagta aagatgttca agttgtgtgt    2940
ttagaaatgg atttatcaaa aattacagaa attaaaaata agaaaaaagt aggtagttaa    3000
gatgggaatc aaacaaaaat atcaattatc aaaagtggtt aaaatattag aagtagtatt    3060
atacgaggaa gataagtttc aatccgataa ggactatcat tatcaggata aagcattata    3120
tgaatatgct ttaaagttag ttcataatgg attgttcaat attcttgctg aattagattt    3180
tgaagatgaa gcattttaa ttcttgatga agtaacaatg acgctaagtg atgtcatgaa    3240
agaaacacaa cacgtttacc gttatagtgt catagatgaa aaaggtgaac acaaacatac    3300
aacagatcgc aaaggacacg tgattggaat gttagagtgg gcattagatt acattgcggg    3360
aaatattgaa gtggaggaat tataaatgaa ttgggaaatt aaagatttaa tgtgtgatat    3420
tgaagcggta aaagaaaaaa tcaatgatgt agctatcaaa catgcttggt ttgttgaaga    3480
tagatttgta aaaaatgaat tagaaacaaa acgggaacat attaattttt ctgctagcta    3540
tttagaacat cgtatacaaa atgaacatac agttgagtta ttacatgtgt acttaaaaga    3600
attcggtgaa cttatacaaa aatttcatga aatagaaaaa gcatcatctg agaactttgg    3660
cgaggtatca gatgacgcac aaaaattaaa aatcacagag taatttagaa attacacatg    3720
tttattataa catttttac tctgtgaatc actagaggtg caaaaatga atgaaattaa    3780 attagaatat gacacacatg tttcagtggt acattatgaa agtttagact cacgttcatt    3840
taatagcttt tcaaaaatta attggagtaa gttggttaat aaactgtctg tacctataga    3900
agcaaattat aagtatgcac gtggtgttgc tgtttacggt gatattaaaa acggtgcaaa    3960
tgatcaaggt gaaattatca aaaagcatcg aaacgataaa aatgtcatat acagagatgt    4020
gattgtactt gattatgatg aaataaatga tttaaagcaa ttacatgaag caatcagctc    4080
agctttaagc aatgttgcat ggttttggca cacaagttac tcgcacagaa ctgaacaagc    4140
tagaatacgc ctgtatatcc ctctaaatga gcgaataagt gcagatgatt atcgtaaata    4200
tacaaaagta ttagcaaata aaattggcca taaagtggat gaaggttcat atcagccaag    4260
tagatgtttt gcgttaccag ttattcaaaa aggacacata tttattaagc gagtgaatga    4320
ctgtccaatt atgaatgttg atatgctcga acagtggtcg aaggagtttg aacaatcaaa    4380
tgctagtcct aatgtcatag gatacactcg acgcgatagt gagtactggc gcgagctatg    4440
ctttggaaca accgaaggca atcgtaacaa tgcactagct agcttaattg ggcatttatt    4500
aagatgtcac gttaatgatt atattgttta ttcatttgct ttactatggg ggcaattcgc    4560
atgtaaacca cctatgaaag aacaagaaat caacgccact tttcaatcga tattaaataa    4620
acactataac aattagaaag gggctttgta tggaaacagg taaagtgat gtacttgata    4680 aaattgaaaa aattaataaa aaagatagtg ccttacaaga aattatacca aaaggttatg    4740
aaattgaaca tcatcaatgc ggtattgcct taaatcaact tataccaagt aaaaaagaag    4800
gcgagccaga taaaaaggtt tttatcacaa gtacaatccc tcaaatcact gaacgctttg    4860
aagatattga gagtaacgaa gtcagcttta atatgctttt ctatgacaat aaaacgccag    4920
taaatatagc tgtgagtgcc gaagaaattt cagatagtcg tcaactcttg aaattggtta    4980
ataaaaagct ggatgtaaca tcgtcgacat ctactaaact tgttgattat attaatgcat    5040
ctaaacggta taatccacca ttgaatgtta aagttgcaac gcgtttgggg catgtgaaag    5100
gttattttat ttatccttat caagaagtga tgaaagacag caatatcaag ttgtttagta    5160
```

```
atgataaagg atttcaaaag ttaatagact cttttcaaag caaaggaaca ttagaaggtt      5220
actctaaaaa agtgttcggt caaataaaag atctaccaat ggtaatggtt atgttatatg      5280
cctctttagg ttcggtttta ttaagagaat ttggattaca gcccttatt gtagaaatat       5340
caggtagtac atctacaggt aaaacattca cactcaactt agtatcaagt gtttggggaa      5400
cgagcgacct tatcacgaca tggagttcta ctcaaaatag tattgaatcg atggcatcat      5460
ttttgaactc atttccaatg tttaaagatg atacacgtaa tacacatcct aagtttgtta      5520
ccagtgccac atataacttt tctagtggtg aaagtaaatc aagaagtaat attaatttaa      5580
cactaaacgc taaaaagaa tggcgaaata ttttaatttc tactggtgaa tcatctatcg       5640
caaatatggc tgatgaaaaa gcgggtgtat cagcacgtgt agttcactta caagatccac      5700
catatccaga taattttgat tttaccacat tagacaaatc gtttagggag aactatggaa      5760
cgttagggtt ggcatttatt aaacaatatg agtctaaaaa agacgtgtat aagaacgctt      5820
ttgagagcta tcaacggtat tttaatcaaa aaggtagtaa tgaaatcatg caacgtttag      5880
gacgtgcctt tgcgttacta caagttaccg gtgaggtttt gaatgatatt gatgggtttg      5940
aacatgacca ttttaaaatt atcgaacaag cctatgacag catggttaaa acaataaga       6000
cgattgataa acctaagcaa ctgttagagg aactattaca atatttagat gcaaatagaa      6060
ataatatcgc tggtgatggc tatagttcag tcaaaaatgg tgacatcaaa gctatatata      6120
aacgtgatta tttatgtata ttaggtcaaa ctgtacacga taaattaggt catgaaatgc      6180
agactataac aggtcaatgg ggcaaaaaag gatatttaat taaaggtgaa aaagatcgct      6240
tgcaaaaaaa ggtgagtcac aaaaacatta agtatagagg atttgctata aacaaagaaa      6300
tgcttgaaga attaggattt gatttctcga attctcataa tccttattca gattattaaa      6360
tagttcccaa agttcccgat aagttcccgc gaaaaacata caaacgggaa ctataagact      6420
actttaacca caagcaatta agttaatag ttcccgaagt tcccaataaa taatattatt        6480
atttattatt tgaaaacgaa caaatgttgt tagctttata ccatatatga tagaaaattt      6540
ttaacgggta caacgggaac taagtttatt taaagtttat atatcaatgg tttgactagt      6600
tcccgataag tattttaagt cgggaattca acggggacta gttcccattt aaaaatattg      6660
gaggtaacac atggataaag agcaacttaa aaagtatata tacgattatg taaaagaata      6720
taaggagata ccgatatatc agttagaaga tttgtttaaa gaaatgaatc acgactatat      6780
agggagaacc agtgtcacac acgataagga tgagaatatt gtgttttgga gtggatggaa      6840
caaaattaca atgtttgcgc tgattgaatt agttaaaagt gaacaacttg atttagtgta      6900
tagaggtagt tttgtaatgc gttatttgtt ggatggtaga gttcctaact taccattagc      6960
aatttgttat ccagaagatg gacaacaaac ggacgtgccc tcatgggtgc ctatggtatt      7020
aagaataaat aaagaggaga aaatcaaatg aacatagaaa ctatcgtaaa ccaatttgaa      7080
acacgagcag gcacgttact aaggtactac acaggattat tagaacatag taaagtgcaa      7140
ccatgttgct ttaagttata caatgatcca tttgatatgg catacgtgat gatgaatggg      7200
aagttattcg gtcatgtata tattaaagat tgtaaagtaa ggcaatcatt tgaattagcg      7260
tcacctaagc acactgaggg gcttataaga agtatagaag gtcattatgt aggttatgaa      7320
ttacatgacg gtaaacagct ttctattagt gatatgatgg ccagtcaatt atttgaagat      7380
gagtatttta tgtatggatt acaaacatat gcagaatcaa ataatagtga tgtgtttgag      7440
tacctagaaa atggatttga taccgataca cttgagggca ttcaatcgag taatactgat      7500
gtgatagcga atattgaaat gttgtatcag ttagctacag gaatcaatga accagcacca      7560
```

```
gagttagttg aggggttgag attagtaact gagtttgtac aagatgagaa tgcgacacaa    7620
gaggattaca aggctttaga gcataagtta actgagttga agtcatctta ttacagtttg    7680
aataagtaat taaatatgga gtctcacgtg gtgtgtggct cctaatataa agtataagg     7740 tatagaagtt ttaaaatgta aaggttgcaa caatagtgag ttaatagata ggtaggcgaa    7800
attcaaaaaa gtgtgaaatg ttgatattga gctgttttat ggctttgaaa ataataaggt    7860
tatataaagg tgttagcttt taacatcgga aggtatacag tctttgagaa ttgaaaaaat    7920
ggcaagattt gtgcaaggtg tgagaacttt gttaacgcta atacaagcta agtttgtgt    7980 ttttggcata ggcctaaaag ttaagtttgt tcgctgtttg ttcgtgttat tttatcgaac    8040
ttaagttcta tattaggtta atgtgaaaag cctaacgtta agtttataac atgattttat    8100
aagtgttata tatgataagc taaacaattg ataaaacgcg ctataaagcg aacgtaagtt    8160
tgttttagac ctgtaaaaat ggtataattt aggtatgaaa taattaaaag aaagaggtgt    8220
agaaatgcaa agtatcaatt tagctaagca aaacaggatt attaaatagc aatgattgcc    8280
tatccaattc gggtaggctc tgtttatagg ggtgaataaa tgaaactgct taaaacgaag    8340
aattgtttat attatcgtaa tggcgacaat aaactatctg agtatcaact attaacgcaa    8400
tttaacccag catttattaa taaaaaaatt aagatgtgtg aattccaaat tgaaagtatg    8460
taccatatga gtgcgtcgac cacaacatgt gatgaaataa tggggtcgt gtctgtctca     8520 tatccgattg aaaaattagt tatcaaaatt attgaaacaa agcagggtt acaaaactat     8580 aaaaatagat ctataaataa tatggcgttg ttgaaaaagg tactaaatca ttatacagaa    8640
aaagagcaga agcaagttgt aaaatatatg cgttcaaatg gacgatataa gccttacaac    8700
gtcattgaac gcttacaagt tgatttgtat caagcaagta ttaaacaacg ttcagaacgt    8760
caaaaacaaa gaaatacagc aattgaaaac agtaagatta cacgagtaaa tgcatatcac    8820
caatcttcat atgtaaaagt ggtgtaacaa tggataaaaa gcaaataaaa gacttcgttt    8880
gtgattatca taagcgaact agaagtgatg tgttgataga tgatgaaata aataccgatg    8940
aattcttttc aataggtgat gaaaattcta atgaatggat ggcagacgat aacattgatg    9000
atcatattgt aaagaatcac ttagaaatga ttgttgacca agtagctaat gacaaagagt    9060
tttatatttt cgattcttta atacaaggac gtagttttaa agatattagc aatgtcttag    9120
agtgttcaga acaatctgta agattatggt atgaaacctt attagataaa attgtggagg    9180
tgatagaatg agtgagttaa cggcaaaaca agcgcgtttt gtgaatgagt atataagaac    9240
acttaatgta acacaaagtg ccataaaagc aggctatagc gcaaatagtg cacatgtgac    9300
aggatgtagg ttattaaaga agccacacat caagcaatat atacaagaac aaaaagataa    9360
gattatagat gagaatgtat taaccgcaaa agagttacta catgtgctta cgaatgcggc    9420
agtcggtgat gagacagaaa cgaaagaagt tgtagtcaag cgaggggaat ataaagagaa    9480
tccacaaagt ggcaaagtac agctagtcta taacgaacat gttgaactga tagaggtacc    9540
aataaaacct agtgatcgtt taaaagctcg tgatatgttg ggtaaatacc ataagttatt    9600
tacagataag catgatatta acgggaatgt gcctatattc attaatattg gtgaatggga    9660
tggcgatgat gaagatttag ataagacggt acaagaggta tctaacgcta atcctaatca    9720
tactgtgatt gtggatgata taccgttaga ggattgatta cagtaaaaac gattatcata    9780
ttgagttagt gaggattagt ttactaattc accctagctt tatattaaag cgttataaag    9840
ataaaaggga gaacgcttat tataattaac ggactcccct tattaataat tattacagaa    9900
```

```
aaagtggtaa actgcagacg gatcaagaaa caaaggcaac ccaaatctcg caatttgagt     9960
tgatattaga aaaacaagat aattggaaga ttgtaaaata acaaatattg gtacatgatt    10020
acagatactt tgtaatcatg tactcttttt gataaaaaat tggagattcc tttacaaata    10080
tgctcttacg tgctattatt taagtgacta tttaaaagga gttaataaat atgcggcaag    10140
gtattcttaa ataaactgtc aatttgatag cgggaacaaa taattagatg tccttttta    10200 ggagggctta gttttttgta cccagtttaa gaatacctt atcatgtgat tctaaagtat    10260
ccagagaata tctgtatgct ttgtatacct atggttatgc ataaaaatcc cagtgataaa    10320
agtatttatc actgggattt ttatgcccctt tgggttttt gaatggagga aaatcacatg    10380
aaaattatta atattggagt tttagctcat gttgatgcag gaaaaactac cttaacagaa    10440
agcttattat ataacagtgg agcgattaca gaattaggaa gcgtggacaa aggtacaacg    10500
aggacggata atacgctttt agaacgtcag agaggaatta caattcagac aggaataacc    10560
tcttttcagt gggaaaatac gaaggtgaac atcatagaca cgccaggaca tatggatttc    10620
ttagcagaag tatatcgttc attatcagtt ttagatgggg caattctact gatttctgca    10680
aaagatggcg tacaagcaca aactcgtata ttatttcatg cacttaggaa atgggggatt    10740
cccacaatct tttttatcaa taagattgac caaaatggaa ttgatttatc aacggtttat    10800
caggatatta aagagaaact ttctgccgaa attgtaatca aacagaaggt agaactgtat    10860
cctaatatgt gtgtgacgaa ctttaccgaa tctgaacaat gggatacggt aatagaggga    10920
aacgatgacc ttttagagaa atatatgtcc ggtaaatcat tagaagcatt ggaactcgaa    10980
caagaggaaa gcataagatt tcagaattgt tctctgttcc ctctttatca tggaagtgca    11040
aaaagtaata tagggattga taaccttata gaagttatta ctaataaatt ttattcatca    11100
acacatcgag gtccgtctga actttgcgga aatgttttca aaattgaata tacaaaaaaa    11160
agacaacgtc ttgcatatat acgcctttat agtggagtac tacatttacg agattcggtt    11220
agagtatcag aaaaagaaaa aataaaagtt acagaaatgt atacttcaat aaatggtgaa    11280
ttatgtaaga ttgatagagc ttattctgga gaaattgtta ttttgcaaaa tgagtttttg    11340
aagttaaata gtgttcttgg agatacaaaa ctattgccac agagaaaaaa gattgaaaat    11400 ccgcacccctc tactacaaac aactgttgaa ccgagtaaac ctgaacagag agaaatgttg    11460
cttgatgccc ttttggaaat ctcagatagt gatccgcttc tacgatatta cgtggattct    11520
acgacacatg aaattatact ttctttctta gggaaagtac aaatggaagt gattagtgca    11580
ctgttgcaag aaaagtatca tgtggagata gaactaaaag agcctacagt catttatatg    11640
gagagaccgt taaaaaatgc agaatatacc attcacatcg aagtgccgcc aaatccttc    11700 tgggcttcca ttggtttatc tgtatcaccg cttccgttgg gaagtggaat gcagtatgag    11760
agctcggttt ctcttggata cttaaatcaa tcatttcaaa atgcagttat ggaagggata    11820
cgctatggtt gcgaacaagg attatatggt tggaatgtga cggattgtaa aatctgtttt    11880
aagtacggtt tatactatag ccctgttagt actccagcag attttcggat gcttactcct    11940
attgtactgg agcaagcctt tagaaaagct ggaacagaat tgttagagcc atatcttagt    12000
tttaaagttt atgcaccaca ggaatatctt tcacgggcat ataacgatgc tcccaaatat    12060
tgtgcaaata tcgtaaatac tcaactgaaa aataatgagg tcattattat tggagaaatt    12120
cctgctcgat gtattcaaga ttatcgcaat gatttaactt ttttttacaaa tgggcttagt    12180 gtttgtttag cagagctaaa aggatatcag gttaccactg gcgaacctgt ttgccagacc    12240
cgtcgtctaa atagtcggat agataaagta agatatatgt tcaataaaat aacttagtgc    12300
```

```
gttttatgtt gttatataaa tatggtttct tattaaataa gatgaaatat tctttaatat   12360
agatttgaat taaagtggaa aggaggagat tgttattata aactacaagt ggatattgtg   12420
tcctatttgt ggaaataaaa caagactacg aatacgagtg gatactatac ttaaaaattt   12480 cccttatac tgccccaaat gtaagaacga aactttaatt aatgttcaaa aaatgaatat    12540
aataacaatc aaagagccag acgccaagac gcagagccga aatttgaga atgaaactc     12600 tcatcttatc ggctctttt gtttatctga attttactga ctagccttca atatttcttg   12660
cttcattgat acctttgct agtgcttcca ttaaggatag ttctttgtct gtaaagctat    12720
ccatgtattt ttctacctgt aaccttcgag tgctttaat caaattatct gtaggtaaga    12780
aaaattcatc aatagataca tggagtaatg atacaagatc ccctaaggaa ttatctaaaa   12840
cttcactatt tgtactcgag cctttttaa aagtcaatat tactgtaaca taaatatata    12900 tttaaaaat atcccacttt atccaatttt cgtttgaact caacaagtct cagtgtgctg    12960 aagtttggg accattcaaa acagcatagc tctaaaacga gaccttgag cttccgagac     13020 tggtctcagt tttgggacca ttcaaaacag catagctcta aaacctcgta gactattttt   13080
gtctaaaaaa tttcgtaatc gcactatttg tctcagctag acttcagtct tgaaaagccc   13140
ctgtattact gcatttatta agagtattat accatatttt tagttattaa gaaataatct   13200
tcatctaaaa tatacttcag tcacctccta gctgactcaa atcaatgcgt gtttcataaa   13260
gaccagtgat ggattgatgg ataagagtgg catctaaaac ttcttttgta gacgtatatc   13320
gtttacgatc aattgttgta tcaaaatatt taaaagcagc gggagctcca agattcgtca   13380
acgtaaataa atgaataata ttttctgctt gttcacgtat tggttttgtct ctatgtttgt   13440 tatatgcact aagaactta tctaaattgg catctgctaa aataacacgc ttagaaaatt     13500 cactgattg ctcaataatc tcatctaaat aatgcttatg ctgctccaca aacaattgtt    13560
tttgttcgtt atcttctgga ctacccttca acttttcata atgactagct aaatataaaa   13620
aattcacata tttgcttggc agagccagct catttccttt ttgtaattct ccggcactag   13680
ccagcatccg tttacgaccg ttttctaact caaaaagact atatttaggt agtttaatga   13740
ttaagtcttt tttaacttcc ttatatccctt tagcttctaa aaagtcaatc ggatttttt    13800 caaaggaact tctttccata attgtgatcc ctagtaactc tttaacggat tttaacttct   13860
tcgatttccc ttttttccacc ttagcaacca ctaggactga ataagctacc gttggactat   13920
caaaaccacc atattttttt ggatcccagt ctttttacg agcaataagc ttgtccgaat    13980
ttctttttgg taaaattgac tccttggaga atccgcctgt ctgtacttct gttttcttga   14040
caatattgac ttggggcatg acaatacttt tgcgcactgt ggcaaaatct cgccctttat   14100
cccagacaat ttctccagtt tccccattag tttcgattag agggcgtttg cgaatctctc   14160
catttgcaag tgtaatttct gttttgaaga agttcatgat attagagtaa aagaaatatt   14220
ttgcggttgc tttgcctatt tcttgctcag acttagcaat cattttacga acatcataaa   14280
ctttataatc accatagaca aactccgatt caagttttgg atatttctta atcaaagcag   14340
ttccaacgac ggcatttaga tacgcatcat gggcatgatg gtaattgtta atctcacgta   14400
ctttatagaa ttggaaatct tttcggaagt cagaaactaa tttagatttt aaggtaatca   14460
ctttaacctc tcgaataagt ttatcatttt catcgtatt agtattcatg cgactatcca     14520
aaatttgtgc cacatgctta gtgatttggc gagtttcaac caattggcgt ttgataaaac   14580
cagctttatc aagttcactc aaacctccac gttcagcttt cgttaaatta tcaaacttac   14640
```

```
gttgagtgat taacttggcg tttagaagtt gtctccaata gttttttcatc ttttttgacta   14700 cttcttcact tggaacgtta tccgatttac cacgattttt atcagaacgc gttaagacct   14760
tattgtctat tgaatcgtct ttaaggaaac tttgtggaac aatgtgatcg acatcataat   14820
cacttaaacg attaatatct aattcttggt ccacatacat gtctcttcca ttttggagat   14880
aatagagata gagcttttca ttttgcaatt gagtattttc aacaggatgc tctttaagaa   14940
tctgacttcc taattctttg ataccttctt cgattcgttt catacgctct cgcgaatttt   15000
tctgcccctt ttgagttgtc tgattttcac gtgccatttc aataacgata ttttctggct   15060
tatgccgccc cattactttg accaattcat caacaacttt tacagtctgt aaaataccctt  15120 ttttaatagc agggctacca gctaaatttg caatatgttc atgtaaacta tcgccttgtc   15180
cagacacttg tgcttttgtga atgtcttctt taaatgtcaa actatcatca tggatcagct  15240
gcataaaatt gcgattggca aaccatctg atttcaaaaa atctaatatt gttttgccag   15300
attgcttatc cctaatacca ttaatcaatt ttcgagacaa acgtccccaa ccagtataac   15360
ggcgacgttt aagctgtttc atcacctttat catcaaagag gtgagcatat gttttaagtc   15420
tttcctcaat catctccccta tcttcaaata aggtcaatgt taaaacaata tcctctaaga   15480
tatcttcatt ttcttcatta tccaaaaaat ctttatctttt aataattttt agcaaatcat   15540
ggtaggtacc taatgaagca ttaaatctat cttcaactcc tgaaatttca acactatcaa   15600
aacattctat ttttttgaaa taatcttctt ttaattgctt aacggttact tttcgatttg   15660
ttttgaagag taaatcaaca atggctttct tctgttcacc tgaaagaaat gctggttttc   15720
gcattccttc agtaacatat ttgacctttg tcaattcgtt ataaaccgta aaatactcat   15780
aaagcaaact atgttttggt agtacttttt catttggaag atttttatca aagtttgtca   15840
tgcgttcaat aaatgattga gctgaagcac ctttatcgac aacttcttca aaattccatg   15900
gggtaattgt tcttcagac ttccgagtca tccatgcaaa acgactattg ccacgcgcca   15960
atggaccaac ataataagga attcgaaaag tcaagatttt ttcaatcttc tcacgattgt   16020
cttttaaaaa tggataaaag tcttcttgtc ttctcaaaat agcatgcagc tcacccaagt   16080 gaattttgatg gggaatagag ccgttgtcaa aggtccgttg cttgcgcagc aaatcttcac   16140
gatttagttt caccaataat tcctcagtac catccattttt ttctaaaatt ggtttgataa   16200
atttataaaa ttcttcttgg ctagctcccc catcaatata acctgcatat ccgtttttttg  16260 attgatcaaa aaagatttct ttatactttt ctggaagttg ttgtcgaact aaagctttta   16320
aaagagtcaa gtcttgatga tgttcatcgt agcgtttaat cattgaagct gataggggag   16380
ccttagttat ttcagtattt actcttagga tatctgaaag taaaatagca tctgataaat   16440
tcttagctgc caaaaacaaa tcagcatatt gatctccaat ttgcgccaat aaattatcta   16500
aatcatcatc gtaagtatct tttgaaagct gtaatttagc atcttctgcc aaatcaaaat   16560
ttgatttaaa attaggggtc aaacccaatg acaaagcaat gagattccca ataagccat   16620 ttttcttctc accggggagc tgagcaatga gattttctaa tcgtcttgat ttactcaatc   16680
gtgcagaaag aatcgcttta gcatctactc cacttgcgtt aatagggttt tcttcaaata   16740
attgattgta ggtttgtacc aactggataa atagttgtc cacatcacta ttatcaggat   16800
ttaaatctcc ctcaatcaaa aaatgaccac gaaacttaat catatgcgct aaggccaaat   16860
agattaagcg caaatccgct ttatcagtag aatctaccaa tttttttttcgc agatgataga  16920 tagttggata tttctcatga taagcaactt catctactat atttccaaaa ataggatgac   16980
gttcatgctt cttgtcttct tccaccaaaa aagactcttc aagtcgatga aagaaactat   17040
```

```
catctacttt cgccatctca tttgaaaaaa tctcctgtag ataacaaata cgattcttcc    17100
gacgtgtata ccttctacga gctgtccgtt tgagacgagt cgcttccgct gtctctccac    17160
tgtcaaataa aagagcccct ataagatttt ttttgatact gtggcggtct gtatttccca    17220
gaaccttgaa cttttagac ggaaccttat attcatcagt gatcaccgcc catccgacgc     17280
tatttgtgcc gatatctaag cctattgagt atttcttatc cattttgcc tcctaaaata     17340 aaaagtttaa attaaatcca taatgagttt gatgatttca ataatagttt taatgacctc    17400
cgaaattagt ttaatatgct ttaattttc ttttcaaaa tatctcttca aaaatatta      17460 cccaatactt aataataaat agattataac acaaaattct tttaaaaagt agtttatttt    17520
gttatcattc tatagtatta agtattgttt tatggctgat aaatttcttt gaatttctcc    17580
ttgattattt gttataaaag ttataaaata atcttgttgg aaccattcaa acagcatag     17640 caagttaaaa taaggctagt ccgttatcaa cttgaaaaag tggcaccgag tcggtgcttt    17700
ttttgatact tctattctac tctgactgca aaccaaaaaa acaagcgctt tcaaaacgct    17760
tgttttatca tttttaggga aattaatctc ttaatccttt tatcattcta catttaggcg    17820
ctgccatctt gctaaaccta ctaagctcca caggatgatt tcgtaaacta tcataaagaa    17880
aaggaaacag ctgcagataa gcattatatt gcaatgaaaa agcattatat ggataatcat    17940
atctatcatt gcaaatatac ttatagagat ttatgtgtgt gataattggt ggtcataaat    18000
tggtcataat gaaataaaaa aactaaaaaa attgaatgca taagaatac acgatgctga     18060 tttaatagga tttttgtata tgatttatat ctatttcata ctgcccttaa tgccaggaat    18120
gatgtaaaat                                                          18130

<210> SEQ ID NO 4
<211> LENGTH: 15388
<212> TYPE: DNA
<213> ORGANISM: artificial sequence
<220> FEATURE:
<223> OTHER INFORMATION: ABD2009 with lysostaphin insert

<400> SEQUENCE: 4
atgccaggaa tgatgtaaaa tgactgttaa acgccgattt tataacgttt gtaatattgg      60
gtggtcataa tttggtcata gaaattttaa aataaatctt ttgagacgtt ttccatgagt     120 ttactaaaact tttgagaagc gtcttttttg tatgagttcg taatcttagc gtagatgttc    180
atagtggtat ttatatcttt atggcgcaag cgttcttgta tttccttaat atgcacacca    240
gcctctataa gtaacgcaca atgagtatga cgaaatgaat gagtgcttat ttgttttatta   300 gttatgtcag tctttttaag tatagctttt atccataatt gtagttttt aattacaaga     360 gggtagccgt taacatcagt aaaaacgaaa ttattatcta catacaattc gttttcccat    420
gtgtcctgca cgtcggtttt ataattttta agtaatttaa tcacatgagg atccactgaa    480 attttccga ttgagctttc agttttggt gtaagtattt gaaattgctt tttattgtta      540
ttcggattgt aataagtctt tgtaatattg attgtgttat tctcaaagtc tatatcagac    600
catttcaatg ccaataattc acctgcacgc atgcctgtat atgctaatgt acaaaacacc    660
tcaaagctgt tttggggtga atggtgattt ttagcaacct ccaggaattg aaataattca    720 tcttttcaa gaaactttt atgtatctca gtatcttcta attcttccac actaatttc        780 tttttaggtc gtttaatacc ctcgctaggc attattctta ttaatttcat atcgtatgcg    840
tacttaaata tcatatttgt agaggctata atgctatcaa cataattctt gctatactgt    900
```

```
gcgcttatat cgtttacaaa acgttgatat tcatgtttat tgatagtttg tattggttta    960
ttgttaaagc gttctatggc gtggtttatg gctttctcgc gtgctctgac actacttact   1020
tttacttcgt tagcatattg tgatatccaa tcgtcagcaa cctgtttaaa tgtagatgtg   1080
gacggtgcga tataatcgcc atttcttaac tgacgctcaa ccatttcagc gtgatgttta   1140
gcgtctgatt tgcgttttaaa acctgagttt gaaatatatt tatatttgcc cgtttctgcg   1200
tcttttccta gtgatatacg atagcgccat gtatttccgc gttttcata acttgccatt   1260
tgatcacctc gattaatatt ctttaaaaat atcactagat aaacggctat cagtttgtaa   1320
aatttcttta tgtagagtcg tactttttttc gcctttattt ggaaaaagct cttcaatatc   1380
gtctatattt tttactatta tttcagaaac atacccactt aacttttggt taatttttttt   1440
aaataacaag ttttttaaggc ctgcagataa actatcaacg tattttttta atccgatatt   1500
ttcatcttca tttttaatcg tgaaaataaa tctatgttgt gaattagtta tcttttcagt   1560
ttctttatat gagacgtcta agtcaaaatt taatttttgc ctattatcta attcgacgtc   1620
tactaaaatt tcaaagtcaa aatttttcaat cgaaaaagcg tgagtaatgt ttgcagttac   1680
ttcaaatccc tcgaaaacat cattaatttt ataattcggt tcttcatcaa agtaaagtc   1740
aaaattgatc ggattatgtt caaaaaattc tgaaggagat atgtgcagat aactacataa   1800
tttatctata gcatcatatc ttatcatttc agaatcattt tgtgccattg aagtaagtga   1860
acttcttgct atttttacat cttttgcaac acgagatatt tttagtcctc tttctgacag   1920
tagttcagac aatctatttc taatcattac aaacctccta attatgttaa taatagcatt   1980
ttttttggacg tttatgtaca aaaaaataaa aaatgattga gaagtcagtc gaaaaactat   2040
tgcaaaagaa aaacgattat gtaataaaa gttataaatt gattgagaag tcagtcaaaa   2100
acgaaggagg atttttaatta tgactatttt agcgaatact agaaagttta agaagccat   2160
gttcttaaaa ggctttaatt tatctgatttt atcacgtgaa acaggtgttg gaatttctta   2220
tttaagccaa attattaatg gtaaaaagat tccaagccct aaattagcta gaaaatggc   2280
agaagtttta caagttgagg taaatgaatt atttgaattt gaagtaaagg aggcataaac   2340
caatgttcaa cattaatatt gatgaagatg aagcacgtga gttacttgag caggctatca   2400
atgcacgtgt ggacgaatta gcgaaagaga atatttttat gacttacaaa gagttgtcta   2460
actatctgaa tttaagtaag cctactattg aagaattact tattaataat ggcatgaaat   2520
attatatggt cggatctacg tacagattca aaaagtctga tgtagatgaa ttcatggaac   2580
agcttactgc tcatatgaat atccagaata acgactttaa acaagtcaat atcaaaaagt   2640
tattggaggc aaggcaatga aaatctactt aacttatatc tgcttagttt cattgttaac   2700
aatattatta ctagcaatat ctaacatgta tgttgctttt agcgtttatg cttggctaat   2760
aactttagga tgtaatttaa caggagagat tacaacgtgc gaaaacaagt gattattaca   2820
aaaacagtag ttggctggta caacattaaa gatactcaac ataatttaat gttaaatata   2880
ccgccaaaag tatttgaaca gtactttcct gatgttagta agatgttca gttgtgtgt   2940
ttagaaatgg attttatcaaa aattacagaa attaaaaata agaaaaagt aggtagttaa   3000
gatgggaatc aaacaaaaat atcaattatc aaaagtggtt aaaatattag aagtagtatt   3060
atacgaggaa gataagtttc aatccgataa ggactatcat tatcaggata aagcattata   3120
tgaatatgct ttaaagttag ttcataatgg attgttcaat attcttgctg aattagtttt   3180
tgaagatgaa gcatttttaa ttcttgatga agtaacaatg acgctaagtg atgtcatgaa   3240
agaaacacaa cacgtttacc gttatagtgt catagatgaa aaaggtgaac acaaacatac   3300
```

```
aacagatcgc aaaggacacg tgattggaat gttagagtgg gcattagatt acattgcggg    3360
aaatattgaa gtggaggaat tataaatgaa ttgggaaatt aaagatttaa tgtgtgatat    3420
tgaagcggta aaagaaaaaa tcaatgatgt agctatcaaa catgcttggt ttgttgaaga    3480
tagatttgta aaaaatgaat tagaaacaaa acgggaacat attaattttt ctgctagcta    3540
tttagaacat cgtatacaaa atgaacatac agttgagtta ttacatgtgt acttaaaaga    3600
attcggtgaa cttatacaaa aatttcatga atagaaaaa gcatcatctg agaactttgg    3660
cgaggtatca gatgacgcac aaaaattaaa aatcacagag taatttagaa attacacatg    3720
tttattataa cattttttac tctgtgaatc actagaggtg caaaaaatga atgaaattaa    3780
attagaatat gacacacatg tttcagtggt acattatgaa agtttagact cacgttcatt    3840
taatagcttt tcaaaaatta attggagtaa gttggttaat aaactgtctg tacctataga    3900
agcaaattat aagtatgcac gtggtgttgc tgtttacggt gatattaaaa acggtgcaaa    3960
tgatcaaggt gaaattatca aaagcatcg aaacgataaa aatgtcatat acagagatgt    4020
gattgtactt gattatgatg aaataaatga tttaaagcaa ttacatgaag caatcagctc    4080
agctttaagc aatgttgcat ggttttggca cacaagttac tcgcacagaa ctgaacaagc    4140
tagaatacgc ctgtatatcc ctctaaatga gcgaataagt gcagatgatt atcgtaaata    4200
tacaaaagta ttagcaaata aaattggcca taaagtggat gaaggttcat atcagccaag    4260
tagatgtttt gcgttaccag ttattcaaaa aggacacata tttattaagc gagtgaatga    4320
ctgtccaatt atgaatgttg atatgctcga acagtggtcg aaggagtttg aacaatcaaa    4380
tgctagtcct aatgtcatag gatacactcg acgcgatagt gagtactggc gcgagctatg    4440
ctttggaaca accgaaggca atcgtaacaa tgcactagct agcttaattg ggcatttatt    4500
aagatgtcac gttaatgatt atattgttta ttcatttgct ttactatggg ggcaattcgc    4560
atgtaaacca cctatgaaag aacaagaaat caacgccact tttcaatcga tattaaataa    4620
acactataac aattagaaag gggctttgta tggaaacagg taaaagtgat gtacttgata    4680
aaattgaaaa aattaataaa aaagatagtg ccttacaaga aattatacca aaaggttatg    4740
aaattgaaca tcatcaatgc ggtattgcct taaatcaact tataccaagt aaaaaagaag    4800
gcgagccaga taaaaaggtt tttatcacaa gtacaatccc tcaaatcact gaacgctttg    4860
aagatattga gagtaacgaa gtcagcttta atatgctttt ctatgacaat aaaacgccag    4920
taaatatagc tgtgagtgcc gaagaaattt cagatagtcg tcaactcttg aaattggtta    4980
ataaaaagct ggatgtaaca tcgtcgacat ctactaaact tgttgattat attaatgcat    5040
ctaaacggta taatccacca ttgaatgtta aagttgcaac gcgtttgggg catgtgaaag    5100
gttattttat ttatccttat caagaagtga tgaaagacag caatatcaag ttgtttagta    5160
atgataaagg atttcaaaag ttaatagact cttttcaaag caaggaaca ttagaaggtt    5220
actctaaaaa agtgttcggt caaataaaag atctaccaat ggtaatggtt atgttatatg    5280
cctctttagg ttcggtttta ttaagagaat ttggattaca gcccttttatt gtagaaatat    5340
caggtagtac atctacaggt aaaacattca cactcaactt agtatcaagt gtttggggaa    5400
cgagcgacct tatcacgaca tggagttcta ctcaaaatag tattgaatcg atggcatcat    5460
ttttgaactc atttccaatg tttaaagatg atacacgtaa tacacatcct aagtttgtta    5520
ccagtgccac atataacttt tctagtggtg aaagtaaatc aagaagtaat attaatttaa    5580
cactaaacgc taaaaagaa tggcgaaata ttttaatttc tactggtgaa tcatctatcg    5640
```

```
caaatatggc tgatgaaaaa gcgggtgtat cagcacgtgt agttacacta caagatccac    5700
catatccaga taattttgat tttaccacat tagacaaatc gtttagggag aactatggaa    5760
cgttagggtt ggcatttatt aaacaatatg agtctaaaaa agacgtgtat aagaacgctt    5820
ttgagagcta tcaacggtat tttaatcaaa aaggtagtaa tgaaatcatg caacgtttag    5880
gacgtgcctt tgcgttacta caagttaccg gtgaggtttt gaatgatatt gatgggtttg    5940
aacatgacca ttttaaaatt atcgaacaag cctatgacag catggttaaa aacaataaga    6000
cgattgataa acctaagcaa ctgttagagg aactattaca atatttagat gcaaatagaa    6060
ataatatcgc tggtgatggc tatagttcag tcaaaaatgg tgacatcaaa gctatatata    6120
aacgtgatta tttatgtata ttaggtcaaa ctgtacacga taaattaggt catgaaatgc    6180
agactataac aggtcaatgg ggcaaaaaag gatatttaat taaaggtgaa aaagatcgct    6240
tgcaaaaaaa ggtgagtcac aaaaacatta agtatagagg atttgctata aacaaagaaa    6300
tgcttgaaga attaggattt gatttctcga attctcataa tccttattca gattattaaa    6360
tagttcccaa agttcccgat aagttcccgc gaaaaacata caaacgggaa ctataagact    6420
actttaacca caagcaatta aagttaatag ttcccgaagt tcccaataaa taatattatt    6480
atttattatt tgaaaacgaa caaatgttgt tagctttata ccatatatga tagaaaattt    6540
ttaacgggta caacgggaac taagtttatt taaagtttat atatcaatgg tttgactagt    6600
tcccgataag tattttaagt cgggaattca acggggacta gttcccattt aaaaatattg    6660
gaggtaacac atggataaag agcaacttaa aaagtatata tacgattatg taaaagaata    6720
taaggagata ccgatatatc agttagaaga tttgtttaaa gaaatgaatc acgactatat    6780
agggagaacc agtgtcacac acgataagga tgagaatatt gtgttttgga gtggatggaa    6840
caaaattaca atgtttgcgc tgattgaatt agttaaaagt gaacaacttg atttagtgta    6900
tagaggtagt tttgtaatgc gttatttgtt ggatggtaga gttcctaact taccattagc    6960
aatttgttat ccagaagatg gacaacaaac ggacgtgccc tcatgggtgc ctatggtatt    7020
aagaataaat aaagaggaga aaatcaaatg aacatagaaa ctatcgtaaa ccaatttgaa    7080
acacgagcag gcacgttact aaggtactac acaggattat tagaacatag taaagtgcaa    7140
ccatgttgct ttaagttata caatgatcca tttgatatgg catacgtgat gatgaatggg    7200
aagttattcg gtcatgtata tattaaagat tgtaaagtaa ggcaatcatt tgaattagcg    7260
tcacctaagc acactgaggg gcttataaga agtatagaag gtcattatgt aggttatgaa    7320
ttacatgacg gtaaacagct ttctattagt gatatgatgg ccagtcaatt atttgaagat    7380
gagtatttta tgtatggatt acaaacatat gcagaatcaa ataatagtga tgtgtttgag    7440
tacctagaaa atggatttga taccgataca cttgagggca ttcaatcgag taatactgat    7500
gtgatagcga atattgaaat gttgtatcag ttagctacag gaatcaatga accagcacca    7560
gagttagttg aggggttgag attagtaact gagtttgtac aagatgagaa tgcgacacaa    7620
gaggattaca aggctttaga gcataagtta actgagttga agtcatctta ttacagtttg    7680
aataagtaat aaatatgga gtctcacgtg gtgtgtggct cctaatataa agtataagg    7740 tatagaagtt ttaaaatgta aaggttgcaa caatagtgag ttaatagata ggtaggcgaa    7800
attcaaaaaa gtgtgaaatg ttgatattga gctgttttat ggctttgaaa ataataaggt    7860
tatataaagg tgttagcttt taacatcgga aggtatacag tctttgagaa ttgaaaaaat    7920
ggcaagattt gtgcaaggtg tgagaacttt gttaacgcta atacaagcta aagtttgtgt    7980
ttttggcata ggcctaaaag ttaagtttgt tcgctgtttg ttcgtgttat tttatcgaac    8040
```

```
ttaagttcta tattaggtta atgtgaaaag cctaacgtta agtttataac atgattttat    8100
aagtgttata tatgataagc taaacaattg ataaaacgcg ctataaagcg aacgtaagtt    8160
tgttttagac ctgtaaaaat ggtataattt aggtatgaaa taattaaaag aaagaggtgt    8220
agaaatgcaa agtatcaatt tagctaagca aaacaggatt attaaatagc aatgattgcc    8280
tatccaattc gggtaggctc tgtttatagg ggtgaataaa tgaaactgct taaaacgaag    8340
aattgtttat attatcgtaa tggcgacaat aaactatctg agtatcaact attaacgcaa    8400
tttaacccag catttattaa taaaaaaatt aagatgtgtg aattccaaat tgaaagtatg    8460
taccatatga gtgcgtcgac cacaacatgt gatgaaataa tggggggtcgt gtctgtctca    8520
tatccgattg aaaaattagt tatcaaaatt attgaaacaa aagcagggtt acaaaactat    8580
aaaaatagat ctataaataa tatggcgttg ttgaaaaagg tactaaatca ttatacagaa    8640
aaagagcaga agcaagttgt aaaatatatg cgttcaaatg gacgatataa gccttacaac    8700
gtcattgaac gcttacaagt tgatttgtat caagcaagta ttaaacaacg ttcagaacgt    8760
caaaaacaaa gaaatacagc aattgaaaac agtaagattg cacgagtaaa tgcatatcac    8820
caatcttcat atgtaaaagt ggtgtaacaa tggataaaaa gcaaataaaa gacttcgttt    8880
gtgattatca taagcgaact agaagtgatg tgttgataga tgatgaaata aataccgatg    8940
aattcttttc aataggtgat gaaaattcta atgaatggat ggcagacgat aacattgatg    9000
atcatattgt aaagaatcac ttagaaatga ttgttgacca agtagctaat gacaaagagt    9060
tttatatttt cgattcttta atacaaggac gtagttttaa agatattagc aatgtcttag    9120
agtgttcaga acaatctgta agattatggt atgaaaccct attagataaa attgtggagg    9180
tgatagaatg agtgagttaa cggcaaaaca agcgcgtttt gtgaatgagt atataagaac    9240
acttaatgta acacaaagtg ccataaaagc aggctatagc gcaaatagtg cacatgtgac    9300
aggatgtagg ttattaaaga agccacacat caagcaatat atacaagaac aaaaagataa    9360
gattatagat gagaatgtat taaccgcaaa agagttacta catgtgctta cgaatgcggc    9420
agtcggtgat gagacagaaa cgaaagaagt tgtagtcaag cgaggggaat ataaagagaa    9480
tccacaaagt ggcaaagtac agctagtcta taacgaacat gttgaactga tagaggtacc    9540
aataaaacct agtgatcgtt taaaagctcg tgatatgttg ggtaaatacc ataagttatt    9600
tacagataag catgatatta acgggaatgt gcctatattc attaatattg gtgaatggga    9660
tggcgatgat gaagatttag ataagacggt acaagaggta tctaacgcta atcctaatca    9720
tactgtgatt gtggatgata taccgttaga ggattgatta cagtaaaaac gattatcata    9780
ttgagttagt gaggattagt ttactaattc accctagctt tatattaaag cgttataaag    9840
ataaagggga gaacgcttat tataattaac ggactccctt tattaataat tattacagaa    9900
aaagtggtaa attaattaat ttctgcttct atagtttttaa tttcatcaat atttataggt   9960
gggttttcag tattgtattc aaacttttta gataaatcac tttgatatgt ggatccgtca    10020
ttcattgtta ttttccaata accacccgtt ttatcgcttg aacgatataa tccatgtatt    10080
tgagttagct gatgacgaat ttcaaagtct aaagttgata tagctaattg tttttttatcg   10140
aactttggcc aatactttaa ggggctatct ttaccatgaa ccttaacttt taaaggtagt    10200
tctattggag taggtaattt ttcagtattt gtaacgccac ttatttggaa atggatataa    10260
gttccttcgc tagtatgttg gctttttttta gttcttttttg tgtttaagtc aacttttttcc   10320
ccttttgtaa aagcagggct ataataagga ctcggaaaaa ttataaggct gatgctgcca    10380
```

```
tctgtgtttt ttatacgcat agatcctaag acggatcaag aaacaaaggc aacccaaatc    10440
tcgcaatttg agttgatatt agaaaaacaa gataattgga agattgtaaa ataacaaata    10500
ttggtacatg attacagata cttttgtaatc atgtactctt tttgataaaa aattggagat   10560
tcctttacaa atatgctctt acgtgctatt atttaagtga ctatttaaaa ggagttaata    10620
aatatgcggc aaggtattct taaataaact gtcaatttga tagcgggaac aaataattag    10680
atgtcctttt ttaggagggc ttagtttttt gtacccagtt taagaatacc tttatcatgt    10740
gattctaaag tatccagaga atatctgtat gctttgtata cctatggtta tgcataaaaa    10800
tcccagtgat aaaagtattt atcactggga tttttatgcc cttttgggtt tttgaatgga    10860
ggaaaatcac atgaaaatta ttaatattgg agttttagct catgttgatg caggaaaaac    10920
taccttaaca gaaagcttat tatataacag tggagcgatt acagaattag gaagcgtgga    10980
caaaggtaca acgaggacgg ataatacgct tttagaacgt cagagaggaa ttacaattca    11040
gacaggaata acctcttttc agtgggaaaa tacgaaggtg aacatcatag acacgccagg    11100
acatatggat ttcttagcag aagtatatcg ttcattatca gttttagatg gggcaattct    11160
actgatttct gcaaaagatg gcgtacaagc acaaactcgt atattatttc atgcacttag    11220
gaaaatgggg attcccacaa tctttttttat caataagatt gaccaaaatg gaattgatttt   11280 atcaacggtt tatcaggata ttaaagagaa actttctgcc gaaattgtaa tcaaacagaa    11340
ggtagaactg tatcctaata tgtgtgtgac gaactttacc gaatctgaac aatgggatac    11400
ggtaatagag ggaaacgatg accttttaga gaaatatatg tccggtaaat cattagaagc    11460
attggaactc gaacaagagg aaagcataag atttcagaat tgttctctgt tccctctttta    11520 tcatggaagt gcaaaagta atataggggat tgataacctt atagaagtta ttactaataa    11580
attttattca tcaacacatc gaggtccgtc tgaactttgc ggaaatgttt tcaaaattga    11640
atatacaaaa aaaagacaac gtcttgcata tatacgcctt tatagtggag tactacattt    11700
acgagattcg gttagagtat cagaaaaaga aaaaataaaa gttacagaaa tgtatacttc    11760
aataaatggt gaattatgta agattgatag agcttattct ggagaaattg ttattttgca    11820
aaatgagttt tgaagttaa atagtgttct tggagataca aaactattgc cacagagaaa    11880
aaagattgaa aatccgcacc ctctactaca aacaactgtt gaaccgagta aacctgaaca    11940
gagagaaatg ttgcttgatg ccccttttgga aatctcagat agtgatccgc ttctacgata    12000
ttacgtggat tctacgacac atgaaattat actttctttc ttagggaaag tacaaatgga    12060
agtgattagt gcactgttgc aagaaaaagta tcatgtggag atagaactaa aagagcctac    12120
agtcatttat atggagagac cgttaaaaaa tgcagaatat accattcaca tcgaagtgcc    12180
gccaaatcct ttctgggctt ccattggttt atctgtatca ccgcttccgt tgggaagtgg    12240
aatgcagtat gagagctcgg tttctcttgg atacttaaat caatcatttc aaaatgcagt    12300
tatggaaggg atacgctatg gttgcgaaca aggattatat ggttggaatg tgacggattg    12360
taaaatctgt tttaagtacg gtttatacta tagccctgtt agtactccag cagattttcg    12420
gatgcttact cctattgtac tggagcaagc ctttagaaaa gctggaacag aattgttaga    12480
gccatatctt agttttaaag tttatgcacc acaggaatat ctttcacggg catataacga    12540
tgctcccaaa tattgtgcaa atatcgtaaa tactcaactg aaaaataatg aggtcattat    12600
tattggagaa attcctgctc gatgtattca agattatcgc aatgatttaa ctttttttac    12660
aaatgggctt agtgttgtt tagcagagct aaaaggatat caggttacca ctggcgaacc    12720
tgtttgccag acccgtcgtc taaatagtcg gatagataaa gtaagatata tgttcaataa    12780
```

```
aataacttag tgcgttttat gttgttatat aaatatggtt tcttattaaa taagatgaaa    12840
tattctttaa tatagatttg aattaaagtg gaaaggagga gattgttatt ataaactaca    12900
agtggatatt gtgtcctatt tgtggaaata aaacaagact acgaatacga gtggatacta    12960
tacttaaaaa tttcccttta tactgcccca aatgtaagaa cgaaacttta attaatgttc    13020
aaaaaatgaa tataataaca atcaaagagc cagacgccaa gacgcagagc cgataatttg    13080
agaaatgaaa ctctcatctt atcggctctt tttgtttatc tgaattttac tgactagcct    13140
tcaatatttc ttgcttcatt gatacctttt gctagtgctt ccattaagga tagttctttg    13200
tctgtaaagc tatccatgta ttttctacc tgtaaccttc gagtgctttt aatcaaatta    13260
tctgtaggta agaaaaattc atcaatagat acatggagta atgatacaag atcccctaag    13320
gaattatcta aaacttcact atttgtactc gagaagcttc aactttagga atgagaaaaa    13380
atttttattt gctctaatta tcatataagt ttataaaaag cgcgctcact ttatagttcc    13440
ccaaagaaca cctaaagtat tagtagattt attccatgtt cttacaggca agtaaatacg    13500
ttggccactg ttacctgtat aacctaccca acatgaccg tcttgtttca tcacttcatc    13560
ataatgaatt gtttgacctg cttttaagac tcctgactgc ggcatgcttc taaatggacc    13620
agtcgttctt gttattatat ctgtattagg tgtgaagcta gctgactctg atttatatag    13680
tgtgccatat ttgtttgttt tccaacctgt attcggcgtt ggagttactg taccacctgc    13740
ttttccatat cctgcgctct ttaagaaagg cattggatct tgggcagttg aatttgaaaa    13800
tgaattaacc attctttgga agtgtaaatg tggtgctgta gaataaccag tgcttccaga    13860
ccaaccgatt atttgaccag ctttgacata atctcctact ttaacattat atttacttag    13920
atgcatatac cattgtctat gcactccatc attttcaata agacctattt gattacctcc    13980
tccgtaatta ctccaaccag cttcaactat ttttccgctt gaaatagctt ttactggtgt    14040
tccaatattc ataaaaaaat caactccgta gtgcataccg ccatttatac ctaatggata    14100
aggaccgtaa ccatatcctt ttttgtaatt attcaaccat tgtgctgaat gttcatgtgt    14160
tgcagctctt aaagctgttc tattttgaac cagggctttt gaagtctcta cttcagctgt    14220
attttctact ggggcttttg aagtctctac ttcagctgta ttttctaccg gagcttttga    14280
agtctctact tcagctgtat tttctactgg agcttttgaa gtctctactt cagctgtatt    14340
ttctactggg gcttttgaag tctctacttc agctgtattt tctaccggag cttttgaagt    14400
ctctacttca gctgtatttt ctactggagc ttttgaagtc tctacttcag ctgtattttc    14460
tactggggct tttgaagtct ctacttcagc tgtattttct accggagctt ttgaagtctc    14520
tacttcagct gtattttcta ccggagcttt tgaagtctct acttcagctg tattttctac    14580
cggagctttt gaagtctcta cttcagctgt attttctact ggagcttttg aagtctctac    14640
ttcagctgta ttttctactg gagcttttga agtctctact cagctgtat tttctactgg    14700 agcttttgaa gtctctactt cagctgtatt ttctactggg gcttttgaag tctctacttc    14760
agctactttt tttgaaacat ccatattact tttttcagaa gcatgtgttt cattttgaat    14820
ccctccataa acaatagatg ctaaggcaaa tgtactcagt ccaatagcta aggtctcgt    14880 ataataattg ttttttgttt tcttcaacct taatacctcc taatttatta ttacatttat    14940
gagaatagca tatttttata aatattacat ttttttaacga tgaagaaagt aaaataatat    15000
tgattgattt tgatgaaata tacaaacaca ctcaaaaatt gactttaaga ttttttgaaat    15060 tctaactgat tgtgttaaaa taatatgaat caatattaag aaagtaggtt tttttttgga    15120
```

-continued

```
attttcaaaa ctaaacattc aagagttcct gcagataagc attatattgc aatgaaaaag    15180
cattatatgg ataatcatat ctatcattgc aaatatactt atagagattt atgtgtgtga    15240
taattggtgg tcataaattg gtcataatga aataaaaaaa ctaaaaaaat tgaatgcata    15300
aagaatacac gatgctgatt taataggatt tttgtatatg atttatatct atttcatact    15360
gcccttaatg ccaggaatga tgtaaaat                                       15388
```

<210> SEQ ID NO 5
<211> LENGTH: 18
<212> TYPE: DNA
<213> ORGANISM: Staphylococcus aureus subsp. aureus Tager 104

<400> SEQUENCE: 5
aaagaagaac aataatat                                                       18

<210> SEQ ID NO 6
<211> LENGTH: 18
<212> TYPE: DNA
<213> ORGANISM: Staphylococcus epidermidis strain 949_S8

<400> SEQUENCE: 6
aaagaagaac aataatat                                                       18

<210> SEQ ID NO 7
<211> LENGTH: 18
<212> TYPE: DNA
<213> ORGANISM: stapholococcus NY940

<400> SEQUENCE: 7
aaagaagaac aataatat                                                       18

<210> SEQ ID NO 8
<211> LENGTH: 18
<212> TYPE: DNA
<213> ORGANISM: Staphylococcus aureus subsp. aureus strain MRSA252

<400> SEQUENCE: 8
aaagaagaac aataatat                                                       18

<210> SEQ ID NO 9
<211> LENGTH: 18
<212> TYPE: DNA
<213> ORGANISM: Staphylococcus aureus

<400> SEQUENCE: 9
taattattcc cactcaat                                                       18

<210> SEQ ID NO 10
<211> LENGTH: 18
<212> TYPE: DNA
<213> ORGANISM: Staphylococcus aureus V329

<400> SEQUENCE: 10
taattattcc cactcaat                                                       18

<210> SEQ ID NO 11
<211> LENGTH: 18
<212> TYPE: DNA
<213> ORGANISM: Staphylococcus aureus strain BA01611

<400> SEQUENCE: 11
taattattcc cactcaat                                                       18

<210> SEQ ID NO 12
<211> LENGTH: 18
<212> TYPE: DNA
<213> ORGANISM: Staphylococcus aureus strain MCRF184

<400> SEQUENCE: 12
taattattcc cactcaat                                                 18

<210> SEQ ID NO 13
<211> LENGTH: 18
<212> TYPE: DNA
<213> ORGANISM: Staphylococcus aureus strain JP5338

<400> SEQUENCE: 13
taattattcc cactcaat                                                 18

<210> SEQ ID NO 14
<211> LENGTH: 15
<212> TYPE: DNA
<213> ORGANISM: Staphylococcus aureus subsp. aureus MW2 DNA

<400> SEQUENCE: 14
tcccgccgtc tccat                                                    15

<210> SEQ ID NO 15
<211> LENGTH: 15
<212> TYPE: DNA
<213> ORGANISM: Staphylococcus aureus subsp. aureus Mu50

<400> SEQUENCE: 15
tcccgccgtc tccat                                                    15

<210> SEQ ID NO 16
<211> LENGTH: 15
<212> TYPE: DNA
<213> ORGANISM: Staphylococcus epidermidis strain 4S-13

<400> SEQUENCE: 16
tcccgccgtc tccat                                                    15

<210> SEQ ID NO 17
<211> LENGTH: 15
<212> TYPE: DNA
<213> ORGANISM: Staphylococcus aureus strain AUS0325

<400> SEQUENCE: 17
tcccgccgtc tccat                                                    15

<210> SEQ ID NO 18
<211> LENGTH: 17
<212> TYPE: DNA
<213> ORGANISM: Staphylococcus aureus

<400> SEQUENCE: 18
ttatttagca ggaataa                                                  17

<210> SEQ ID NO 19
<211> LENGTH: 17
<212> TYPE: DNA
<213> ORGANISM: Staphylococcus aureus subsp. aureus COL

<400> SEQUENCE: 19

-continued ttatttagca ggaataa                                              17

<210> SEQ ID NO 20
<211> LENGTH: 17
<212> TYPE: DNA
<213> ORGANISM: Staphylococcus aureus strain M92

<400> SEQUENCE: 20
ttatttagca ggaataa                                              17

<210> SEQ ID NO 21
<211> LENGTH: 17
<212> TYPE: DNA
<213> ORGANISM: Staphylococcus aureus strain C2406

<400> SEQUENCE: 21
ttatttagca ggaataa                                              17

<210> SEQ ID NO 22
<211> LENGTH: 17
<212> TYPE: DNA
<213> ORGANISM: Staphylococcus aureus strain JE2

<400> SEQUENCE: 22
ttatttagca ggaataa                                              17

<210> SEQ ID NO 23
<211> LENGTH: 17
<212> TYPE: DNA
<213> ORGANISM: Staphylococcus aureus strain SA40TW

<400> SEQUENCE: 23
ttatttagca ggaataa                                              17

<210> SEQ ID NO 24
<211> LENGTH: 17
<212> TYPE: DNA
<213> ORGANISM: Staphylococcus aureus subsp. aureus strain 2148.C01

<400> SEQUENCE: 24
ttatttagca ggaataa                                              17

<210> SEQ ID NO 25
<211> LENGTH: 17
<212> TYPE: DNA
<213> ORGANISM: Staphylococcus aureus subsp. aureus strain
    USA300_2014.C02

<400> SEQUENCE: 25
ttatttagca ggaataa                                              17

<210> SEQ ID NO 26
<211> LENGTH: 17
<212> TYPE: DNA
<213> ORGANISM: Staphylococcus aureus subsp. aureus strain 5118.N

<400> SEQUENCE: 26
ttatttagca ggaataa                                              17

<210> SEQ ID NO 27
<211> LENGTH: 17
<212> TYPE: DNA
<213> ORGANISM: Staphylococcus aureus

```
<400> SEQUENCE: 27
ttatttagca ggaataa                                                  17

<210> SEQ ID NO 28
<211> LENGTH: 20
<212> TYPE: DNA
<213> ORGANISM: Staphylococcus aureus subsp. aureus N315

<400> SEQUENCE: 28
ttttacatca ttcctggcat                                               20

<210> SEQ ID NO 29
<211> LENGTH: 20
<212> TYPE: DNA
<213> ORGANISM: Staphylococcus aureus RF122

<400> SEQUENCE: 29
ttttacatca ttcctggcat                                               20

<210> SEQ ID NO 30
<211> LENGTH: 20
<212> TYPE: DNA
<213> ORGANISM: Staphylococcus aureus strain: No. 10

<400> SEQUENCE: 30
ttttacatca ttcctggcat                                               20

<210> SEQ ID NO 31
<211> LENGTH: 20
<212> TYPE: DNA
<213> ORGANISM: Staphylococcus aureus strain M92

<400> SEQUENCE: 31
ttttacatca ttcctggcat                                               20

<210> SEQ ID NO 32
<211> LENGTH: 20
<212> TYPE: DNA
<213> ORGANISM: Staphylococcus aureus strain C2406

<400> SEQUENCE: 32
ttttacatca ttcctggcat                                               20

<210> SEQ ID NO 33
<211> LENGTH: 20
<212> TYPE: DNA
<213> ORGANISM: Staphylococcus aureus subsp. aureus strain
     USA300_2014.C02

<400> SEQUENCE: 33
ttttacatca ttcctggcat                                               20

<210> SEQ ID NO 34
<211> LENGTH: 20
<212> TYPE: DNA
<213> ORGANISM: Staphylococcus aureus strain SR434

<400> SEQUENCE: 34
ttttacatca ttcctggcat                                               20

<210> SEQ ID NO 35
<211> LENGTH: 20
<212> TYPE: DNA
```

```
<213> ORGANISM: Staphylococcus aureus strain RN3984

<400> SEQUENCE: 35
ttttacatca ttcctggcat                                                    20

<210> SEQ ID NO 36
<211> LENGTH: 20
<212> TYPE: DNA
<213> ORGANISM: Staphylococcus aureus

<400> SEQUENCE: 36
ttttacatca ttccaggcat                                                    20

<210> SEQ ID NO 37
<211> LENGTH: 17
<212> TYPE: DNA
<213> ORGANISM: Staphylococcus saprophyticus subsp. saprophyticus

<400> SEQUENCE: 37
cgaggggact aataagt                                                       17
```

COMPOSITIONS AND METHODS FOR NON-ANTIBIOTIC TREATING OF BACTERIAL INFECTIONS BY BLOCKING OR DISRUPTING BACTERIAL GENES INVOLVED IN VIRULENCE OR VIABILITY

CROSS REFERENCE TO RELATED APPLICATIONS

This application claims priority to U.S. provisional application Ser. No. 62/506,546, filed May 15, 2017, and to U.S. provisional application Ser. No. 62/543,343, filed Aug. 9, 2017, the disclosures of each of which are incorporated herein by reference.

SEQUENCE LISTING

The instant application contains a Sequence Listing which has been submitted electronically in ASCII format and is hereby incorporated by reference in its entirety. Said ASCII copy, created on Nov. 13, 2019, is named 058636_00233_Sequence_Listing.txt and is 68, 846 bytes in size.

FIELD

The present disclosure relates generally to approaches for attenuating virulence, inhibiting growth of and/or killing bacteria in an infection site as well as in vitro, and more particularly to engineered particles comprising modified bacterial DNA islands.

BACKGROUND

Antibiotic resistance is one of the world's most pressing public health problems. Illnesses that were once easily treatable with antibiotics are becoming more difficult to cure and more expensive to treat. Each year in the United States alone, at least 2 million people become infected with bacteria that are resistant to antibiotics. Genotypic as well as phenotypic antibiotic resistance can arise in a wide variety of bacteria. Of particular concern is that *Staphylococcus aureus* and other staphylococci continue to cause life-threatening infections affecting any bodily organ and, during the past 15 years have become a major cause of community-acquired infections, as well as continuing to be the scourge of the hospital environment. Staphylococci have become increasingly resistant to antibiotics, especially to β-lactams and glycopeptides, and their infections are now, in many cases, totally untreatable. Thus there is an ongoing need for improved compositions and methods for treating bacterial infections. The present disclosure is pertinent to these needs.

SUMMARY

The present disclosure provides compositions and methods for converting bacterial DNA islands into what is referred to herein from time to time herein as "Anti-bacterial Drones" (ABDs), and includes the ABDs themselves, compositions comprising them, and methods of using them. Thus, in embodiments the disclosure provides non-antibiotic and non-phage compositions, and methods of treating bacterial infections using them.

In embodiments compositions and methods that involve modified bacterial chromosomal islands are provided. Particular aspects of this disclosure are based on the highly mobile phage-inducible staphylococcal pathogenicity islands (SaPIs) and on similar elements from other bacteria known generally as phage-inducible chromosomal islands (PICIs). SaPIs and certain other mobilizable bacterial chromosomal islands are known in the art and are described in, for example, Novick R P, Ram G. The floating (pathogenicity) island: a genomic dessert. Trends in genetics. 2016; 32(2):114-126. doi:10.1016/j.tig.2015.11.005, the entire disclosure of which is incorporated herein by reference.

The SaPIs are ~15 kb genetic elements inserted in the staphylococcal chromosome at specific sites. There, they reside quietly, under the control of a SaPI-coded repressor, and replicate along with the chromosomal DNA. Certain bacteriophages, known as "helper phages", counter the repressor, de-repress the SaPI and induce the island to excise from the chromosome and to replicate autonomously. The replicated SaPI DNA is packaged efficiently in capsids composed entirely of phage virion proteins. Infectious phage-like particles (consisting of capsids+replicated SaPI DNA, tail and tail fibers) are formed and then released from the bacterial cell upon phage-induced lysis and are transferred at very high frequencies (depicted in the schematic of FIG. 1). Most SaPIs encode their own terminase small subunit (TerS), which directs exclusive packaging of the SaPI genome (instead of the phage genome) and most SaPIs encode capsid morphogenesis functions (CpmAB or Ccm), which remodel the phage capsids to accommodate the smaller SaPI genome (depicted in the schematic of FIG. 2).

SaPI genomes have a well-conserved modular organization where genes are grouped into functional modules: integration-excision, regulation, replication, packaging and phage-interference, and accessory genes (depicted schematically in FIG. 3A). Additional annotation of SaPI2 and non-limiting illustrations of SaPI derivatives referred to as antibacterial drones (ABDs) is provided in FIG. 4.

The SaPIs contain three types of genes: those critical for their distinctive lifestyle; those involved in phage-interference (which may also be important for their lifestyle); and those encoding toxins and other factors that contribute to the virulence and adaptability of the organism, but are irrelevant to the lifestyle of the SaPIs. These genes are referred to as accessory genes. They are the cargo of the island and are replicated and transferred along with the rest of the island. However, regulation of accessory gene expression is independent of the rest of the island and is dependent only on the activity of the specific accessory gene promoter(s). Therefore, when the SaPI resides in the chromosome and most of the SaPI genes are repressed, the accessory genes will usually be expressed.

In certain aspects this disclosure couples the promiscuous mobility of the SaPIs with recombinant DNA methodology to introduce a wide variety of antibacterial cargoes that can attenuate the virulence of, inhibit the growth of, or kill infecting bacteria, or modify non-pathogenic bacteria as described herein.

In various and non-limiting embodiments, the present disclosure provides for modifying any naturally occurring phage-packageable and mobilizable bacterial chromosomal island, which can further comprise detoxifying the island as described further below, optionally deleting genes that determine small-size capsids to increase the island's packaging capacity. These modifications enable an island, such as SaPI2 to carry, package and safely transfer more large segments of polynucleotides, such as up to 30 kb of genetically designed cargo.

The disclosure includes designing and constructing DNA cargo modules which encode antibacterial agent(s) and/or other agents that facilitate and/or improve and/or alter the function of the ABDs, and affect cells into which they are introduced. The disclosure includes inserting one or more anti-bacterial cargo modules into the modified island to create previously unavailable DNA islands (ABD-islands) that have the ability to kill or attenuate or otherwise modify any bacterial cell that is infected by it. The disclosure thus provides for exploiting the packaging system and high frequency transfer mechanism of the naturally occurring island to package and disseminate the re-purposed island DNA (ABD-DNA). The ABD-DNA is packaged in infectious phage-like particles (ABD-particles), which are released from the cell upon phage-induced lysis, or by other mechanisms, such as enzyme-mediated cell lysis. The disclosure includes customizing and optimizing ABD-particle producing bacterial strains, and includes such strains themselves.

In certain aspects the invention includes introducing by any suitable approach the ABDs into bacterial cells such that the cargo is expressed or otherwise affects function of the bacterial host. Depending on the cargo, ABD may alter, kill, weaken or disarm the targeted bacteria or the surrounding bacteria, or may deliver a drug or other substance to a particular locale as further described below. ABD can then proliferate throughout the bacterial population either spontaneously, or by design. ABDs have been constructed to treat staphylococcal infections and can be considered alternatives or adjuncts to conventional antibiotics, and are expected to be suitable for targeting a wide variety of other pathogenic or otherwise unwanted bacteria.

The disclosure includes all modifications that are described herein, and those that are depicted in the figures. In certain and non-limiting embodiments, modifications to prototypical SaPI, SaPI2, are as depicted in FIGS. 3A and 3B, and or deleting or modifying capsid morphogenesis genes to allow for cargo of up to ~30 kb. Additional modifications to the SaPI genome using SaPI2, other SaPIs or a combination thereof include modifications that increase the probability of induction and consequent spread, or to inhibit and/or prevent packaging of resident SaPIs (or parts of them), or to reduce unintended consequences of mispackaging by ABD during production and subsequently in vivo use.

Embodiments of the disclosure include at least two types of DNA cargo modules, which can be characterized by the type of anti-bacterial agents they encode—i) those that kill the infecting bacteria and, in some cases induce the SOS response and consequently induce prophages and the island, and ii) those that disarm or attenuate virulence.

The disclosure demonstrates prophylactic and therapeutic utility for specific embodiments of the invention, which can be readily extended to the other embodiments that are described herein by the skilled artisan when given the benefit of the present description. In particular, in vitro results presented herein show that both killing and disarming ABD-particles are effective against a derivative of a prototypical lab strain, Staphylococcus aureus NCTC 8325 and against an important clinical strain USA300. Typical results are shown in FIGS. 7 (killing) and 8 (disarming). Furthermore, in vivo results show that representative killing ABD-particles targeting S. aureus are not toxic to C57-b16 mice, do not elicit an immediate immune response and can find staphylococci in the infected mouse, can inject their ABD-DNA into these Staphylococcal cells, express the ABD cargo genes, express the ABD lifestyle genes, can integrate the ABD-DNA into the recipient cell, can treat an infection, and can prevent an infection from developing. In particular embodiments, it is demonstrated that killing ABD-particles targeting a chromosomal gene of *Listeria monocytogenes* are also effective against that organism. Killing of staphylococci by ABD2009 is shown in FIG. 12. ABD2009 is effective against *S. aureus* RN4220 (A), but not against RN4220 containing the lysostaphin immunity gene (B). Blockage of subcutaneous (SC) abscess formation is shown in FIGS. 13 and 14, and 15. Treatment of an SC abscess is shown in FIG. 15. Rescue by ABD2003 of mice given a lethal IP dose of staphylococci is shown in FIG. 16.

In view of the description provided herein, it will be apparent the disclosure provides in various embodiments: a polynucleotide comprising a bacterial pathogenicity island nucleotide sequence (referred to herein as a "B-PINS") comprising one or more modifications (referred to herein as a "modified B-PINS"), the one or more modifications including but not necessarily limited to a B-PINS comprising: i) a deletion or disruption of at least one virulence determinant of the B-PINS; and ii) an insertion of at least one cargo sequence into the B-PINS. In embodiments, the polynucleotide comprising the modified B-PINS is capable of being packaged within a bacterium into a phage-like particle that comprises or consists of bacteriophage capsid, tail and tail fiber proteins that is referred to herein as an antibacterial drone ("ABD"). The ABD is capable of infecting bacteria such that at least one cargo sequence is introduced into bacteria infected by the ABD. In non-limiting embodiments, one or more modifications of a virulence determinant in a B-PINS comprises a deletion of all or substantially all of the virulence determinants in the B-PINS. In embodiments, at least one cargo sequence comprises a polynucleotide sequence encoding an anti-bacterial agent that is functional against a target in at least some bacteria in a bacterial population. In embodiments, between 80-100% of the bacteria are killed.

In embodiments, the disclosure provides polynucleotides, and ABDs containing them, that include a DNA sequence or encode an RNA that comprises specificity for a target that is an essential gene, or an RNA encoded by an essential gene, or a variable gene, or an RNA encoded by a variable gene. In embodiments, the ABDs include a sequence encoding a protein that has specificity for a target and can participate in and/or cause its cleavage and/or inactivation. In embodiments, the ABCs include a sequence encoding a toxin, which may or may not be an excreted toxin, that is cytostatic against bacteria, or a non-toxin protein that inhibits growth of bacteria in a bacterial population, or inhibits formation of and/or kills persister bacteria and/or dormant viable but non-culturable (VBNC) bacteria, such toxin capable of killing bacteria that have not been infected by the ABD, and/or can kill bacteria that do harbor or are otherwise infected by the ABD. In embodiments, the toxin is lysostaphin. In embodiments, the ABDs comprise a sequence encoding an anti-sense RNA, or a Clustered Regularly Interspaced Short Palindromic repeats (CRISPR) guide RNA targeted to a sequence in a bacterium in a bacterial population. In embodiments, the ABDs comprise a sequence encoding a CRISPR-associated nuclease including a Cas9 nuclease, a Cpf1 nuclease, or a dCas9. In embodiments, a target of a component of the CRISPR system is a bacterial chromosome or a bacterial plasmid. In embodiments, a polynucleotide in the ABD comprises a deletion of SaPI genes cpmA and/or B. Pharmaceutical compositions comprising ABDs of this disclosure, including mixtures of distinct types of ABDs that are differentiated from one another at least by the polynucleotide they include, are provided. Methods of killing bacteria or otherwise limiting the growth of bacteria, or changing a phenotype of bacteria, are provided by introducing ABDs into bacteria. The bacteria may be in an individual, or present on or impregnated in a surface, such as a surface of an inanimate object, which may be any of a variety of objects, devices and the like, including but not limited to medical devices, surgical implants, and the like. Methods of producing ABDs by engineering bacteria to produce them are included in the disclosure, as are methods of separating ABDs from the bacteria, the engineered and infected bacteria, and the cell culture media comprising the bacteria and/or secreted ABDs. Isolated and/or purified ABDs are also included. In specific and non-limiting embodiments, an ABD or polynucleotide of this disclosure comprises a modified Staphylococcus aureus pathogenicity island (SaPI), which may be any of a SaPI, SaPI1, SaPI2, SaPIbov1, or SaPIbov2. Also provided are libraries of distinct ABDs.

BRIEF DESCRIPTION OF THE FIGURES

FIG. 7. Plating tests to demonstrate ABD antibacterial activities in vitro. A. Killing of S. aureus by ABD2003 and of L. monocytogenes by ABD2004. Suitable dilutions of ABD2002, 2003 or 2004 particle preparations were mixed with RN1, RN1Δagr, or L. monocytogenes SK1442, plated on TSB with 5 µg/ml tetracycline (Tc5), and incubated at 37° C. for 48 h. B. Inhibition of hemolytic activity by ABD2006. Suitable dilutions of ABD2005 or 2006 particle preparations were mixed with RN1 or USA300 LAC, plated on sheep blood agar plates supplemented with Tc5 and incubated at 37° C. for 48 h.

FIG. 8. inhibition by ABD2006 (CRISPR/dcas9, with agrP$_2$P$_3$ spacer), of agr-P$_3$lux reporter. Strains with integrated ABDs 2001, 2005 and 2006 and a control strain without any ABD were incubated with shaking at 37° C. Two 100 µl samples were withdrawn at each time point and assayed for growth (OD at 600 nM) and Relative Luciferase Units (RLU) in a Molecular Devices luminometer. Graphs show averages of experiments performed in triplicate with error bars representing standard deviations.

FIG. 12. Killing of staphylococci by ABD2009. S. aureus RN4220 (A) and RN4220 containing the lysostaphin immunity gene, lif(B) were infected with particles of ABD2009 (see Table 3), which contains the lysostaphin gene cloned to ABD2001, at a multiplicity of 3, then diluted and plated on tetracycline-containing agar to select for ABD transductants. Plates were incubated overnight at 37 C and then held at room temperature for an additional 3 days. The same number of colonies appeared initially on each plate; however, during the subsequent 3 days, those on the RN4220 plate slowly dissolved whereas those on the lif plate remained intact. The 4220 plating bacteria, which were sensitive to lysostaphin, but grew very slowly on the Tc plates, showed halos of lysostaphin lysis surrounding the dissolving colonies in plate A. This result shows that the production of lysostaphin was slow enough to allow the initial growth of the colonies, which then underwent lytic suicide as they aged.

FIG. 17. Examples of suitable cargo sequences and their sequence contexts are provided. com sequences are black on a white background. agr sequences are white on a black background. FIG. 17 provides SEQ ID NO:1.

FIG. 18 provides SEQ ID NO:2.

FIG. 19 provides SEQ ID NO:3.

FIG. 20 provides SEQ ID NO:5.

DETAILED DESCRIPTION

Figure 1:
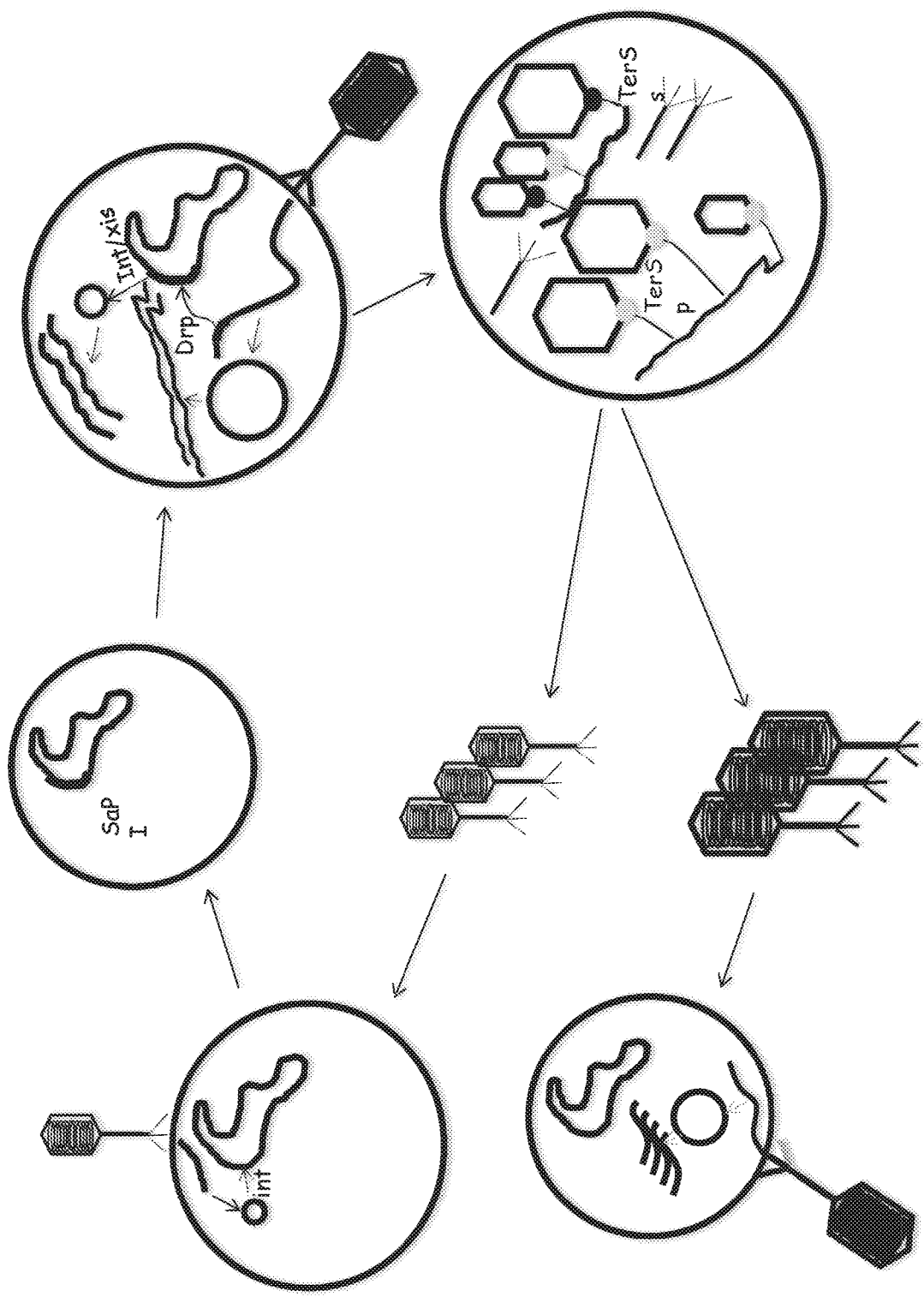
FIG. 1. Phage and SaPI replication cycles. SaPI particles and DNA are shown in black.
Figure 2:
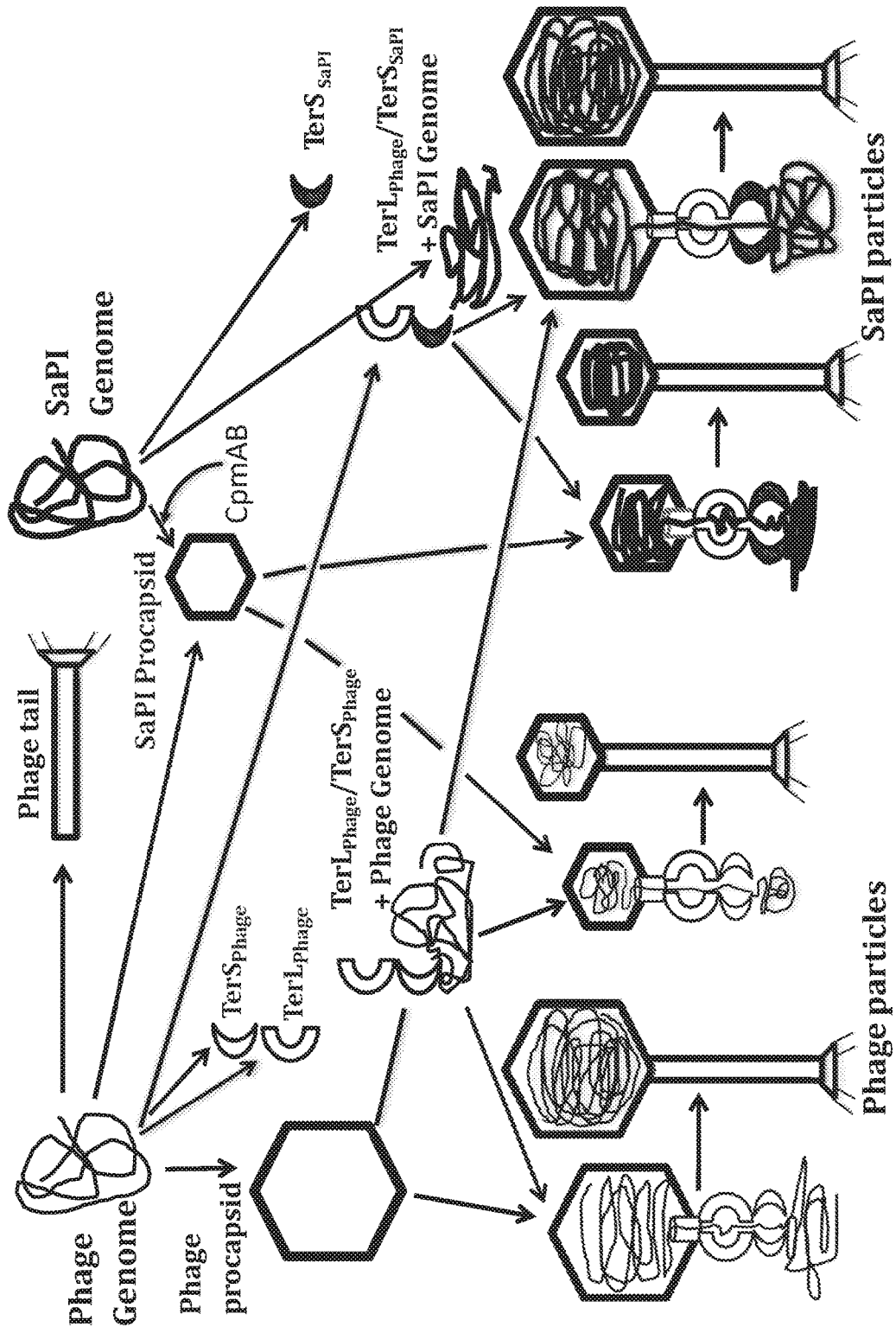
FIG. 2 Phage and SaPI DNA packaging. Phage genome, top left, encodes TerS and TerL, procapsids, and tails; SaPI genome, top right encodes TerS and modifies procapsid size. Phage and SaPI terminases package both phage and SaPI DNAs into procapsids of both sizes, resulting in both SaPI and phage particles of both sizes.

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The disclosure includes all polynucleotide and amino acid sequences described herein. Each RNA sequence includes its DNA equivalent, and each DNA sequence includes its RNA equivalent. Complementary and anti-parallel polynucleotide sequences are included. Every DNA and RNA sequence encoding polypeptides disclosed herein is encompassed by this disclosure. Amino acids of all protein sequences and all polynucleotide sequences encoding them are also included. Sequences of from 80-99.99% identical to any sequence (amino acids and nucleotide sequences) of this disclosure are included. In some embodiments a cargo module may be referred to herein as a module.

The disclosure includes polynucleotides comprising ABDs of this disclosure. In certain approaches of this disclosure expression vectors, such as plasmids, are used to produce one or more than one construct and/or component of the ABDs, and any of their cloning steps or intermediates. A variety of suitable expression vectors known in the art can be adapted to produce the ABDs of this disclosure.

In one aspect the disclosure includes a kit comprising one or more expression vector(s) that encode one or more ABD components. The expression vector in certain approaches includes a cloning site, such as a poly-cloning site, such that any desirable cargo gene can be cloned into the cloning site to be expressed in any target cell into which the ABD is introduced. The kit can further comprise one or more containers, printed material providing instructions as to how to use make and/or use the expression vector to produce ABDs, and reagents for introducing the expression vector into cells. The kits may further comprise one or more bacterial strains for use in producing the ABDs. The bacterial strains may be provided in a composition wherein growth of the bacteria is restricted, such as a frozen culture with one or more cryoprotectants, such as glycerol.

Methods of making ABDs are included and generally comprise introducing one or more polynucleotide encoding at least some portion of an ABD into suitable cells that comprise resident phages or prophages and/or other suitable genetic elements and/or proteins, allowing replication of the polynucleotides such that ABDs are formed, harvesting the ABDs from the cells, the cell cultures, or the culture supernatants, and optionally separating the ABDs from the cells, cell culture, cell culture supernatant, etc. Cells and cell cultures that harbor polynucleotides comprising the ABDs are included, as are isolated and/or purified ABDs. The ABDs can be purified to any desired degree of purity using standard approaches, such as density gradient separation or commercially available kits used to purify infectious particles made by bacteria.

In certain aspects the disclosure includes a pharmaceutical formulation comprising ABDs as described herein. The form of pharmaceutical preparation is not particularly limited, but generally comprises ABDs and at least one inactive ingredient. In certain embodiments suitable pharmaceutical compositions can be prepared by mixing any one type of ABD, or combination of distinct ABDs, with a pharmaceutically-acceptable carrier, diluent or excipient, and suitable such components are well known in the art. Some examples of such carriers, diluents and excipients can be found in: Remington: The Science and Practice of Pharmacy (2005) 21st Edition, Philadelphia, Pa. Lippincott Williams & Wilkins.

In another aspect the disclosure comprises delivering to bacteria a cargo via ABDs of this disclosure. The method generally comprises adding a preparation of ABDs of this disclosure to one or more bacterial cells, allowing attachment of ABDs to the cells, such as via a surface receptor, whereby the nucleic acids contained by the ABDs enter the cells. Subsequent to ABD nucleic acid entry the expression of the cargo occurs.

Administration of formulations comprising the ABDs as described herein can be performed using any suitable route of administration, which include but are not necessarily limited to intradermal, transdermal, intravenous, topical, intramuscular, intraperitoneal, intravenous, subcutaneous, oral, and intranasal routes. In certain aspects the disclosure includes providing the ABDs in the form of creams, aqueous solutions, suspensions or dispersions, oils, balms, foams, lotions, gels, cream gels, hydrogels, liniments, serums, films, ointments, sprays or aerosols, other forms of coating, or any multiple emulsions, slurries or tinctures. Compositions comprising ABDs may also be used to treat inanimate objects, such as medical devices, or implements used in food handling. In embodiments, the device is an implantable medical device or other implanted surgical object, whether permanent or temporarily implanted, including but not necessarily limited to an indwelling catheter or surgical implant of any kind.

It will be recognized by those of skill in the art that the form and character of the particular dosing regimen employed in the method of this disclosure will be dictated by the route of administration and other well-known variables, such as the age, sex, health and size of the individual, the type and severity of bacterial infection, or risk of bacterial infection, and other factors that will be apparent to the skilled artisan given the benefit of the present disclosure.

The compositions can be administered to humans, and are also suitable for use in a veterinary context and accordingly can be given to non-human animals, including but not limited to non-human mammals, and avian animals, and/or to any eukaryotic organism, including plants, wherein targeting of bacteria would be desirable.

In embodiments the ABDs are introduced into a subject as a component of a pharmaceutical composition. In certain aspects, the ABDs can be administered using any suitable route and method which may in part be dictated by the type of cargo that is encoded in the ABD, and the subject to which the ABDs are administered, the type and severity of the bacterial infection, its location, and other factors that will be apparent to those skilled in the art. In embodiments, the amount of ABDs is an effective amount such that the cargo achieves a desired result. The desired result can comprise a prophylactic effect or a therapeutic effect. In this regard, the type of cargo that the ABDs encode is not particularly limited and non-limiting illustrations are described further below.

This disclosure is considered to be suitable for targeting any microorganism that is susceptible to infection by any ABD described herein. In present embodiments the bacteria that are targeted by ABDs of this disclosure are Gram-positive. In alternative embodiments the bacteria that are targeted by ABDs of this disclosure may be Gram-negative. In embodiments the bacteria are resistant to one or more antibiotics and the ABDs kill or reduce the growth of the antibiotic-resistant bacteria, and/or the ABDs sensitize the bacteria to an antibiotic by, for example, use of cargo that targets an antibiotic resistance gene, which may be present on a chromosome or a plasmid. The disclosure is thus suitable for targeting bacterial chromosomes or episomal elements. In certain approaches the present disclosure can comprise use of a composition comprising ABDs as the only antimicrobial agent in the composition, or the composition can also comprise other antimicrobial agents. In embodiments, the disclosure encompasses using ABDs in the same composition as at least one other antimicrobial compound, or in concurrent or sequential, distinct administrations wherein ABDs are administered separately from at least one other antimicrobial compound, examples of which include but are not limited to any known antimicrobial compound and/or compounds that interfere with, for example, bacterial quorum sensing. In various embodiments, the ABDs can be used with antibiotics that are members of classes such as aminoglycosides, beta lactams (with or without beta lactamase inhibitor such as clavulanic acid), macrolides, glyco-peptides, polypeptides, cephalosporins, lincosamides, ketolides, rifampicin, polyketides, carbapenem, pleuromutilin, quinolones, streptogranins, oxazolidinones, lipopeptides, etc.

In embodiments, the method of this disclosure is used to reduce or eradicate bacterial cells. A reduction can be determined by comparing bacteria treated with ABDs to any suitable control. Eradication can comprise killing all bacterial cells as determined using any suitable measurement of bacteria. The bacteria can be present in an infection, which may be systemic, or localized to any particular system, organ or tissue, including but not limited to a wound. The bacteria may also be present in a biological or non-biologic liquid, or on an inanimate surface, or a food product. In non-limiting examples the surface can be a non-porous surface, a surface in a hospital, or a surface that is used for food processing or preparation.

Embodiments of this disclosure may be used to reduce or eradicate persister bacteria and/or dormant viable but non-culturable (VBNC) bacteria, and/or small-colony variant (SCV) bacteria. Such cells include but are not necessarily limited to mid-stationary phase or late-stationary phase cells. Such cells include pathogenic bacteria that neither grow nor die in the presence of conventional microbicidal antibiotics. In embodiments, persister cells and SCVs contribute to the recalcitrance of clinical infections. In embodiments, the bacteria are present in a biofilm. In embodiments, the disclosure inhibits formation of a biofilm, and may promote biofilm dispersal.

In certain embodiments, the method of the disclosure results in eradication of a bacterial population from an infection, such as from an infection of an organ, tissue, skin, or biological fluid from an individual, or from the surface of an inanimate object, including but not necessarily limited to medical devices, such as implantable or implanted medical devices, and/or any medical device that may stay in contact with the skin or be fully or partially present within the body of an individual for a period of time during which the surface of the device may be susceptible to biofilm formation. In embodiments, the method of this disclosure is used to reduce or eradicate bacteria that are present in anaerobic conditions. Thus, the disclosure in various implementations provides flexible approaches for a) killing b) attenuating virulence and c) inhibiting growth of a wide variety of bacteria in diverse environments, as well as for modifying non-pathogenic bacteria so that they have at least one intended characteristic/comprise/express a cargo as described herein.

In embodiments, disarming means reducing the capability of bacteria to cause damage to a host, such as by reducing or eliminating the capacity to produce toxins. In embodiments, attenuating means weakening the organism, such as by slowing or blocking its growth, or its ability to penetrate cells.

As discussed briefly above, the SaPIs are embedded in the staphylococcal chromosome at any of 5 different attachment sites that are similar in structure, but not sequence, to prophage attachment sites. The SaPIs are maintained in a quiescent state by a repressor. They are induced by certain staphylococcal bacteriophages (helper phages) to excise from the bacterial chromosome and replicate their DNA extensively within the bacterial cell. One key function of the helper phage is to counteract the SaPI repressor which enables the excision and replication of the SaPI. The inducing phage is meanwhile replicating alongside the SaPI and synthesizing the virion proteins that form the phage particle. The SaPI encodes 2 proteins, CpmA & B that direct the formation from the virion proteins of small-sized phage particle-like capsids into which their DNA is packaged. SaPIs and phages each encode sequence-specific terminase small subunit (TerS) enzymes that recognize specific packaging sequences (pac sites) in the DNA that are required for insertion of DNA into a phage precursor particle. The SaPI and phage TerS enzymes recognize different pac sites specific for their respective genomes, and do not cross-react. The resulting SaPI particles are released in very large numbers by phage-induced cellular lysis and, as they behave like phage particles, can usually infect any S. aureus bacteria with which they come in contact. For most S. aureus strains, phages and phage-like particles adsorb non-specifically to the ribitol-containing cell wall teichoic acid (WTA), enabling them to inject their DNA. Nevertheless, there is wide strain-specific variability in the host range of staphylococcal phages, which is normally determined by the ability to form plaques. By this criterion, host range is determined by intracellular factors rather than by adsorption specificity. These factors include phage inhibitors, restriction-modification systems, prophage immunity and the presence or absence of host functions required for phage reproduction. Consequently, limitations of phage host range, according to plaque-forming ability, do not generally affect the ability of a SaPI to enter and become established in a new cell.

In order to enable the production of large numbers of SaPI particles uncontaminated by co-produced infective bacteriophage particles, we have deleted the helper phage's TerS gene. This mutant phage can form normal (empty) page heads (procapsids) but cannot package phage DNA and therefore can exist only as a lysogen. As with WT lysogens, this mutant one can be induced by DNA damage (UV radiation or mitomycin C treatment—the so-called SOS response) to go through the phage lytic cycle, producing a crop of empty procapsids and phage tails. If, however, there is a co-resident SaPI, then all of the released particles, of both SaPI and phage sizes, will contain SaPI DNA which is packaged by means of the SaPI TerS. In the several embodiments of this invention, we have deleted SaPI genes cpmA & B responsible for the formation of small particles so that SaPI DNA is always packaged in phage-sized particles. Up to about 42 kb of SaPI DNA can be packaged in these particles. This means that approximately 30 kb of additional DNA can be inserted into the 13 kb modified SaPI genome.

Figure 5:
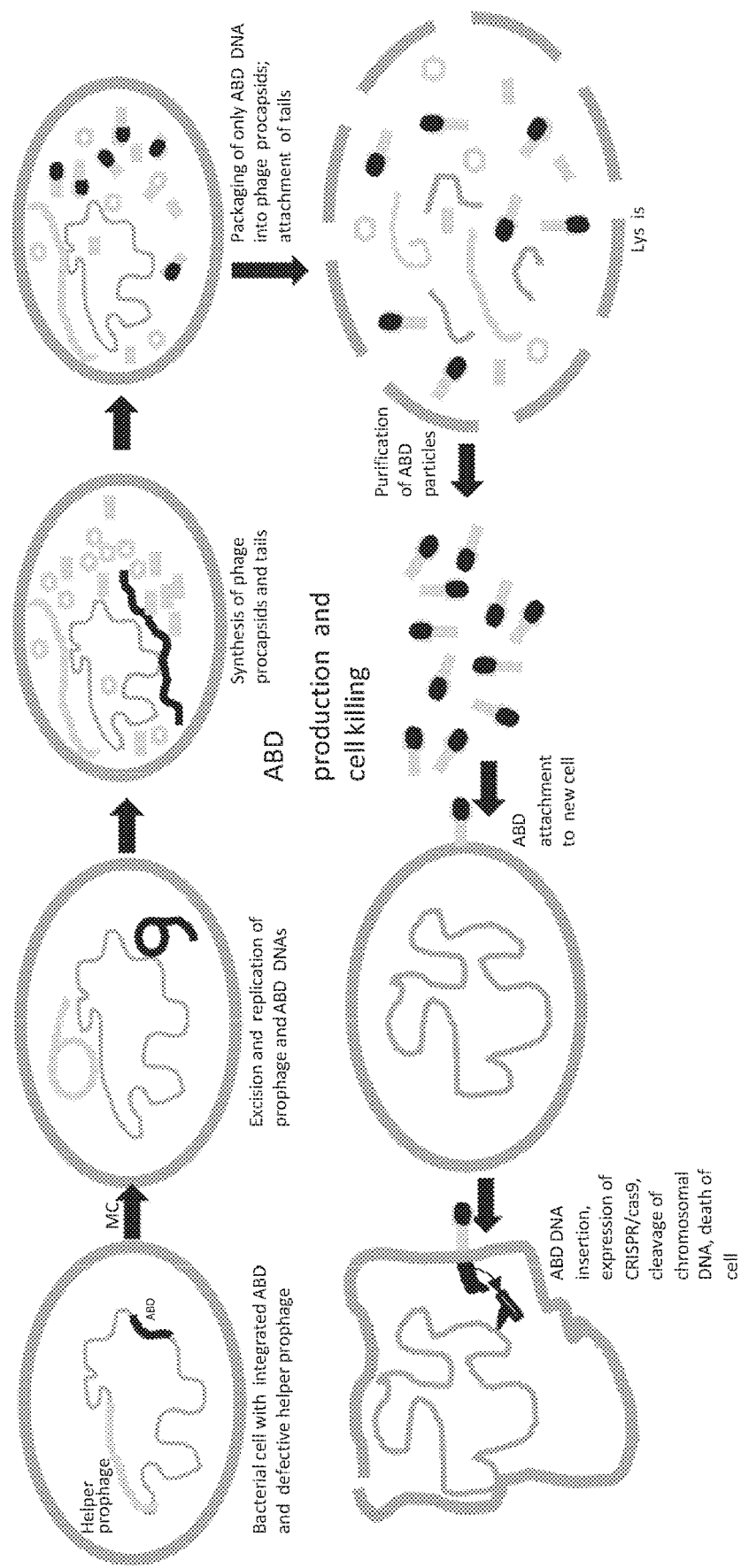
FIG. 5. Schematic representation of ABD production and function.

Following infection of new bacterial cells, the SaPI DNA is integrated into the new cell's chromosome and propagated thenceforth. Large numbers of particles for testing are produced by transfer to a strain containing the mutant helper phage described above, inducing the helper phage by mitomycin C and allowing the culture to undergo phage-induced lysis. As described above, the resulting lysate will contain only the engineered SaPI2 particles plus very rare particles containing mis-packaged host or helper phage DNA. This scheme is diagrammed in FIG. 5. These particles are concentrated by polyethylene glycol (PEG) precipitation, purified by density gradient centrifugation, dialyzed, filtered, enumerated and then used to infect any desired staphylococcal strain, including any strain that has caused an infection within the tissues of an animal or human. This strategy can be applied to the curing of a staphylococcal infection, which was demonstrated in an animal model, non-toxicity for mice given an intraperitoneal dose of $3 \times 10^{11}$ particles is also demonstrated. Such results are expected to be applicable to any mammal, including but not limited to humans, and other animals that are susceptible to bacterial infections.

In various and non-limiting embodiments, the present disclosure provides the following composition and methods, some of which are demonstrated in the application, and others of which can be predicted from what is demonstrated and described herein.

In one embodiment, the disclosure provides for modifying any naturally occurring phage-packageable and mobilizable bacterial chromosomal island, which can further comprise detoxifying the island (e.g., deleting and/or disrupting virulence determinants, preferably deleting all virulence determinants, other non-essential genes and optionally other accessory genes that makeup the island's natural cargo), and deleting the genes that determine small-size capsids, if any, thereby increasing the island's packaging capacity. These modifications enable an island such as SaPI2 to carry, package and safely transfer more than 30 kb of genetically designed cargo.

The disclosure includes designing and constructing DNA cargo modules. These cargo modules comprise DNA sequences encoding antibacterial agent(s). These cargo modules may also encode any other agents that facilitate and/or improve and/or alter the function of the ABDs. Numerous specific examples of DNA cargo modules are discussed below, and others will be apparent to those skilled in the art when given the benefit of the present description. The disclosure includes inserting one or more anti-bacterial cargo modules into the modified island to create a novel DNA island (ABD-island) that has the ability to kill or attenuate any bacterial cell that is infected by it.

The disclosure provides for exploiting the packaging system and high frequency transfer mechanism of the naturally occurring island to package and disseminate the re-purposed island DNA (ABD-DNA). The ABD-DNA is packaged in infectious phage-like particles (ABD-particles), which are released from the cell upon phage-induced lysis, or by other mechanisms, such as enzyme-mediated cell lysis. The disclosure includes customizing and optimizing ABD-particle producing bacterial strains, and includes such strains themselves.

In embodiments, the disclosure facilitates producing large quantities of ABD particles, which can be purified to any desired degree of purity. The particles can be included in a variety of compositions, including but not limited to pharmaceutical compositions.

In certain aspects the invention includes introducing by any suitable approach the ABDs into bacterial cells such that the cargo is expressed or otherwise affects function of the bacterial host. In embodiments, ABDs are introduced into bacteria and affect one or more properties of the bacteria. In embodiments, such effects are realized without integration of the ABD or any segment of its DNA content into the host chromosome; in other embodiments, the effects are realized subsequent to integration into the host chromosome.

Depending on the cargo, ABD may kill, weaken or disarm the targeted bacteria or the surrounding bacteria (or may deliver a drug or other substance to a particular locale). ABD can then spread throughout the bacterial population either spontaneously or by design. ABDs have been constructed to treat staphylococcal infections and can be considered alternatives or adjuncts to conventional antibiotics. Implicit in their design and construction is applicability to a wide variety of other pathogenic bacteria.

Figure 3:
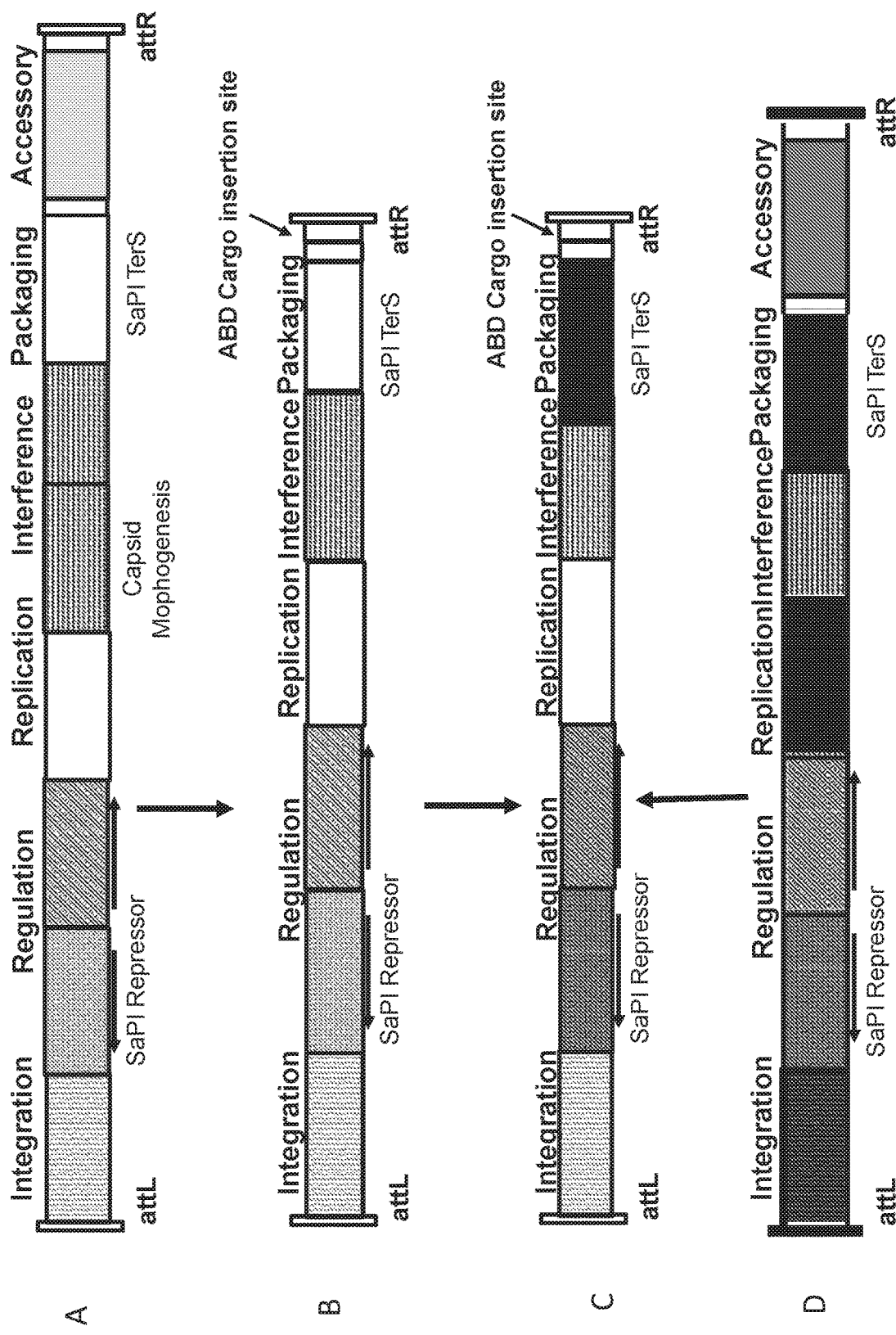
FIG. 3. SaPI2, SaPIbov2 and a hybrid between them A. SaPI2 genome organization. B. ABD2001. C. SaPI2 with regulatory region replaced by that of SaPIbov2. D. SaPIbov2

With respect to designing and constructing the genetic content of ABDs of this disclosure, the invention includes all modifications that are described herein, and those that are depicted in the figures. In certain and non-limiting embodiments, modifications to prototypical SaPI, SaPI2, are as depicted in FIGS. 3A and 3B. In representative examples, the disclosure comprises deleting or modifying all virulence determinants to make the island inert (i.e., "detoxifying" the SaPI).

Modifications also comprise deleting or modifying capsid morphogenesis genes, cpmAB, to allow for cargo of up to ~30 kb. Additional modifications to the SaPI genome using SaPI2, other SaPIs or a combination thereof include the following: To increase the probability of induction and consequent spread, the disclosure includes converting ABD into an auto-inducing island by incorporating the phage-determined de-repressor gene expressed from an SOS-inducible promoter. This would result in helper phage independent induction owing to stochastic SOS activity. In an approach the disclosure includes ABDs that, like the SaPIs, do not induce resident prophages, but if an endogenous prophage undergoes spontaneous induction (as often occurs in vivo), embodiments of the disclosure take advantage of it, even if the endogenous prophage is not a helper phage. In one approach, if the ABD is derived from SaPI2, the disclosure includes cloning dut. If the ABD is derived from SaPIbov2 or has a SaPIbov2 regulatory module, the disclosure includes cloning the SaPIbov2 de-repressor, gp15, from phage 80α. The advantage of using the SaPIbov2 repressor and cognate de-repressor is that induction of ABD is very unlikely to inadvertently induce SaPIs resident in human-adapted staphylococci. In general, the disclosure includes use of a SaPI repressor that is not known to occur in the resident SaPIs of the infecting (or otherwise targeted) bacteria. Methods for determining unique repressor sites (e.g., sites that are orthogonal to the targeted bacterial genome) are known in the art, and include, for example, sequencing and analysis of the whole or partial genomes of any bacterial sample of interest.

To inhibit and/or prevent packaging of resident SaPIs (or parts of them) by ABD terS, the disclosure provides for use of the bov2 terS and pac sites. Again, a general principle is: use a SaPI terS (and pac site) that is not known to occur in the resident SaPIs of the infecting bacteria. The disclosure provides for use of SaPIbov2 regulatory module, terS and pac site, and SaPI2 replication module, integration/xis and phage interference genes (FIG. 3C).

To reduce unintended consequences of mis-packaging by ABD during production and subsequently in vivo use, the disclosure provides for use of a cos terS, in lieu of a pac terS. The pac terS packages more efficiently and gives higher titers. Therefore, those skilled in the art can determine, depending on any particular situation, which terS is preferable, and one skilled in the art could make a suitable selection given the benefit of the present disclosure.

The disclosure includes at least two types of DNA cargo modules, which can be characterized by the type of antibacterial agents they encode: i) those that kill the infecting bacteria and, in some cases induce the SOS response and consequently induce prophages and the island, and ii) those that disarm or attenuate virulence.

Cargo destined to kill infecting bacteria in embodiments can disseminate the island (and other islands). For example, and as described more fully below, if cargo designed to kill bacteria in a bacterial infection damages the DNA of the bacterium it will trigger the so-called SOS response, which will induce endogenous prophages. If an endogenous prophage is a helper for either a resident SaPI or SaPI-like element, or for the incoming ABD, then the resident SaPI and/or the incoming ABD will also be induced and will spread to other neighboring cells when the first cell lyses. In embodiments, the incoming ABD may contain dut, the gene encoding the SaPI2 repressor. This will cause the incoming ABD to replicate following entry and to be packaged if an endogenous prophage is induced. It will also induce any endogenous SaPI that is sensitive to it.

Figure 6:
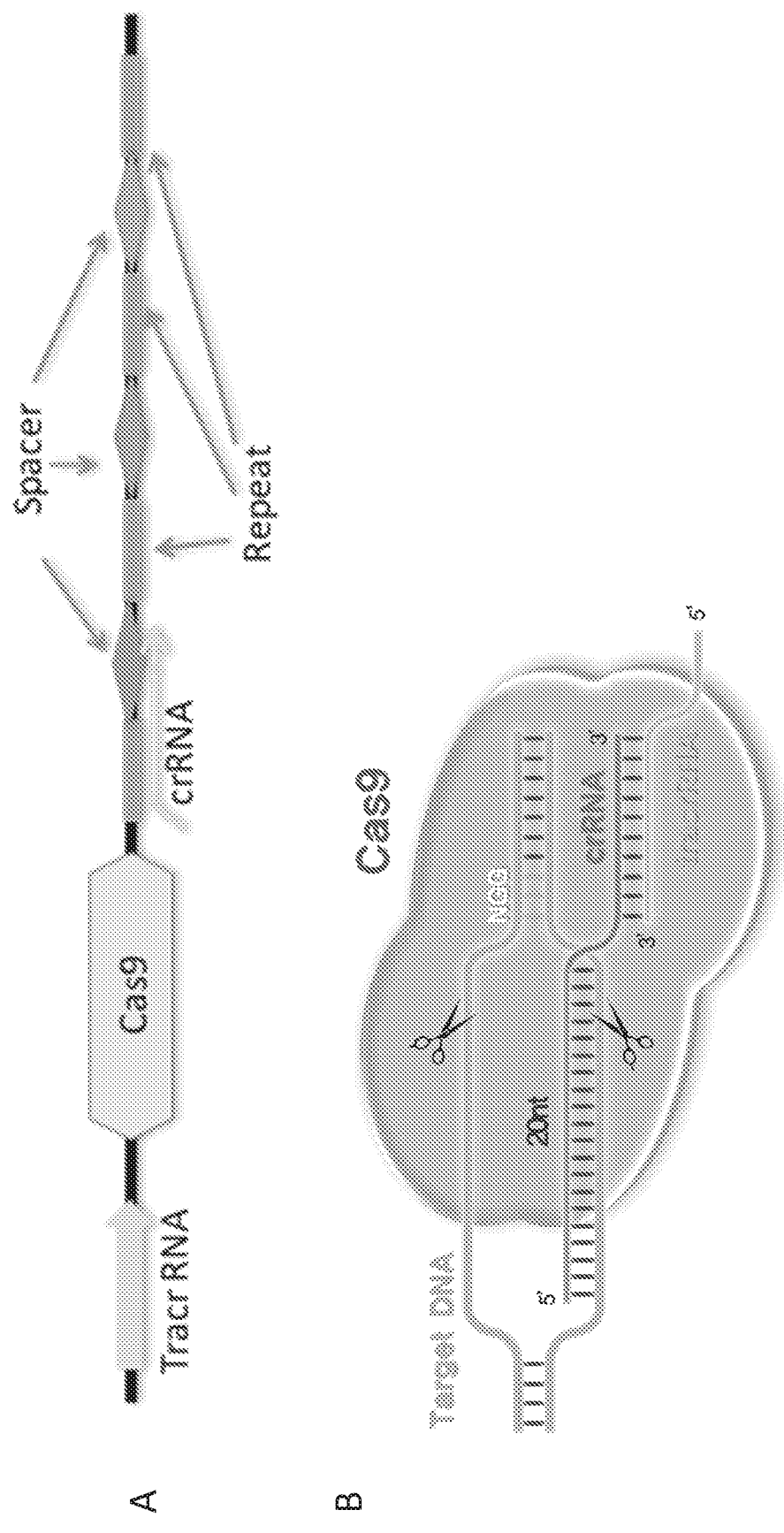
FIG. 6. CRISPR/Cas9 system. A. Simplified diagram of CRISPR locus. cr RNA is transcribed from one repeat and adjacent spacer and a second small RNA, tracr RNA, is transcribed separately. B. crRNA binds to the protospacer (recognition sequence) in the target DNA and tracr RNA binds jointly to crRNA and to Cas9, forming the complex that induces local melting of the DNA; Cas9 then cleaves both strands of the DNA at a pre-determined point. dCas9 (not shown) is a derivative of Cas9 lacking Cas9's nuclease function. It binds to the target DNA by the same mechanism, but instead of cleaving the target DNA it remains bound and blocks function of the targeted gene or regulatory element.

The disclosure includes different approaches (using cargo of the same type) to effect similar results. These include, for example, targeting all the bacteria in the population using any suitable agent, such as DNA encoding anti-sense RNAs targeting expression of essential genes. An anti-sense RNA can be expressed from the same promoter as the sense RNA (the target) so both sense and anti-sense can be expressed at the same time, alternatively, the antisense could be expressed from a strong constitutive promoter. In embodiments, the cargo comprises genes encoding a toxin that acts within the bacterial cell (such as the toxin of a toxin, anti-toxin module). These genes can be expressed from constitutive promoters or from promoters induced within the infected host such as temperature-sensitive promoters. In embodiments, the cargo comprises genes encoding a toxin that is secreted and acts outside the cell (ex. lysostaphin). Production of these toxins would affect not only the bacterial cell that has been infected by ABD, but also neighboring cells.) These genes can also be expressed from constitutive promoters or from promoters induced within the infected cell. In alternative embodiments, the cargo can comprise a CRISPR-Cas9 system configured with spacers targeting highly conserved constant chromosomal genes or plasmids or other mobile elements containing, for example, antibiotic resistance genes. In FIG. 6 is a diagram of the CRISPR system.

With respect to cargo that is intended to disarm, attenuate virulence, or weaken the infecting bacteria, those skilled in the art will recognize from the specification that the specific cargo will depend on the type of infection, and may take into account the genotype of the strain. The disclosure provides for use of modules to target all the cells in a population, or a subset of particular cells.

For targeting ABD-infected bacteria only, the disclosure includes using as cargo DNA encoding anti-sense RNAs targeting staphylococcal virulence genes (genes encoding toxins, enzymes, adhesins, proteins involved in immune evasion, proteins involved in the production of surface capsular polysaccharides). The cargo can also comprise DNA encoding anti-sense RNAs targeting genes encoding regulators of virulence, and/or genes required for biofilm formation, such as the intercellular adhesion (ica) operon (see Table 1 for a list of genes referred to in the disclosure) which is repressed by IcaR.

TABLE 1

Bacterial and SaPI genes described herein.
Bacterial and SaPI genes

| Gene | Locus tag, ID or ref. | Description or function |
| --- | --- | --- |
| agrA | SAOUHSC_02265 | Agr response regulator |
| agrB | SAOUHSC_02261 | AgrD processing enzyme |
| agrC | SAOUHSC_02264 | Agr signal receptor-histidine kinase |
| agrD | SAOUHSC_02262 | Agr autoinducing peptide precursor |
| blaZ | ID: 2610354 | β-lactamase |
| comA | BSU31680 | Competence signal receptor |
| comP | BSU31690 | Competence response regulator |
| comQ | BSU31710 | Competence processing enzyme |
| comX | BSU31700 | Competence peptide |
| covA | Microbiol Mol Biol Rev 63: 174 | Streptococcal global virulence regulator |
| cpmA | Virology 432:277, 2012 | SaPI capsid morphogenesis |
| cpmB | Virology 432:277, 2012 | SaPI capsid morphogenesis |
| dnaA | BSU00010 | Chromosomal replication initiator |
| dut | SA80_28 | dUTPase |
| eta | pETB_p07 | Exfoliative toxin |
| fib | SAOUHSC_01114 | Fibrinogen binding protein |
| fnbA | SAOUHSC_02802 | Fibronectin binding protein |
| fnbB | SAOUHSC_02803 | Fibronectin binding protein |
| gelE | J. Bacteriol. 189:1358 | Gelatinase |
| ghoT | ECK4122 | Membranolytic toxin |
| icaR | SAOUHSC_03001 | Repressor of ica operon |
| int | SA1810 | integrase |
| lsp | | lysostaphin |
| llo | lmo0202 | listeriolysin |
| mecA | NI36_00210 | Methicillin resistance PBP-2A |
| pezT | STH8232_0686 | Inhibitor of cell wall synthesis |
| pri | | DNA primase |
| ptiA | Novick&Ram TIG op. cit. | SaPI Phage interference protein |
| ptiB | Novick&Ram TIG op. cit. | SaPI Phage interference protein |
| ptiM | Novick&Ram TIG op. cit. | SaPI Phage interference modulator |
| rep | pSK1_p03 | Replication initiation |
| rsbW | USA300HOU_2060 | Inhibitor of sigmaB function |
| saeR | SAOUHSC_00715 | Response regulator of sae signaling system |
| spa | SAOUHSC_00069 | Staphylococcal protein A |
| srtA | SAR2608 | sortase |
| tarFIJLS | SA40_0212 | Teichoic acid synthesis operon |
| terL | PI31_gp44 | Terminase large subunit |
| terS | phiJB_ORF42 | Terminase small subunit |
| tst | SA1819 | Toxic shock syndrome toxin-1 |
| uvrB | SAA6008_00773 | DNA damage repair |
| wzg | INV104_02980 | Pneumococcal capsule regulator |
| xis | 80α_gp02 | Phage or SaPI excision |

This gene, the product of which interferes with biofilm formation, can be expressed from a strong constitutive promoter, as one example. The cargo can comprise genes required for producing an inhibitory peptide that can block the activation of the staphylococcal global regulator of virulence, agr, and consequently, can block production of most staphylococcal toxins. These genes can be expressed from a quorum-sensing promoter, for example, In embodiments, the cargo can comprise a CRISPR/dCas9 with spacers targeting promoters of global regulators of virulence or of biofilm formation, thereby inhibiting their expression without modifying the chromosome. Thus, it will be apparent that for targeting ABD-infected bacteria only, in embodiments, the cargo is suitable for affecting the expression/production/activity of any one or combination of: virulence determinants and regulators, biofilm determinants and regulators, sensors to different environmental cues, genes that affect metabolism, and genes that affect antibiotic resistance, or resistance to other agents. Thus, in embodiments, the disclosure comprises sensitizing bacteria to one or more agents.

For targeting ABD-infected bacteria and bacteria surrounding ABD-infected bacteria, in embodiments, genes required for producing an agr-inhibitory peptide can be added, as described above. In embodiments, cargo modules can be grouped by mechanism of action. In embodiments, cargo can be adapted to produce antisense RNA used to target any one or combination of: secY (killing), agrA, saeR, spa, fnbA, or fnbB. In embodiments, cargo can be adapted to produce toxins without anti-toxins, including but not limited to pezT (killing), ghoT (killing). In embodiments, cargo can be adapted to target Staphylococcal regulators, such as agrA, or to produce quorum sensing inhibitors, or to include one or more systems and spacers for CRISPR/Cas9 (killing), or for CRISPR/dCas9 inhibition of gene expression. In an embodiment, the disclosure comprises cargo adapted to express an extracellular-acting toxin or enzyme without an immunity gene, such as Lysostaphin (for killing).

In embodiments, the disclosure includes inserting two or more cargo modules into the basic modified SaPI2 and into each variant. With these embodiments, a pathogenic island can be converted into a therapeutic island.

It should be recognized that each type of ABD (killing or disarming) may have at least 2 cargo modules of the same type to reduce the probability of resistance or of a single inactivating mutation. When the ABD particles are administered with an antibiotic, the ABD can carry cargo that targets the appropriate antibiotic resistance gene, in addition to its regular killing or disarming cargo. Thus, the disclosure in embodiments also comprises targeting specific bacteria with specific variable genes (such as cell capsule variants, antibiotic resistance genes, etc.) including by using elements such as: DNA encoding anti-sense RNAs targeting highly conserved variable genes; CRISPR-Cas9 with spacers targeting highly conserved variable genes; and CRISPR-dCas9 with spacers targeting the promoters of highly conserved virulence genes or genes regulating virulence.

In certain implementations, the disclosure comprises exploiting the natural packaging system and high frequency transfer of the SaPIs. In certain examples, the disclosure accordingly includes creating (customizing and optimizing) ABD-particle producing strains by, for instance, customizing the particle-producing strains for the basic ABD or for variants. A lysogenic strain with a mutant prophage (ΔterS) will ensure that there is a high titer of ABD particles and no viable phage particles. Depending on which variant of SaPI is used, the phage will be a helper phage or need not be. In other implementations, a modified prophage (ΔterS) (helper and non) will be used that produces particles with different receptor specificity for treating infections caused by the atypical *S. aureus* strains of the ST395 lineage. In certain implementations, the producing strains will be customized for the specific antibacterial modules. For example, for ABDs with killing modules the particle-producing strain would be made insensitive to the killing.

In embodiments, the disclosure comprises producing large quantities of purified ABD-particles. In embodiments, the disclosure comprises delivering ABD-particles in vivo to the infecting bacteria and consequently treating the infection.

The disclosure demonstrates prophylactic and therapeutic utility for specific embodiments of the invention, which can be readily extended to the other embodiments that are described herein by the skilled artisan when given the benefit of the present description. In particular, in vitro results presented herein show that both killing and disarming ABD-particles are effective against a derivative of a prototypical lab strain, *Staphylococcus aureus* NCTC 8325 and against an important clinical strain USA300. Typical results are shown in FIGS. 7 (killing) and 8 (disarming). Furthermore, in vivo results show that representative killing ABD-particles targeting *S. aureus* are not toxic to C57-b16 mice, do not elicit an immediate immune response and can find staphylococci in the infected mouse, can inject their ABD-DNA into these Staphylococcal cells, express the ABD cargo genes, express the ABD lifestyle genes, can integrate the ABD-DNA into the recipient cell, can treat an infection, and can prevent an infection from developing. The disclosure also demonstrates that killing ABD-particles targeting a chromosomal gene of *Listeria monocytogenes* are effective against that organism.

SaPI genomes have a well-conserved modular organization. Genes are grouped into functional modules that mediate integration-excision, regulation, replication, packaging and phage-interference, and accessory genes (FIG. 3*a*). The model system in the demonstrations of this disclosure is based on the well characterized SaPI, SaPI2, and its helper phage, 80α. It is readily applicable to other SaPIs or SaPI-like elements in staphylococci or other bacteria, given the benefit of the present disclosure. However, it is expected that any SaPI can be adapted for use in embodiments of the invention. In this regard, non-limiting examples of specific SaPI sequences are given in the following Table 2. The table provides in the left column a GenBank accession number that pertains to the genome of each bacterial strain or to the sequence of the SaPI itself. The genome of strain NY940 has not been sequenced. Bacterial strain names are provided in the "Strain" column. All nucleotide and amino acid sequences that are indexed in the NCBI database for the accession numbers given in Table 2 are incorporated herein by reference as they exist on the date of this application or patent. Table 2 includes the att site type and its sequence. The SaPI coordinates for SaPI sequences when present in bacterial chromosomes are given by flanking nucleotide position in the bacterial genome as indicated for the 5' and 3' positions. The approximate sizes of the elements are given (those smaller than 12 kb are defective), as are the names of the particular SaPIs that have been published. Those lacking names have been identified by genome examination.

TABLE 2

SaPI Examples

| Accession # | Strain | Att site | Att site sq | SEQ ID | SaPI coordinates (5'-3') | | Size, Kb | SaPI |
|---|---|---|---|---|---|---|---|---|
| CP012409.1** | Tager 104 | I | AAAGAAGAACAATAATAT | 6 | 1196124 | 1211879 | 15.8 | |
| cP010942.1** | 949-S8- S. epidermidis | I | AAAGAAGAACAATAATAT | 7 | 2243432 | 2251563 | 8.1 | |
| AY954948.1 | NY940 | I | AAAGAAGAACAATAATAT | 8 | | | 15.6 | SaPI 1028 |
| BX571856.1** | MRSA252 | I | AAAGAAGAACAATAATAT | 9 | | | 15.1 | SaPI4 |
| AF217235.1* | RF122 | II | TAATTATTCCCACTCAAT | 10 | | | 15.8 | bov1 |
| AY220730.1* | V329 | II | TAATTATTCCCACTCAAT | 11 | | | 27 | bov2 |
| CP019945.1** | BA01611 | II | TAATTATTCCCACTCAAT | 12 | 467996 | 481943 | 14.0 | |
| CP014791.1** | MCRF184 | II | TAATTATTCCCACTCAAT | 13 | 391487 | 396451 | 5.0 | |
| HM228919.1* | JP5338 | II | TAATTATTCCCACTCAAT | 14 | | | 13.5 | SaPIbov5 |
| BA000033.2** | MW2 | III | TCCCGCCGTCTCCAT | 15 | 2088648 | 2100838 | 14.4 | SaPI MW2 |
| BA000017.4** | MU50 | III | TCCCGCCGTCTCCAT | 16 | | | 14.4 | SaPI m4 |
| AP006716.1** | JCSC1435 S. haemoolyticus | III | | | | | 16.6 | ShPI2 |
| KT845956.1** | 4s-13 S. epidermidis | III | TCCCGCCGTCTCCAT | 17 | 79 | 21426 | 21.3 | Double SaPI |
| LT615218.1** | AUS0325 | III | TCCCGCCGTCTCCAT | 18 | 794655 | 846139 | 51.5 | Triple SaPI |
| U93688.2* | RN4282 | IV | TTATTTAGCAGGAATAA | 19 | | | 15.2 | SaPI1 |

TABLE 2-continued

SaPI Examples

| Accession # | Strain | Att site | Att site sq | SEQ ID | SaPI coordinates (5'-3') | | Size, Kb | SaPI |
|---|---|---|---|---|---|---|---|---|
| CP000046.1** | COL | IV | TTATTTAGCAGGAATAA | 20 | | | 15.6 | SaPI3 |
| C0015447.1** | M92 | IV | TTATTTAGCAGGAATAA | 21 | 911782 | 926360 | 14.6 | |
| CP019590.1** | C2406 | IV | TTATTTAGCAGGAATAA | 22 | 901697 | 915669 | 14.0 | |
| CP020619.1** | JE2 | IV | TTATTTAGCAGGAATAA | 23 | 896724 | 910696 | 14.0 | |
| CP013182.1** | SA40TW | IV | TTATTTAGCAGGAATAA | 24 | 850818 | 866767 | 15.9 | |
| CP017094.1** | 2148.CO1 | IV | TTATTTAGCAGGAATAA | 25 | 1966279 | 1980248 | 14.0 | |
| CP012120.1** | USA300 | IV | TTATTTAGCAGGAATAA | 26 | | | 14.0 | SaPI5 |
| CP016855.1** | 5118.N | IV | TTATTTAGCAGGAATAA | 27 | 897139 | 911106 | 14.0 | |
| AB690438.1* | PM1 | IV | TTATTTAGCAGGAATAA | 28 | | | 12.1 | SaPIPM1 |
| BA000018.3** | N315 | V | TTTTACATCATTCCTGGCAT | 29 | | | | SaPIN1 |
| AJ938182.1** | RF122 | V | TTTTACATCATTCCTGGCAT | 30 | 2011992 | 2038438 | 26.5 | SaPI122 |
| AB716351.1* | #10 | V | TTTTACATCATTCCTGGCAT | 31 | 2046958 | 2031831 | 15.1 | |
| CP015447.1** | M92 | V | TTTTACATCATTCCTGGCAT | 32 | 2161986 | 2158884 | 3.1 | SaPI6Δ |
| CP019590.1** | C2406 | V | TTTTACATCATTCCTGGCAT | 33 | 2143261 | 2146401 | 3.1 | SaPI6Δ |
| CP012120.1** | USA300 | V | TTTTACATCATTCCTGGCAT | 34 | 2184162 | 2187302 | 3.1 | SaPI6Δ |
| CP019563.1** | SR434 | V | TTTTACATCATTCCTGGCAT | 35 | 2805478 | 12419 | 16.1 | |
| EF010993.1* | RN3984 | V | TTTTACATCATTCCTGGCAT | 36 | | | 14.7 | SaPI2 |
| AM292600.1 | CS6-EEFIC | V | TTTTACATCATTCCAGGCAT | 37 | | | 20.7 | SaRIfusB |
| AP008934 | 15305 S. saprophyticus | VI | CGAGGGGACTAATAAGT | 38 | | | 17.0 | SsPI15305 |

*SaPI sequence;
**whole genome sequence.

It is considered, and without intending to be limited by any particular theory, that ABD's exhibit two forms of tropism, one towards a specific pathogen and the other towards a specific infection. The first form is determined by ABD-particle adsorption specificity. Since ABD-particles are composed entirely of virion proteins, they have the same cell-surface specificity as the helper phage particles. Thus, to change the specificity of the ABD particle, the helper phage can be changed. While all presently known helper phages have been shown to adsorb to the bacterial cell walls via teichoic acid (WTA), different phages recognize different WTA structures. For example, most *S. aureus* strains produce a WTA that contains repeating ribitol-phosphate units decorated with N-acetyl-D-glucosamine residues. Phages 80α and Φ11 recognize this structure and therefore, when they are used as helper phages, the ABD particles will target most *S. aureus* strains and are expected to effectively treat (kill) infections caused by these strains. However, *S. aureus* strains of Glade ST395 produce an atypical WTA consisting of a glycerophosphate polymer modified with N-acetyl-D-galactosamine residues. To treat infections caused by these strains, the disclosure includes using a suitable helper phage such as Φ187, which recognizes this WTA structure. In embodiments, the disclosure comprises modifying or otherwise adapting compositions to tailor the cellular tropism of the modified SaPIs, which may be provided as ABDs. To expand the ABD host range to include ST395 strains, the present disclosure includes using an available hybrid host strain, PS187-H, which contains the glycerol-WTA for phages such as 187 as well as the ribitol WTA receptors for 80α and other phages of its type. This strain will by lysogenized by phage 187 ΔterS. An ABD can be introduced by transfer via phage 80α. Since phage 187 is not a helper phage for SaPI2-based ABDs, the ABD will contain dut driven by the SOS-inducible uvrB promoter. Growth in the presence of mitomycin C will then induce both the prophage and the ABD and the resulting ABD particles will be specific for ST395 strains. The disclosure includes broadening the ABD system to other species, such as by modifying existing ABDs to infect these other organisms, using this same strategy. In general, the disclosure includes adapting the ADBs using genes from streptococci, which are closely related to staphylococci, by cloning the gene(s) for streptococcal phage receptor specificity into a standard *S. aureus* host strain, then lysogenizing this strain with a streptococcal phage, deleting its terS gene and introducing an ABD of this disclosure to provide a strain that will produce ABD particles specific for streptococci. Alternatively, the tail fiber genes from a suitable *streptococcus* phage can be cloned into a helper phage, followed by introduction of an ABD, and induction of the phage and ABD using a suitable reagent such as mitomycin, thereby producing particles that are specific for the *streptococcus.*

Modifications of these approaches will be apparent to those skilled in the art, given the benefit of the present disclosure. In embodiments, the disclosure comprises testing a sample of bacteria to determine helper phages which the bacteria contain, and selecting and/or generating suitable ABDs such that the bacteria can be effectively targeted based on a tropism designed to enable infection and killing and/or modifying of such bacteria.

In embodiments, the disclosure includes tailoring the ABDs toward specific infections. A plurality of distinct ABDs is described herein, wherein members of the plurality have distinct genetic elements relative to one another. Thus, in embodiments the disclosure includes a library of distinct ABDs. In embodiment, the members of the library differ from one another in their genetic content. For example, a first member of the library can comprise any genetic modification as described herein, whereas a second member of the library may comprise a different genetic modification, or different combinations of genetic elements. The ABDs can be, for example, held in separate containers, and for example indexed using any suitable indicators, including but not limited to text, numerical, and machine readable indicators, such as bar codes. Providing a library of ABDs facilitates rapid selection of a suitable ABD to, for example, target a specific type infection that an individual may have. Thus, in one embodiment, an individual is diagnosed with an infection by a particular type or class of bacteria, and a ready-made preparation of ABDs made according to this disclosure can be selected and administered to the individual. The ABDs may be stored in any suitable form, such as lyophilized, or frozen, and may be ready for, for instance, reconstitution into a pharmaceutical formulation.

The ability to target a wide diversity of bacteria, including but not limited to, via accounting for tropism as discussed above, imparts on the disclosure a powerful approach to modifying bacterial chromosomes using the ABDs that are described herein. In this regard it is established in the art that SaPI lifestyle includes integration of the SaPI in to the host chromosome, and it was expected that this property of SaPIs would be essential for a wide variety of implementations of this disclosure. However, in arriving at the present invention certain unexpected properties of ABDs in connection with their infectivity and killing activity came to light.

To use an ABD effectively, one must determine the number of ABD particles in the preparation. In the present disclosure, an unexpectedly high level of bacterial killing by the ABD with a CRISPR-Cas9 cargo module was observed. We had predicted that the Killing Units, measured by infecting a population of bacteria that have been treated with ultra-sound to disrupt clumps, then determining the fraction of surviving bacteria by plating for colony counts, would be equal to the Transfer Units, measured by colony formation on selective media, if the killing were very efficient and fewer, if less efficient. Enumeration of sub-microscopic particles, such as phage, SaPI, ABD particles, etc., is done microbiologically by counting the particles based on some specific property. In the case of a phage, this would be the ability of a single particle to form a plaque. A plaque is a circular clearing zone within a lawn of bacteria growing on an agar plate. The individual phage particle adsorbs to the surface of the bacterial cell and injects its DNA, which replicates within the cell, produces progeny particles and lyses the cell. The new particles infect surrounding cells, creating a zone of lysis, which is seen as a plaque. For a SaPI or ABD particle, this would be the ability to infect a bacterial cell and enable it to form a colony on an agar plate containing an antibiotic to which the SaPI or ABD confers resistance. In the disclosure, tetracycline (Tc) resistance, determined by the tetM gene, is used. A series of dilutions is prepared and a measured sample of each is mixed with a suitable number of Tc-sensitive bacteria—e.g. $10^8$- and the mixture spread on an agar plate containing a suitable concentration of Tc. Only cells infected by an ABD particle can grow and produce colonies on the plate. Counting the colonies and multiplying by the dilution factor gives the number of particles in the preparation, the titer of transducing units (TU). With an ABD containing a CRISPR/cas9 module with a spacer targeting a bacterial chromosomal gene, it was assumed that each cell infected by such a particle would be killed by a CRISPR-induced DSB in the chromosomal DNA. In an experimental test of this, a known number of ABD particles was mixed with twice the number of staphylococcal bacteria. Because of the random nature of the infection events, it was expected that about 39% of the bacteria (rather than 50%) should have been killed by the CRISPR, because 11% would have been infected by 2 or more particles. Much to our surprise, however, over 95% of the bacteria were killed. To achieve this killing frequency, one would have had to use a ratio of 5 particles per bacterial cell. In other words, the particle titer determined by measuring the formation of Tc-resistant colonies (using bacteria that were resistant to CRISPR killing) was about 10-fold lower than the particle titer measured by CRISPR killing. To confirm this, we performed a second test in which we used a ratio of 1:20 transducing particles to bacteria. If the killing and transducing titers were equal, a barely measurable 5% of the bacteria would have been killed. Instead, about 40% were killed, the expectation for a 1:2 ratio rather than a 1:20 ratio. The number of killing units (KU) is thus about 10× that of the TU. Without intending to be constrained by any particular theory, it is considered that the explanation for this disparity is that an incoming ABD DNA molecule, which is linear, must undergo two specific and possibly inefficient steps before the bacterium can grow on a Tc-containing plate: it must first form a closed DNA loop, which requires the action of a specific, possibly inefficient enzyme, and it must then integrate into the host cell's chromosome, via this closed loop, to be propagated. To kill a cell, however, the incoming DNA need not form a loop or integrate; it must simply express its CRISPR/cas9 module, which requires only a linear template. The implication of these results is that some 90% of infecting ABD particles never become stably established in a targeted bacterial cell. Among the genes that would be immediately expressed following entry of the ABD DNA is stl, which encodes the master repressor. Consequently the incoming DNA would be repressed and would probably not replicate, so that during division of the infected cell, it would be inherited by only one of the daughter cells. This means that the antibacterial cargo must complete its intended effect before the first cell division. Thus, there may be 2 types of ABD cargo—those that complete their antibacterial function before the first cell division, and those that do not. Of the latter, only those ABDs that become established by integration will be able to perform their inhibitory function, and, consequently, dosing must be based on the TU titer rather than on the KU titer. Therefore, in embodiments in which the ABD disarms rather than kills the targeted bacteria, it will either be able to replicate, by incorporating the *B. subtilis* phage 29 replication system, which uses a linear template, or will block the cell division mechanism of the targeted bacteria. Alternatively, it may be that the infecting bacteria multiply very slowly, so that neither of these approaches will be necessary.

The Cas9-induced double-stranded break induces the SOS response and consequently induces prophages before cell death is finalized. If a resident prophage is a helper phage (or any phage that can package the ABD genome), then the ABD (and consequently the killing) will spread to adjacent cells. Thus, the ABD killing zone can be considered analogous to a phage plaque. Accordingly, in embodiments, the disclosure comprises determining a number of Transfer Units in order to kill a known or estimated bacterial population. In embodiments, the disclosure comprises using standardized amounts of TUs for killing any particular bacterial population, which may be correlated with parameters that can be calculated by known approaches, such as the type or severity of infection. Thus, in embodiments, the disclosure includes providing pre-determined amounts of ABDs to kill and/or modify bacteria. In embodiments, the disclosure further includes testing a sample of the bacteria to determine any one or combination of characteristic of the bacteria, such as type of bacteria, severity of infection, pathogenicity/virulence of the bacteria, resistance to one or more antibiotics, the location of the infection, genetic components of the bacteria that can be targeted for killing or modification and/or for sensitizing the bacteria to a conventional anti-microbial agent(s), the amount of bacteria in an infection, and other parameters that will be apparent from this disclosure.

In one aspect the disclosure accordingly relates to attenuation of virulence of bacteria, and further comprises not only attenuating virulence of the ABD-infected cells, but also of the surrounding cells, thereby amplifying the attenuating effect. In an embodiment this aspect comprises attenuating a population of *S. aureus*, but similar approaches can be adapted for other bacterial types as described further below and as will otherwise be apparent to those skilled in the art given the benefit of the present disclosure.

Figure 9:
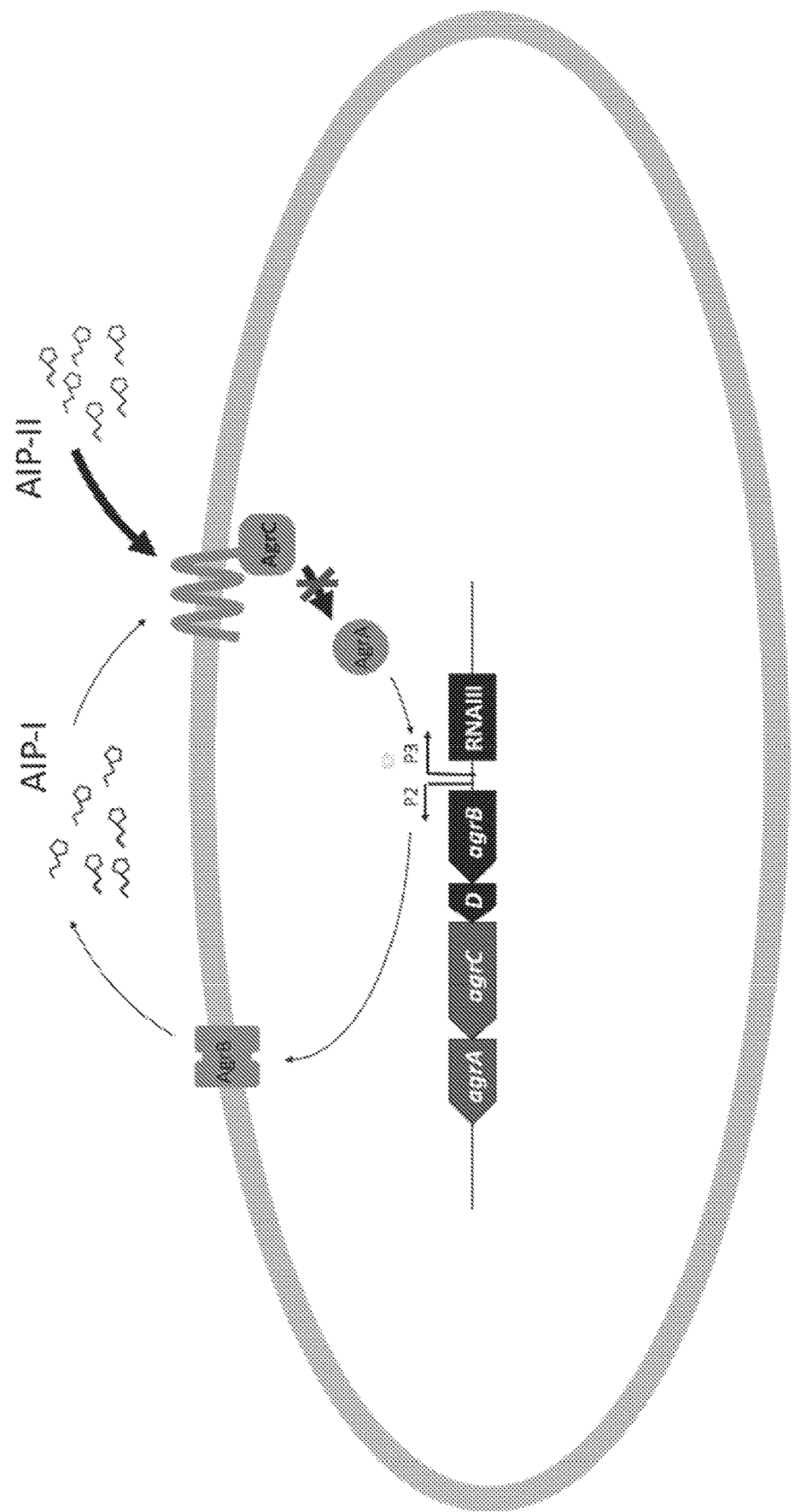
FIG. 9. The agr regulatory circuit. The agr locus, widely conserved among Gram-positive bacteria, consists of 2 transcription units driven by promoters P$_2$ & P$_3$. The P$_2$ operon encodes AgrB, a trans-membrane protein that processes the AgrD peptide to form a 7-9 amino acid peptide (the AIP) that is the activating ligand for AgrC, the receptor-histidine kinase component of the two-component signaling module, of which AgrA is the response regulator. Binding of the AIP to an extracellular loop of AgrC causes autophosphorylation of a histidine residue in the cytoplasmic domain of the receptor. The phosphate is then transferred to AgrA, activating its transcriptional regulatory function. AgrA~P binds to P$_2$, completing a positive feedback loop. It also binds to P$_3$, whose transcript is the regulatory RNA, RNAIII, which regulates indirectly the transcription of most virulence genes and directly the translation of a few key genes. RNAIII governs the production of most virulence proteins. AgrA~P separately activates transcription of a set of genes encoding virulence peptides known as phenol-soluble modulins. The agr system occurs as 4 allelic forms in S. aureus, such that interactions between one AIP and the signaling module of another allelic form are usually cross-inhibitory. Inhibition of agrI by AIP-II is shown.
Figure 10:
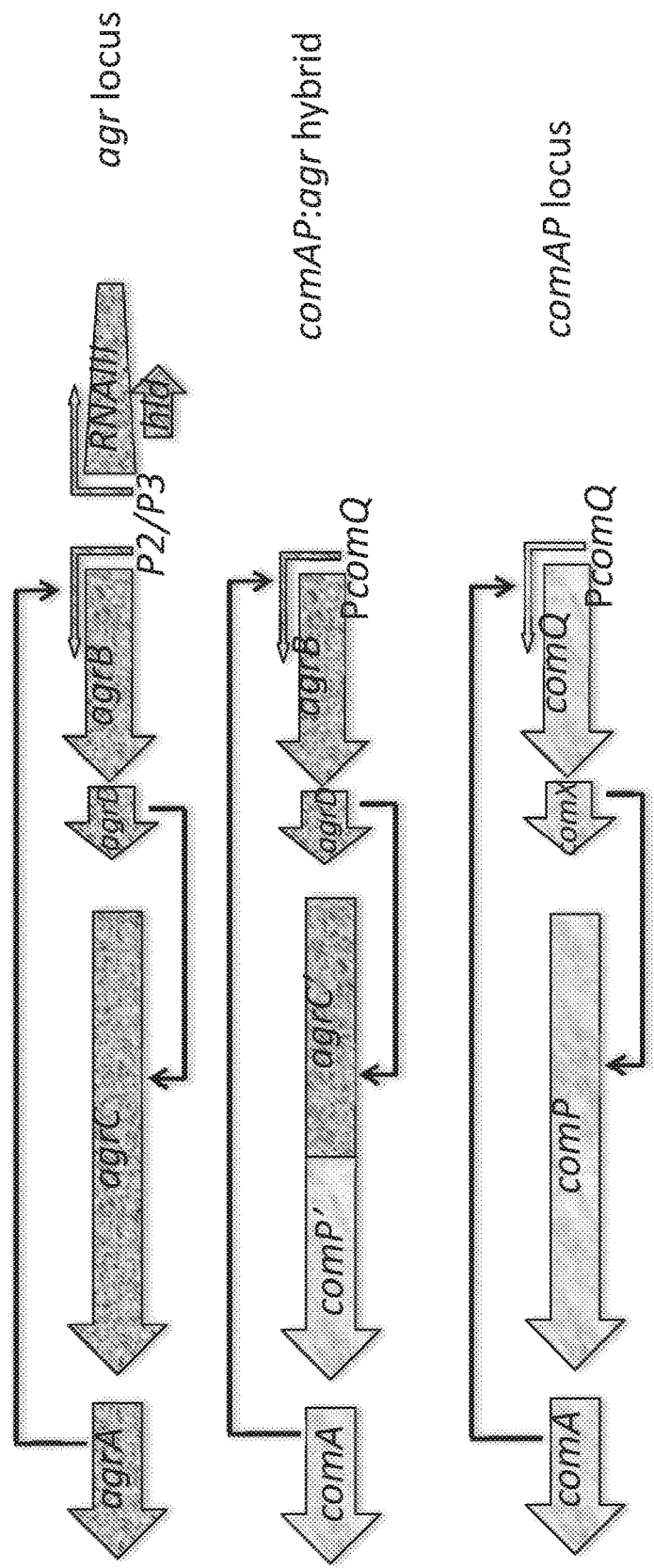
FIG. 10. Hybrid auto-regulatory circuit combining S. warneri agrBD, B. subtilis comA and B. subtilis-S. warneri comP-agrC hybrid. In the hybrid, driven by the comQ promoter, AgrB & D combine to produce an inhibitory AIP which blocks agr activation in target bacteria. ComA & P are a two-component signaling module from B. subtilis, parallel to agrA and C, in which phosphorylated ComA activates PcomQ, establishing an autoinduction circuit. ComQ promoter (PcomQ) drives the hybrid locus, inducing the expression of S. warneri AIP, which binds to the N-terminal moiety of the ComP-AgrC hybrid, activating phosphorylation of ComA, which up-regulates comQ. The S. warneri AIP inhibits the agr system in S. aureus strains of all 4 allelic types, and thus blocks virulence.

In embodiments, the disclosure comprises use of ABDs to affect bacteria into which the ABDs are introduced, and also to affect bacteria that may be near and/or in fluid communication with the ABD-infected bacteria, but may not necessarily be infected themselves. In one implementation ABDs are designed to cause infected bacteria to secrete an inhibitor of one or more quorum-sensing (QS) genes and/or QS modulating proteins. For example, in embodiments, and as discussed further below, a cell infected by an ABD produced according to this disclosure can be modified to secrete an inhibitor of the accessory gene regulator (agr), the global regulator of staphylococcal virulence. agr is an auto-inducing QS system that coordinates the expression of over 50 genes (encoding toxins, degradative enzymes, immune evasion factors, adhesins and other exoproteins) in response to bacterial cell density, discovered and characterized in the inventors' laboratory. FIG. 9 provides an illustration that is related to this embodiment. The complex agr locus has two major transcriptional units driven by the agr-inducible promoters, $P_2$ and $P_3$. The $P_2$ operon includes four genes, agrB, D, C and A and encodes a typical QS system. agrD encodes the precursor of an extracellular QS signaling peptide, the auto-inducing peptide (AIP). AgrB is required for processing and secretion of the AIP, which is the ligand of AgrC. AgrC and A form a classical two component system (TCS), with C the histidine kinase sensor (the detector of the QS signal) and A its cognate response regulator (the activator of the QS system). At a high cell density (the quorum), the AIP accumulates in the extracellular environment, binds the N-terminal trans-membrane domain of AgrC, C autophosphorylates, transfers a phosphate group to A, which then activates (up-regulates) transcription from $P_2$. Consequently, the $P_2$ operon is considered to be doubly autocatalytic, a key feature of all QS systems. AgrA~P also activates the divergent agr promoter, $P_3$, as well as the promoters of two operons that encode the important toxins, phenol-soluble modulins α and β. However, it is not AgrA, but the agr$P_3$ transcript, RNAIII, that is the major effector of global gene regulation in the agr system. While the basic architecture, regulatory circuitry and sequences of agrA and the 3' end of agrC are highly conserved among the staphylococci, agrB, D and the 5' end of C are variable. Allelic variations in these agr genes have resulted in the emergence of four QS specificity groups (with different AIPS and different corresponding AIP receptors) in *S. aureus*. Strains within a group (with homologous agr loci) cross-activate, but strains from different groups (with heterologous loci) exhibit strong mutual cross-inhibition. The other, non-*aureus* staphylococcal species appear to possess unique species-specific agr loci (some with more than one allelic variant). Several of these interfere with at least one of the *S. aureus* QS groups. The AIP (YSPCTNFF; SEQ ID NO:4) produced by *S. warneri* strains RN833 and SG1 has been shown to interfere with all four *S. aureus* QS groups (although, *S. warneri* is indifferent to the *aureus* AIPs). An agr-parallel QS system is found in *Bacillus subtilis*, where it controls competence rather than virulence. Moreover, this com locus is exactly analogous to the agr $P_2$ operon. It consists of four genes, comQ, X, P and A. comX encodes the precursor of the AIP; Q is required for its processing and secretion; C encodes the detector, A the activator of the com promoter and the locus is autoinduced. There even exist com allelic variants and com QS specificity groups. Thus, in embodiments, ABDs of this disclosure are engineered to produce a cargo that is a hybrid of com/agr QS operon as illustrated in FIG. 10, comprising or consisting of the *B. subtilis* com promoter, the *S. warneri* agr variable region, including agrB, D and the 5' moiety of C, and the *B. subtilis* com conserved region, including the 3' moiety of comP and the entire comA. The composite locus creates a fusion histidine kinase with the N-terminal transmembrane sensor domain of AgrC and the C-terminal cytosolic domain of ComP. This fusion protein is designed to detect the agrD-encoded AIP and to activate the comA-encoded response regulator. Therefore, the AIP will not only inhibit the four *S. aureus* agr groups, but also serve as the effector of a positive feedback loop, activating the hybrid locus, maximizing the production of the AIP (and minimizing the cost of producing it).

Since the QS promoters have a very low basal level (prior to activation), the disclosure further comprises insertion of a second promoter downstream of the com promoter and upstream of the agrB Shine-Dalgarno (ribosomal binding site). For this second promoter, suitable choices include but are not necessarily limited to the following: Pcad, which has a high basal level, $agrP_1$, which is induced in vivo, or the promoter used to express CRISPR-Cas9 in other cargo modules. Non-limiting examples of suitable cargo sequences and their sequence contexts are shown in FIG. 17 (SEQ ID NO:1).

In order to implement this approach, modifications (deletions, insertions and nucleotide changes) to SaPIs, basic Drones or ABDs can be made when the elements are integrated in the chromosome and standard allelic replacement vectors (pMAD, pKOR1 or pIMAY) are used to make these modifications. To streamline the process and facilitate cloning, the disclosure includes inserting all single modules between the terS and tetM (using the same Left and Right Flanking regions) and introducing a novel multiple cloning site (MCS) between the two flanks creating an off-the-shelf user-friendly vector, pMAD-FL-MCS-FR.

In an embodiment the disclosure includes constructing a hybrid (a tripartite) locus. This approach uses restriction enzymes and conventional cloning methodology, instead of Gibson Cloning. This approach facilitates rapid modifications of any of the module's three parts individually. The Pcom part can be amplified from *B. subtilis* 168 genomic DNA with the primer pair Pcom-PstIF and Pcom-EcoRIR, the agr variable region from *S. warneri* SG1 genomic DNA with the primer pair agrv-EcoRIF and agrv-KpnIR and the com conserved region from *B. subtilis* 168 genomic DNA with the primer pair comc-KpnIF and comc-XhoIR. Restriction sites (PstI, EcoRI, KpnI and XhoI) can be incorporated in the appropriate PCR primers and the purified amplicons digested with restriction enzymes EcoRI and KpnI. The restricted PCR products can be ligated and the ligated DNA used as a template to be amplified using the outer primers, Pcom-PstIF and comc-XhoIR. This PCR product covering the entire hybrid locus can be purified and cloned into pUC18 at the HincII site of the polylinker (by blunt ligation). The insert can be sequenced and for verification and subcloned into the allelic replacement vector pMAD-FL-MCS-RL using restriction enzymes PstI and XhoI which are novel in the MCS.

As discussed above, aspects of this disclosure include an approximately 15 kb DNA molecule that is a derivative of staphylococcal pathogenicity island SaPI2 with the following modifications: the native virulence genes of the island, tst (encoding toxic shock syndrome toxin-1) and eta encoding exfoliative toxin A), have been replaced by a DNA segment containing the tetM gene for tetracycline resistance; in some embodiments, the capsid morphogenesis genes (cpmA & cpmB), and the phage interference gene, ptiB, have been replaced by a DNA segment containing the SaPI2 derepressor gene, dut. In embodiments, all or substantially all of the tst and eta genes have been replaced. In embodiments, all or substantially all of the cpmA & cpmB and ptiB, have been replaced. This SaPI2 derivative is used in the following embodiments, and is diagrammed in FIGS. 3B & 4 to illustrate what is referred to herein as the "basic SaPI2 derivative".

An embodiment by which the basic SaPI2 derivative can block the expression of virulence by an infecting organism, (see FIG. 10) includes three insertions: an autoinduction circuit comprising *S. warneri* agrB & agrD plus *B. subtilis* comA & a comP-agrC hybrid, driven by *B. subtilis* promoter, PcomQ which will produce an auto-inducing peptide (AIP) that inhibits activation of the virulence-controlling agr locus, the 3' segment of RNAIII, an antisense RNA targeting spa (he gene for staphylococcal protein A) which will enhance the anti-virulence activity of the inhibitory AIP, and an anti-sense RNA against agrA, which will block expression of certain other virulence genes.

In a separate embodiment designed to block biofilm formation, rsbW, a protein that blocks the activity of sigmaB plus the gene for IcaR, the repressor of the ica operon, will both be inserted into the basic SaPI2 derivative. This modification of the basic SaPI2 derivative is expected to be useful in the treatment of foreign body infections.

In a further embodiment, designed to kill the infecting bacteria, the genes encoding the secreted proteins, PezA, which blocks the synthesis of the staphylococcal cell wall, GhoT, a membrane poison, or lysostaphin, or any combination of the three, can be inserted into the basic SaPI2 derivative. PezA or GhoT will not only kill the infecting staphylococci but will also activate the bacterial SOS response, which will induce resident staphylococcal prophages as well as the SaPI-carried dut gene. Lysostaphin, a powerful staphylolytic enzyme, will destroy not only the ABD-infected staphylococci but also any surrounding bacteria that have not been directly infected.

The Dut protein, dUTPase, will derepress SaPI2 replication enabling SaPI packaging by any resident prophage, and spread of the SaPI to any residual staphylococci in the animal. In a further embodiment, an antisense RNA complementary to the translational start of the secY gene will be inserted. This will also kill the target organism by blocking expression of the essential secY gene. These 3 insertions will effectively eliminate the occurrence of mutants resistant to the ABD.

In a further embodiment, an ABD can be used as a probiotic agent, separately from an anti-infective ABD.

In an embodiment, an ABD expressing a secreted antibacterial protein can be inserted into a non-pathogenic bacterium that is co-resident within the body, and wherein a pathogenic bacterium that the non-pathogenic bacterium will kill or inhibit may also be present. An example comprises arming a probiotic *lactobacillus* with an ABD that expresses a bacteriocin that kills enterocolitis-causing *Clostridium difficile* in the large intestine.

In another approach the basic SaPI2 derivative is modified by the insertion of a CRISPR/Cas9 cassette. This cassette contains a spacer specific for a bacterial gene or other bacterial sequence and will kill the target organism by introducing a double-strand break in its DNA.

A variation of this embodiment is the insertion of a CRISPR/dcas9 cassette into the basic SaPI2 derivative containing one or more spacers specific for the regulatory regions of bacterial genes required for growth, viability, or the expression of virulence genes.

The disclosure, as illustrated in part by the figures, includes derivatives of the CRISPR/cas9-containing molecule in which the spacer has been replaced by a new spacer specific for the agrA gene of *S. aureus*, which is highly conserved among all staphylococci and several other Gram-positive species, or by a new spacer targeting the mecA gene, which is required for methicillin resistance in MRSA and is present only in MRSA strains. Other examples include but are not limited to replacement of the spacer with any gene present in some but not other strains.

Embodiments of this disclosure, as illustrated in part by the figures, relate to derivatives of the CRISPR/dcas9-containing derivatives of the basic SaPI2 derivative wherein the CRISPR array contains spacers derived from any bacterial or inserted element sequences, including but not limited to spacers which will block the expression of host virulence genes, biofilm genes or regulatory genes. One example is a spacer targeting S. aureus gene agrA. Another example is three spacers targeting S. aureus genes Pica, Psrt &PfnbA, respectively. A third example includes 3 spacers targeting S. aureus promoters agr-p2-p3, Pspa &PfnbA, respectively.

In a further embodiment, all of the above derivatives of the basic SaPI2 derivative can be inserted into the genomic DNA of a derivative of S. aureus strain RN450 lysogenic for a derivative of bacteriophage 80α with a deletion of its small terminase subunit (terS) gene. In an alternative embodiment, all of the above derivatives of the basic SaPI2 derivative can be inserted into the genomic DNA of a derivative of S. aureus strain RN450 containing a part of the 80α prophage consisting of the SaPI2 de-repressor, the virion genes and the lysins, the first two being driven by the strong but inducible Ptet promoter, and the lysin genes driven by the inducible Pbla promoter. In further embodiments, all of the above derivatives of the basic SaPI2 derivative can be inserted into any staphylococcal strain or any bacterial strain.

An aspect of this disclosure is the use of any molecule derived from any SaPI-like element in bacteria by the insertion of cloned bacterial or bacteriophage genes or any CRISPR array packaged in a bacteriophage-like particle and directed toward disrupting a bacterial infection.

An alternative approach comprises use of the basic SaPI2 derivative, modified by the insertion of a CRISPR/cas9 module with a conserved chromosomal gene-specific spacer, as an anti-staphylococcal or antibacterial gene drive. In this embodiment, the CRISPR/cas9—containing molecule can be inserted into the chromosome of an attenuated S. aureus strain with deletions of its agr, spa, hla and sae genes and containing prophage 80α.

In further embodiments, the ABD system can be modified to enable it to be used therapeutically against infections with other Gram-positive bacteria. Those skilled in the art, given the benefit of this disclosure, will recognize that these illustrative examples include a multitude of variations. For example, in embodiments the CRISPR/cas9 modules can contain spacers targeting the conserved dnaA or any other conserved gene of any of the following organisms: L. monocytogenes, E. faecalis S. pyogenes, S. pneumoniae, and C. difficile.

A variant of this embodiment can utilize a CRISPR/dcas9 module with different spacers, each targeting a gene essential for the virulence of each of the same 5 organisms, specifically, spacers targeting the Pllo promoter of L. monocytogenes, the PgelE promoter of E. faecalis. PcovA promoter of S. pyogenes, the Pwzg promoter of S. pneumoniae, or the Ptxa promoter of C. difficile.

It is considered that these embodiments can be extended to include any members of the entire pathobiological bacterial spectrum. In particular, for each bacterial pathogen to be targeted, an attenuated or non-pathogenic bacterial strain can be developed, containing a CRISPR/Cas9 derivative with one or more spacers targeting one or more genes or other sequences of the targeted bacterial species. These embodiments can utilize any SaPI or SaPI-like element in bacteria, or derivative thereof coupled with any prophage or prophage derivative.

In one embodiment, a solution is provided containing SaPI2 particles harboring S. warneri agrB, agrD, and the 5' half of agrC, B. subtilis comA and the 3' half of comP, rsbW, the anti-spa segment of RNAIII, anti-sense agrA and secY have been inserted (ABD2012—see Table 3). The S. warneri AIP inhibits activation of the agr locus in all known staphylococci. Expression of agrB & D will be driven by an autoinduction circuit composed of the B. subtilis ComAP signal transduction module driven by the comQ promoter. This construct is designed to sharply attenuate the virulence of infecting S. aureus bacteria. $10^{10}$/ml in sterile buffered saline for IV injection in mice or $3\times10^{12}$for IV injection in humans. In this formulation, rsbW will block SigB function and thus prevent biofilm formation. AgrB & D will combine to produce and secrete an inhibitory AIP that will block the expression of the endogenous agr locus in the infecting bacteria and in any neighboring bacteria that have not been infected by the SaPI; anti-Pspa RNAIII will block translation of staphylococcal protein A. Anti-agrA will block expression of the phenol-soluble modulins. Anti-secY will block expression of secY, essential for protein secretion and for viability. This combination will severely attenuate the virulence of the infecting bacteria. Resident prophages, induced spontaneously will package the ABD DNA, enabling its spread to any bacteria that were not infected by the initial dose of ABDs.

In another embodiment, a solution is provided containing SaPI2 particles carrying genes for the anti-staphylococcal toxins PezT and GhoT, $10^{10}$/ml in sterile buffered saline for IV injection in mice or $3\times10^{12}$for IV injection in humans. This formulation is designed to block the growth and likely kill the infecting organisms by interfering with cell wall synthesis and by disrupting the integrity of the bacterial cytoplasmic membrane.

In another embodiment, a solution is provided containing SaPI2 particles carrying the gene for the secreted staphylolytic enzyme, lysostaphin, $10^{10}$/ml in sterile buffered saline for IV injection in mice or $3\times10^{12}$for IV injection in humans or the bovine udder. This formulation is intended destroy the infecting organisms by degrading their cell walls.

In another embodiment, a solution is provided containing SaPI2::CRISPR/Cas9(agrA-spacer) particles. This formulation is designed to kill the targeted organisms by introducing a DSB in the chromosomal DNA. The DSB will induce resident prophages, which will package the SaPI and lyse the bacterium, enabling the SaPI to spread to any bacteria not originally infected by it.

In another embodiment, a solution is provided of SaPI2::CRISPR/dCas9(agr-$P_2P_3$; Pspa PfnbA spacers) particles, $10^{10}$/ml in sterile buffered saline for IV injection in mice or $3\times10^{12}$ for IV injection in humans. This formulation is designed to disarm the organism by blocking the expression of the key virulence genes up-regulated by agr and the expression of spa and fnbA, virulence genes that are down-regulated by agr.

In another embodiment, a solution is provided of SaPI2::CRISPR/dCas9(Pica, PfnbA and Psrt spacers) particles, $10^{10}$/ml in sterile buffered saline for IV injection in mice or $3\times10^{12}$ for IV injection in humans. This embodiment is designed for the blockage of biofilm formation by staphylococci.

In another embodiment, a solution is provided containing a mixture of two or more types of the particles described in the first 3 embodiments above, $10^{10}$/ml each, in sterile buffered saline for IV injection in mice or $3\times10^{12}$/ml each for IV injection in humans.

Exemplary embodiments are directed toward infections by other Gram-positive bacteria. In one embodiment, a solution is provided of SaPI2::CRISPR/Cas9(DnaA spacer) particles, $10^{10}$/ml in sterile buffered saline for IV injection in mice or $3\times10^{12}$ for IV injection in humans. In this embodiment, for treatment of Listeria infections, the DnaA spacer is from L. monocytogenes and this formulation is designed to kill the organism by introducing a chromosomal DSB.

In another embodiment, a solution is provided of SaPI2::CRISPR/dCas9(Pllo spacer) particles, $10^{10}$/ml in sterile buffered saline for IV injection in mice or $3\times10^{12}$ for IV injection in humans.

In another embodiment, a solution is provided of EfCIV583::CRISPR/Cas9(DnaA spacer) particles, $10^{10}$/ml in sterile buffered saline for IV injection in mice or $3\times10^{12}$ for IV injection in humans. In this embodiment, the dnaA spacer is from Enterococcus faecalis and the CRISPR-containing particles are targeted at infecting E. faecalis or E. faecium and administering a lethal DSB.

In another embodiment, a solution is provided of EfCIV583::CRISPR/dCas9(PgelE spacer) particles, $10^{10}$/ml in sterile buffered saline for IV injection in mice or $3\times10^{12}$ for IV injection in humans. In this embodiment, the spacer targets the E. faecalis gelE promoter, required for virulence, and attenuates E. faecalis or E. faecium infections.

In another embodiment, a solution is provided of SpnCI-ST556::CRISPR/Cas9(DnaA spacer) particles, $10^{10}$/ml in sterile buffered saline for IV injection in mice or $3\times10^{12}$ for IV injection in humans. In this embodiment, the CRISPR-containing particles are targeted at infecting Streptococcus pneumoniae, and administering a lethal DSB.

In another embodiment, a solution is provided of SpnCI-ST556::CRISPR/dCas9(Pwzg spacer) particles, $10^{10}$/ml in sterile buffered saline for IV injection in mice or $3\times10^{12}$ for IV injection in humans. The Pwzg spacer corresponds to a motif in the promoter of a gene that is required for capsule biosynthesis and is conserved throughout the pneumococci; in this embodiment, the CRISPR-containing particles are thus targeted to capsular synthesis by any infecting Streptococcus pneumoniae. This will render the organism avirulent and cure the infection.

In another embodiment, a solution is provided of SpyCI-NZ131::CRISPR/Cas9(DnaA spacer) particles, $10^{10}$/ml in sterile buffered saline for IV injection in mice or $3\times10^{12}$ for IV injection in humans. In this embodiment, the CRISPR-containing particles are targeted at infecting Streptococcus pyogenes and administering a lethal DSB.

In another embodiment, a solution is provided of SpyCI-NZ131::CRISPR/dCas9(PcovA spacer) particles, $10^{10}$/ml in sterile buffered saline for IV injection in mice or $3\times10^{12}$ for IV injection in humans. In this embodiment, the CRISPR-containing particles are targeted at infecting Streptococcus pyogenes and attenuating virulence of the organism.

Additional aspects of this disclosure relate at least in part to the properties of many of the SaPIs to carry the genes for superantigen toxins and other virulence factors. For example, SaPIs are the only known reservoir of the gene for toxic shock syndrome toxin (TSST-1), which they disseminate widely among S. aureus strains, and therefore are of considerable clinical interest. For the purposes of this disclosure, which in certain embodiments relates to SaPI2, the TSST-1 gene, as well as the SaPI2-carried gene for exfoliatin, the scalded skin syndrome toxin, have been deleted. The disarmed SaPI2 can be engineered to carry the SaPI2 anti-repressor, dut, which will facilitate spread of the SaPI among infecting bacteria, and therapeutic genes described below. Diagrams of the SaPI2 genome and its derivatives are presented in FIG. 4 and Table 3. Other aspects of the disclosure include using and/or modifying any one or combination of the following genetic elements to, for example, modify a SaPI2 genome to replace toxin genes. The sequences of each of these genes is well known in the art and can be readily accessed by the skilled artisan.

Dut encodes the phage dUTPase, a dual function protein that, in addition to its classical enzymatic activity, doubles as the anti-repressor protein for SaPI2, and several other SaPIs. In this system dut is driven by PuvrB, an SOS-inducible promoter. Dut will be expressed following spontaneous SOS induction, resulting in autonomous replication of the island. Virtually all staphylococci are lysogenic, many carrying several prophages. Although the prophage state is stable and long-lasting, individual cells undergo spontaneous prophage induction in vitro at frequencies of $10^{-3}$-$10^{-5}$/per cell generation and these frequencies are probably greater in vivo. Any prophage undergoing spontaneous induction will package a de-repressed SaPI, such as SaPI2, whether or not it is a SaPI2 helper, as well as its own genome, and will release SaPI2 as well as infective phage particles following lysis of that cell. (The infective phage particles will be non-functional since the neighboring cells will be immune as lysogens). This will enable SaPI2 to spread to any other staphylococci that were not initially infected by SaPI2, and repeat the process.

Among the therapeutic genes that can be inserted into the SaPI2 genome in place of the toxin genes are the AIP-producing agrB & D genes and the anti-spa segment of RNAIII.

AgrB & D combine to produce the thiolactone-containing autoinducing peptide molecule that is the activating ligand for the agr signal transduction—quorum-sensing system. The agr locus is conserved throughout the staphylococci and the AIPs produced by most non-aureus staphylococci are potent inhibitors of agr expression in S. aureus. One of these, produced by S. warneri, is a universal inhibitor of all four known S. aureus agr alleles and will be incorporated in the ABD system. S. warneri AgrB&D will be driven by an autoinducing circuit involving the B. subtilis comAP locus (see FIG. 10) and in this invention will generate and secrete the inhibitory S. warneri AIP, which will diffuse and block the expression of the agr locus belonging to any infecting S. aureus, including not only that being targeted by the ABD, but any other S. aureus bacteria in the animal.

Anti-spa segment of RNAIII. RNAIII is a regulatory RNA molecule that is the effector molecule of the staphylococcal agr quorum sensing system, which regulates staphylococcal virulence. RNAIII carries out most of the regulatory function of the agr system. It contains several stem-loops that are designed to pair with the translation-initiation signals of the virulence genes that it regulates, thus blocking their translation. During the exponential phase of growth, it down-regulates many of genes that are required for the establishment of an infection, including the adhesins and anti-immunity genes, especially spa (staphylococcal protein A), specifically down-regulated by the 3' stem-loop of RNAIII Protein A protects the organism from opsonization and therefore has a major role in the initiation of infection.

Anti-sense RNA against agrA. Since agrA has its own promoter which is activated in vivo, and since AgrA directly activates certain virulence genes, blocking overall agr expression by an inhibitory AIP will not be sufficient to fully attenuate virulence. Accordingly, an anti-sense RNA directed against agrA translational start can be included.

Anti-sense RNA against secY. SecY is an essential gene for which antisense RNA against its translational start has been shown to effectively inhibit cell growth.

RsbW. RsbW blocks the function of the alternative RNA-polymerase sigma subunit, sigB, which is involved in many stress-induced gene functions in staphylococci, especially including biofilm formation. As biofilm formation is an important aspect of staphylococcal infections, especially those involving surgical implants, blockage of biofilm formation is an important aspect of anti-staphylococcal therapy.

IcaR. IcaR is the repressor of the staphylococcal ica locus, which contains several genes involved in the synthesis of the intracellular adhesin that is required for biofilm formation. Blockage of this locus by the ABD-carried repressor will prevent biofilm formation.

PezT and GhoT. PezT and GhoT are the toxin components of bacterial toxin-antitoxin (TA) systems, which act by blocking cell wall synthesis and by disrupting the bacterial cellular membrane potential, respectively. Either will kill or strongly inhibit any infecting staphylococcus. Production of ABDs containing these toxins can be achieved by equipping the ABD-producing strain with the respective antitoxins. Those skilled in the art will recognize that the foregoing represent non-limiting examples, but the possible alternatives are limited only by the size of the DNA to be packaged by the SaPI system. CRISPR/Cas9. A highly versatile gene editing system known as the CRISPR/Cas9 system has recently been developed and is now in worldwide use, largely for modifying human, plant, or animal genes. CRISPR stands for clustered regularly interspaced short palindromic repeats and Cas9 stands for CRISPR-associated protein 9, a key component of the type II CRISPR system. The system was originally discovered as an adaptive immune system for bacteria and archaea. Its function is well known. Briefly, when foreign DNA, e.g., DNA of a bacterial virus enters the bacterial cell, a short segment of that DNA is incorporated into the CRISPR array as a new spacer. This process is diagrammed in FIG. 6. Although most of the phage-infected cells are killed in a natural setting, a few survive, containing the phage DNA segment in their spacer array. If that cell or any of its descendants is then infected by the same or a closely related bacteriophage, the spacer in the cell's CRISPR array specific for that phage plus the adjacent upstream repeat is transcribed into a small RNA molecule which is paired with another small RNA and the complex then binds to both the Cas9 protein and also to the corresponding segment of the phage DNA. This brings the Cas9 protein into direct contact with the targeted phage DNA where it introduces a double-stranded cut into the phage genome, effectively destroying the phage DNA.

Once this mechanism was determined, it became evident that any DNA segment could be introduced by recombinant DNA methods as a spacer in the CRISPR array, enabling the CRISPR to target and cut any arbitrarily chosen DNA. In addition to introducing SaPI2-linked genes that impact the spread of SaPI2 and the virulence or survival of the organism, we have engineered CRISPR/Cas9 functionality into SaPI2. In most bacteria or any bacterial DNA element, a double-stranded cut is lethal. Thus, in some of the embodiments of this disclosure, a DNA segment corresponding to a bacterial gene is incorporated into a CRISPR array. This array is then cloned by recombinant DNA methods into SaPI2 or a similar mobile element. Any bacterial cell infected by a SaPI containing a CRISPR/Cas9 segment with a spacer corresponding to any chromosomal gene will suffer a lethal DSB in the targeted gene. This DSB will activate the SOS response, inducing any resident prophages. The dut gene carried by the SaPI may also be induced so that the SaPI DNA will replicate, will be encapsidated by an induced prophage, and thus enabled to spread to any other infecting cells.

Figure 18:
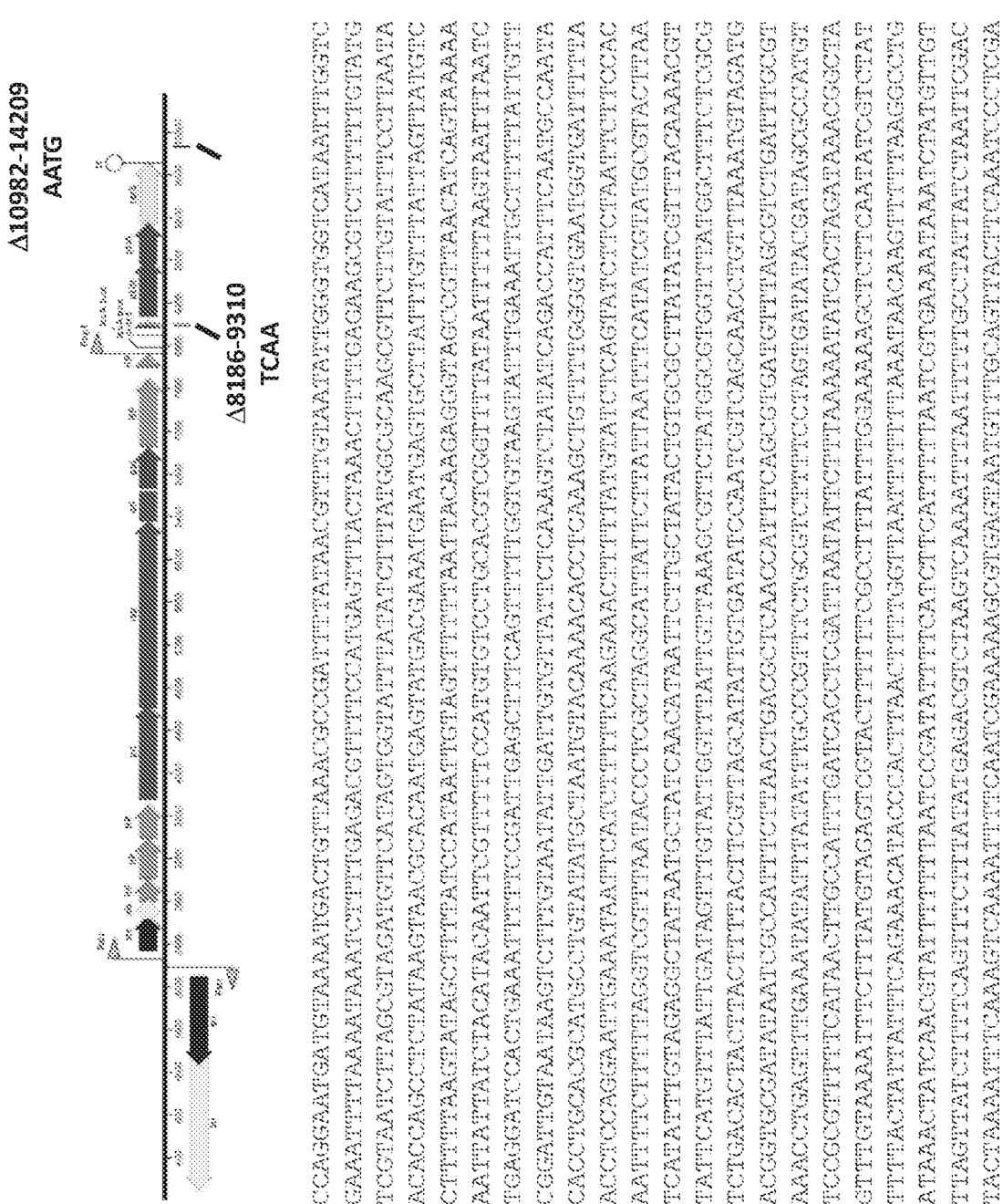
FIG. 18. SaPI2 representative sequences to illustrate incorporation of CRISPR/Cas9 segment into an ABD of this disclosure. Interpretation of the sequences is aided by the schematic genetic element maps of SaPI2 with deletions as indicated (the sequence includes precise locations which are enlarged and italicized). The deletion from nucleotides 8136-9210 removes the 3 genes, ptiB, cpmA and cpmB; the sequence from 10982-14209 removes the virulence genes, tst and eta. The second deletion is the site into which the tetM gene and the CRISPR/cas9 module were inserted, resulting in ABD2002, as in the diagram. The CRISPR/cas9 segment contains the CRISPR array, the cas9 gene and the tracr RNA gene. The tracr RNA pairs with the spacer RNA (crRNA) to form the guide RNA complex, which binds to the Cas9 protein and directs it to the spacer-determined target site.
Figure 19:
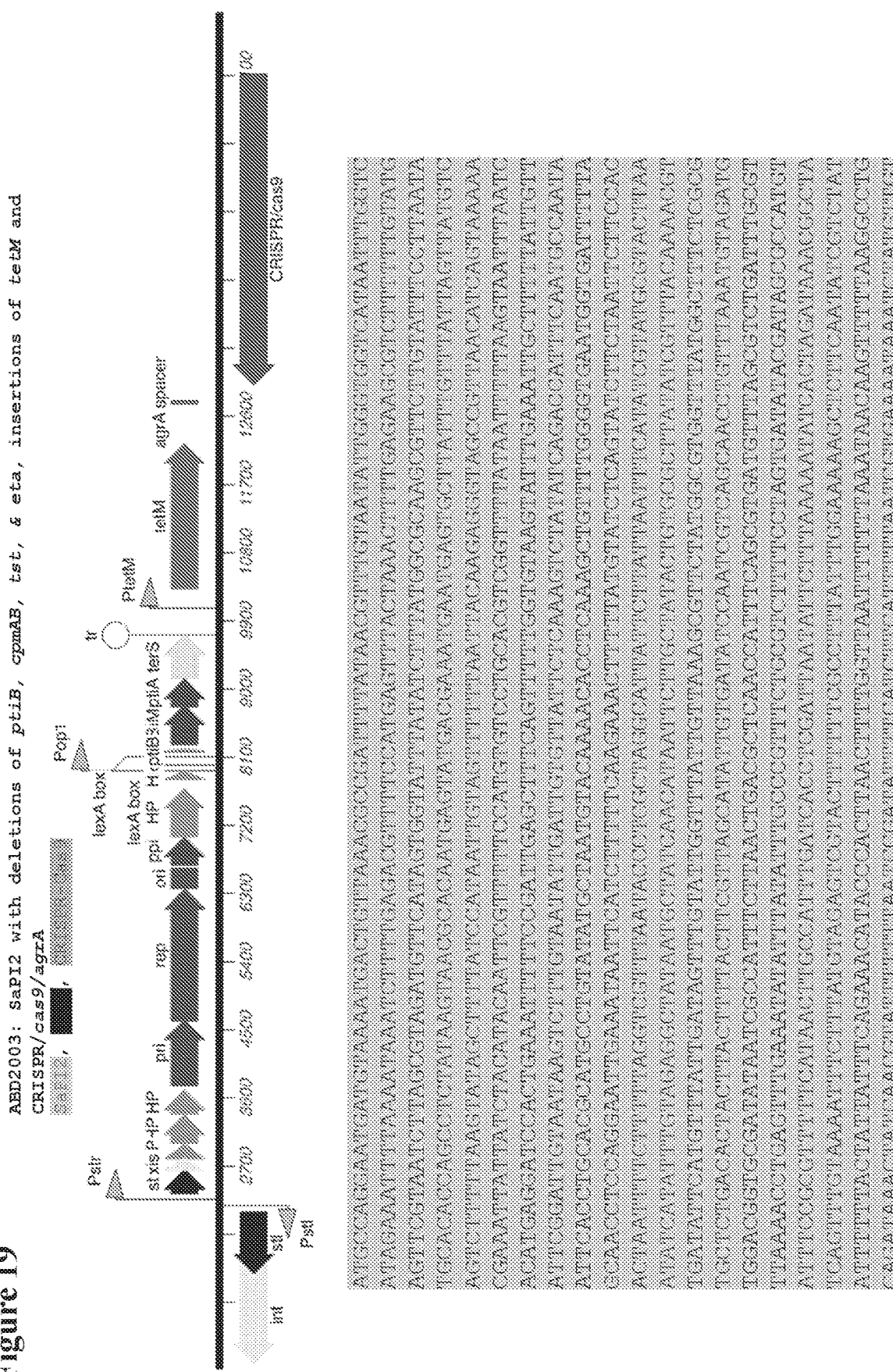
FIG. 19. Sequences and diagram illustrating representative SaPI2 CRISPR/cas9 construct, related to FIG. 18. Color of sequence is as designated in the legend above the diagram.
Figure 20:
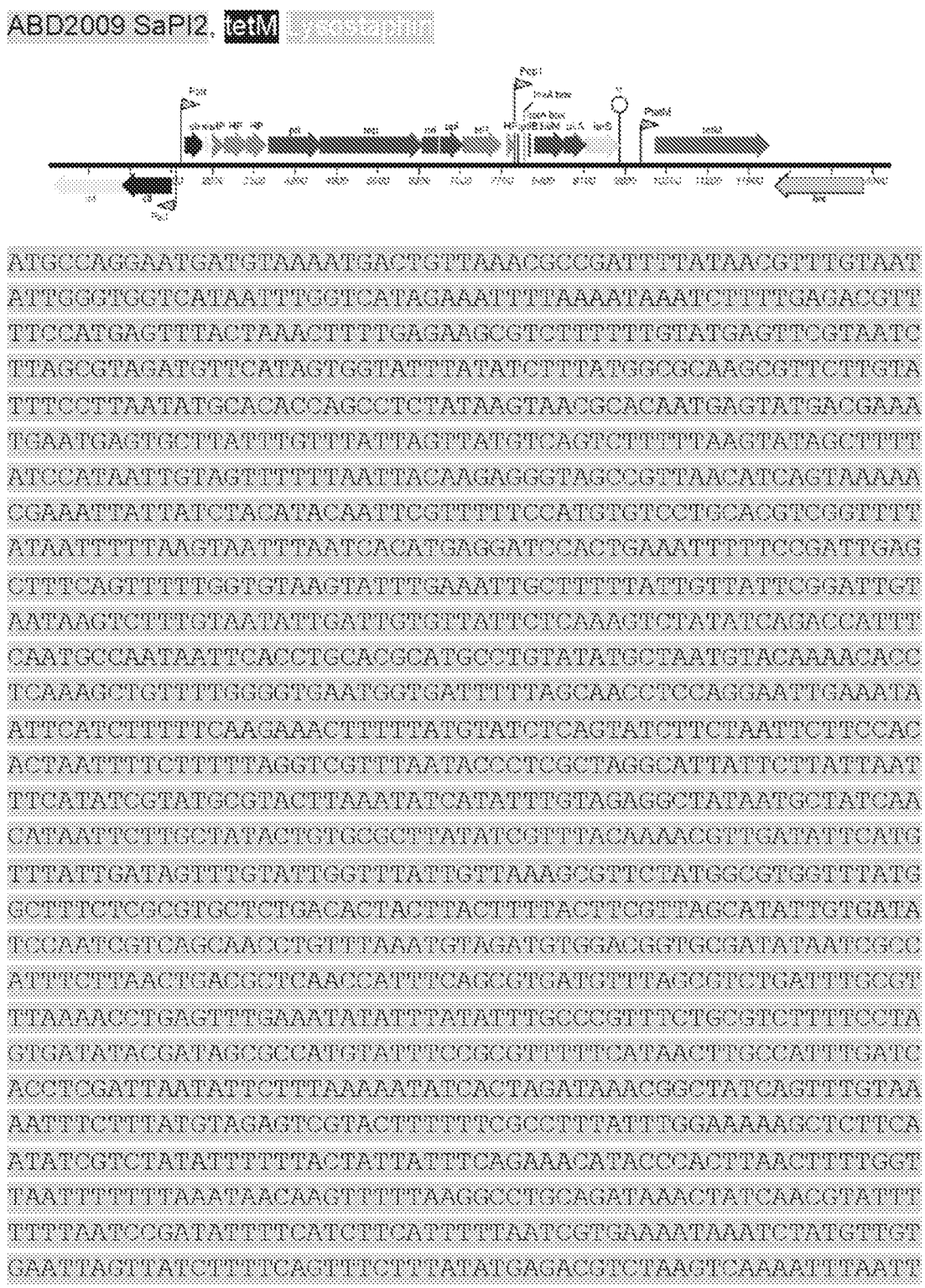
FIG. 20. Sequences and diagram illustrating representative lysostaphin gene construct, related to ABD2009.

In certain non-limiting approaches, SaPI2 representative sequences depicted in FIG. 18 (SEQ ID NO:2) and FIG. 19 (SEQ ID NO:3) provide non-limiting illustrations of sequences that show incorporation of CRISPR/Cas9 segment into an ABD of this disclosure. Interpretation of the sequences is aided by the schematic genetic element maps of SaPI2 with deletions as indicated by comparison of FIGS. 18 and 19 (sequences show certain annotated and precise locations which are enlarged and italicized). Color coding of sequences is as described in the figure descriptions and in the figures. The deletion from nucleotides 8136-9210 removes the 3 genes, ptiB, cpmA and cpmB; that from 10982-14209 removes the virulence genes, tst and eta. The second deletion is the site into which the tetM gene and the CRISPR/cas9 module were inserted, resulting in ABD2002, as in the diagram of FIG. 18. The CRISPR/cas9 segment contains the CRISPR array, the cas9 gene and the tracr RNA gene. The tracr RNA pairs with the spacer RNA (crRNA) to form the guide RNA complex, which binds to the Cas9 protein and directs it to the spacer-determined target site.

An alternative strategy to CRISPR/Cas9 killing involves a modified CRISPR/Cas9 system in which the nuclease activity of Cas9 has been eliminated by mutation. This Cas9 derivative, known as dCas9, retains its full ability to bind tightly to any DNA to which it is targeted by a spacer-coded RNA. This tightly bound dCas9 can block expression of the targeted gene, whether it is bound to the coding sequence or to the 5' regulatory region of the gene. In these embodiments, the cell is not killed but can be strongly attenuated for virulence by dCas9 binding to virulence genes or their regulators. In some of the embodiments, the dCas9 is targeted to several different genes simultaneously by having corresponding spacer constructs in its CRISPR array. In one embodiment, these several genes are involved in virulence; in another, they are involved in biofilm formation. A variety of combinations is included by the disclosure: two different CRISPR arrays on separate SaPI derivatives can simply be mixed for administration, or they can both be present on a single SaPI, or they can all be present in a single CRISPR array.

Among the therapeutic genes that have been inserted into the SaPI2 genome as spacers in the CRISPR array are the following:

AgrA. The agr system is a widespread global genetic regulatory system in Gram-positive bacteria, first discovered in *S. aureus* and extensively characterized in that species—see FIG. 9 for a genetic diagram. The agr locus contains a 2-component signal transduction circuit, of which AgrC is the receptor and AgrA the response regulator, which is activated by a small peptide (AIP) processed from AgrD by AgrB. AgrA binds to and activates its own promoter, $P_2$, setting up a positive feedback loop, and also to the adjacent and divergent promoter, $P_3$, whose transcript, RNAIII, is a regulatory RNA that is the primary effector molecule of the regulatory system. AgrA is absolutely conserved within the staphylococci so that its use as a spacer enables the CRISPR/Cas9-mediated killing of any staphylococcal strain or species.

lsp. The gene for lysostaphin, a powerful lytic enzyme that destroys staphylococcal cells by degrading the cell wall. This is envisioned especially for bovine mastitis, which is largely intractable because it responds poorly to antibiotics.

fib. The gene for staphylococcal fibrinogen binding protein, a highly conserved but non-essential gene whose incorporation as a spacer in the ABD CRISPR/cas9 array will enable killing of virtually all *S. aureus*. The incorporation of 2 separate spacers in the array will largely eliminate the problem of CRISPR resistance.

$P_2$—$P_3$. The intergenic region between agrB and RNAIII (see FIG. 9), containing the agr promoters $P_2$ and $P_3$, is used as a binding target for dCas9, which thus blocks expression of the entire agr regulon, including many virulence genes. This attenuates staphylococcal virulence by about 100-fold.

Pspa is the protein A promoter. Targeting of Pspa by dCas9 blocks transcription of spa.

PfnbA is the fibronectin binding protein A (FnbA) promoter. Targeting of PfnbA by dCas9 blocks transcription of fnbA. FnbA is a major staphylococcal adhesin having a key role in the localization and stabilization of the organism during the establishment of an infection, and serves as the primary adhesin for biofilm formation.

Pica is the promoter for the intercellular adhesin (ica) gene. Ica is the intercellular polysaccharide adhesin, also known as "slime", which is required for biofilm formation. The formation of a robust biofilm requires FnbA to enable adhesion to the substrate plus Ica to enable the massive buildup of structured cellular layers and protect the cells from host immunity and many antibiotics.

Psrt is the sortase promoter. Targeting of Psrt by dCas9 blocks transcription of srt. Since sortase is the major enzyme that anchors outer surface bacterial proteins to the peptidoglycan of the bacterial cell wall, bacteria lacking sortase are deprived of their outer surface proteins, which causes them to be seriously compromised in their ability to initiate and sustain an infection and to resist innate immunity.

The above genes are exemplary—many other genes could be used and are encompassed by this disclosure. A few non-limiting examples of genes that would act against other Gram-positive bacteria are listed below.

DnaA is the universal initiator for bacterial chromosome replication and is a target for a DSB-inducing spacer.

Pllo is the promoter of the gene for listeriolysin O, a lytic enzyme that enables *L. monocytogenes* to spread between cells. Blocking this promoter will prevent llo expression, which will abrogate a *L. monocytogenes* infection.

PcovA is the promoter for covA, a global regulator of *S. pyogenes* virulence. Blocking this promoter will prevent covA expression, which will sharply attenuate an infection.

PgelE is the promoter for gelE, which encodes a gelatinase enzyme that is necessary for enterococcal virulence.

Pwzg is the promoter for the pneumococcal capsule regulatory gene, wzg, and has a motif absolutely conserved among the pathogenic pneumococci. Blockage of the expression of this gene prevents capsule formation and renders the organism totally avirulent.

Helper phage modification. In order to enhance the production of infectious SaPI2 particles, we have modified the helper phage 80α as follows: i) deletion of the terminase small subunit (terS) gene, which will eliminate its ability to package its own (phage) DNA so that only SaPI-containing particles are produced, generally at a frequency of >$10^9$/ml of culture; ii) an alternative strategy involves a major deletion of helper prophage genes so that the prophage element contains only the SaPI de-repressor gene, dut, the entire set of virion genes and the lysins. To maximize SaPI particle production, the dut and virion modules are driven by the strong but inducible Ptet promoter, and the lysin genes driven by the inducible Pbla promoter—which will enable lysis to be delayed until the cell is filled with SaPI particles. With this alternative, no phage DNA is produced at all. Modifications to enable adsorption and gene expression in diverse bacterial hosts will permit the SaPI strategy to be applicable to diverse bacterial pathogens.

Spread of the SaPI2 particles. With respect to the staphylococci, all known clinical isolates are lysogenic and most carry 2 or more prophages. All known functional prophages undergo spontaneous induction owing to stochastic triggering of the SOS (DNA damage) response. This occurs in ~1 in 1,000 or 10,000 cells so that any culture contains considerable numbers of free phage particles. In addition, a CRISPR-induced DSB is will induce the SOS response to DNA damage, which will increase the induction of resident prophages. A SaPI infecting a strain that is lysogenic for a helper phage will then be spread to neighboring cells as a consequence of spontaneous or induced prophage induction with the concomitant production of SaPI particles. Since the primary role of a helper phage is to relieve repression of the SaPI, it follows that if a SaPI is spontaneously de-repressed, it can be packaged and transferred by any co-resident phage, whether or not it is a helper. This will apply to any incoming SaPI2 of this invention since it will carry the antirepressor gene, dut.

It will be recognized from the foregoing, but without intending to be bound by any particular theory, that it is considered that the present SaPI-based approach has the following advantages over phage-based approaches: i) phages have a very limited capacity for genome expansion (about 3 kb for coliphage λ), whereas the present modified SaPI2 genome can be expanded by ~30 kb—which is sufficient room for a wide variety of additions; ii) SaPIs intrinsically have a much greater host range than phages, which would be of concern for many types of phage therapy; iii) with SaPIs, there are a wide variety of options for interfering with a bacterial infection; with phages, options are limited to direct killing of the bacteria, which is highly selective for resistance. iv) A version of the ABD, ABD2002, can be adapted to provide an autoinduction circuit that produces an inhibitory AIP that will block the virulence of any *S. aureus* bacteria present in an infected animal.

TABLE 3

Representative ABDs

| SaPIs and ABDs | Size, Kb | Deletions | Insertions | Function |
|---|---|---|---|---|
| Demonstrated | | | | |
| SaPI2 (WT) | 15.7 | | | |
| ABD2001 | 12.5 | cpmA&B | tst eta tetM | ABD backbone |
| ABD2002 | 17.6 | cpmA&B | tst eta tetM CRISPR/cas9/non-targeting | Generic CRISPR/cas9 |

TABLE 3-continued

Representative ABDs

| SaPIs and ABDs | Size, Kb | Deletions | Insertions | Function |
|---|---|---|---|---|
| ABD2003 | 17.6 | cpmA&B tst eta | tetM CRISPR/cas9/agrA | Causes lethal double-strand break (DSB) in agrA |
| ABD2004 | 17.6 | cpmA&B tst eta | tetM CRISPR/cas9/hly | Causes lethal DSB in hly (listeriolysin O) |
| ABD2005 | 17.6 | cpmA&B tst eta | tetM CRISPR/dcas9/non-targeting | Generic CRISPR/dcas9 |
| ABD2006 | 17.6 | cpmA&B tst eta | tetM CRISPR/dcas9/agrP$_2$P$_3$ | Blocks virulence by inhibiting expression of agr locus |
| ABD2007 | 17.7 | cpmA&B tst eta | tetM CRISPR/cas9/fib | Causes lethal double-strand break (DSB) in fib |
| ABD2008 | 17.8 | cpmA&B tst eta | tetM CRISPR/cas9/agrA/fib | Causes lethal double-strand break (DSB) in agrA and fib |
| ABD2009 | 14.0 | cpmA&B tst eta | tetM lsp | Secretes lysostaphin, lyses ABD-infected and surrounding uninfected |
| Included | | | | |
| ABD2010 | 19.0 | cpmA&B tst eta | tetM CRISPR/cas9/agr; lsp | Causes lethal double-strand break (DSB) in agrA; lyses all cells |
| ABD2011 | 14.5 | cpmA & B tst eta | dut* tetM | replicates autonomously |
| ABD2012 | 18.3 | cpmA & B tst eta | dut tetM, hybrid agr-com, anti-spa RNAIII, anti-agrA, anti-secY | replicates autonomously; blocks agr, spa, PSMs, secY expression |
| ABD2013 | 14.9 | cpmA & B tst eta | dut tetM rsbW icaR | replicates autonomously; blocks biofilm formation |
| ABD2014 | 16.2 | cpmA & B tst eta | tetM pezT ghoT | Kills ABD-infected staphyloocci |

*Constructs made both with and without dut are included in the disclosure.

The following Example 1 is intended to illustrate, but not limit the invention.

Example 1

Material and Methods for Construction of the ABDs

Standard bacteriologic methods are adapted for use in this disclosure. Bacteria are cultured on trypticase-soy (TSB) agar with erythromycin, tetracycline or chloramphenicol, each at 5 μg/ml, as needed, or in TSB broth. Phages and SaPIs are enumerated by dilution and plating for plaque or colony formation, respectively, with suitable indicator strains, as discussed above. Phage or SaPI lysates are prepared by mitomycin C (2 μg/ml) induction in CY broth with slow shaking at 32° C. Lysates are centrifuged at 10,000 rpm for 10 min, treated with DNAase and RNAase for 3 h at 37° C., then filter-sterilized with a 0.22 μMillipore filter. Lysates are concentrated by precipitation with PEG-8000 (10%)+NaCl (0.5M) for 18 h at 4° C., then centrifuged at 9,000 rpm for 15', and resuspended in $\frac{1}{100}$ volume of phosphate-buffered saline (PBS). Particles are further purified by centrifugation through a CsCl step gradient followed by dialysis against phage buffer.

Figure 11:
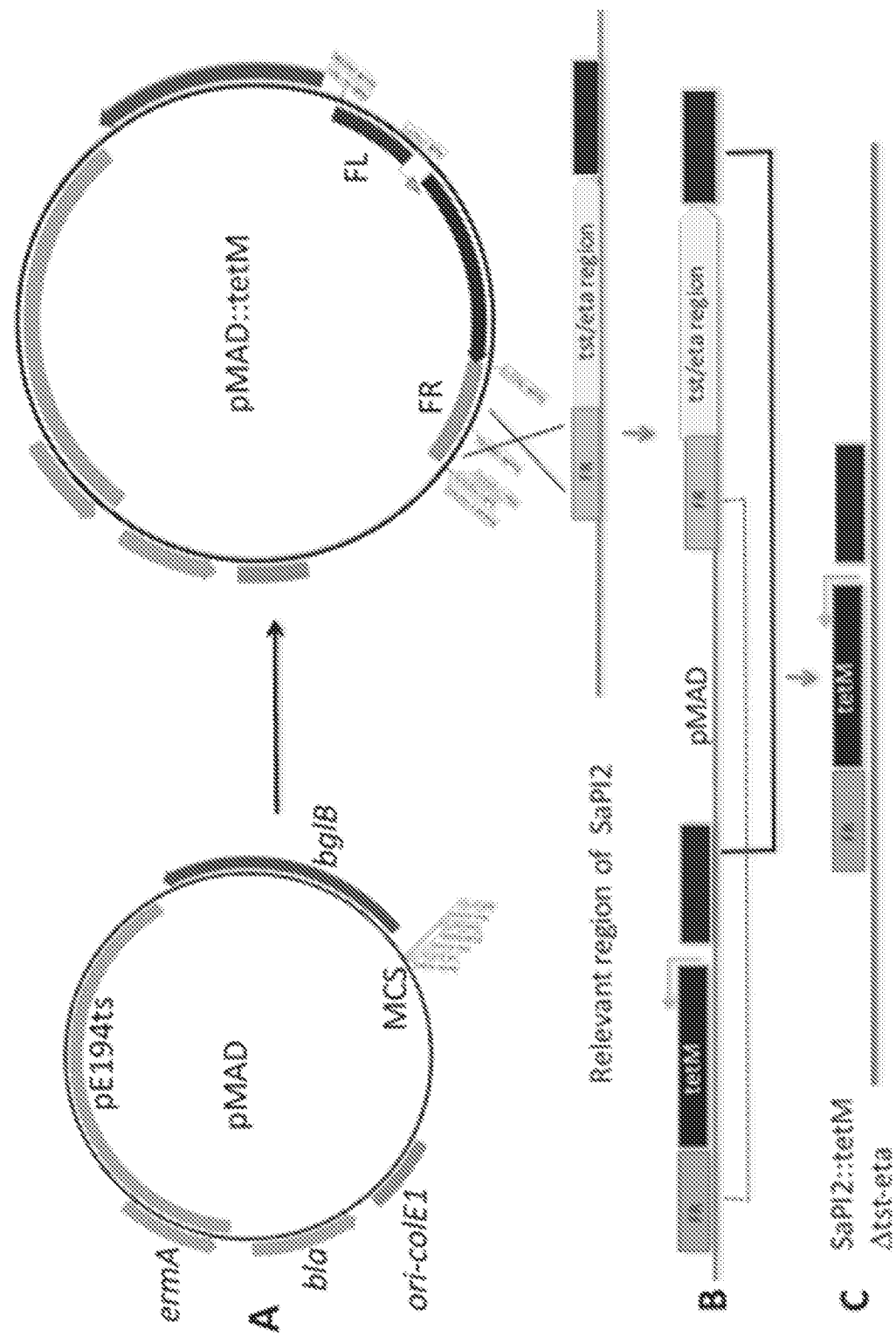
FIG. 11. Method of allelic replacement using pMAD.

For gene cloning and allelic replacement, genes to be cloned are identified from publicly available databases or are independently identified, then isolated by polymerase chain reaction (PCR) and the products gel-purified and redissolved in Tris/EDTA (TE) buffer. They are then cloned to a shuttle vector in E. coli and used for further constructions. Modifications of the basic SaPI2 genome have been made using an allelic replacement scheme that makes use of a plasmid known as pMAD (Arnaud, et al., App. Env. Microbiol. 70:6887 (2004), commercially available from Addgene) which is outlined in FIG. 11. In the illustration, the relevant region of SaPI2 containing the tst and eta genes, shown in yellow, are replaced by the tetracycline resistance (TcR) gene, tetM, shown in dark blue. To perform such a replacement, PCR is used to prepare a ~1 kb segment from each side of the gene region to be replaced, including at the ends of each of the two segments restriction enzyme sites that match those in the multicloning site (MCS) of the pMAD plasmid. These flanking sequences (FR & FL) are then cloned to pMAD followed by cloning between them the gene (tetM) that is to replace the SaPI2 tst and eta genes. pMAD has a thermosensitive replicon so that when introduced into the organism where the replacement is to be made, and required to grow and express its erythromycin resistance (EmR) at the restrictive temperature (42° C.), it can survive only by undergoing a recombinational event (crossover) involving either of the flanking sequences. This results in the insertion of the entire plasmid along with tetM, FR and FL. The resulting colonies will be not only EmR but also blue on an X-gal plate owing to the expression of the plasmid-carried β-galactosidase gene The configuration with the integrated plasmid, shown in FIG. 11B is genetically unstable owing to the duplicated flanking sequences (FR and FL), and can undergo a second recombinational crossover. This can involve either the green FR segments (red dotted line), or the blue FL segments (solid black line). The former will simply restore the original configuration, whereas the latter will substitute tetM for the tst/eta region. When the resulting culture is plated on tetracycline-containing medium at the restrictive temperature, only bacteria containing tetM in place of the tst/eta region will be able to grow and these will be white on X-gal, having lost the entire pMAD plasmid, with its β-galactosidase gene.

This approach has been used for SaPI2 modifications disclosed herein and can be adapted for all modifications that are contemplated by this disclosure. In some cases, a new gene can be inserted at a specific site in SaPI2 but will not replace any resident gene. In such instances, the 1 kb region on either side of the target site will be cloned to pMAD adjacent to one another, but separated by a restriction site into which will secondarily be cloned the gene to be inserted.

Studies with mice described herein revealed that an IP dose of $10^{11}$ of the SaPI2 particles containing the CRISPR/dCas9 construct had no visible ill effects, nor did a similar dose of the SaPI2 particles containing the hla gene, which encodes α-hemolysin, a toxin with μg lethality. Mice were observed for 7 days following the SaPI injections. In order to avoid the presence of an antibiotic resistance gene (tetM) in the SaPI2 derivatives, we plan to prepare derivatives similar to those shown in FIG. 4 in which an arsenate resistance cassette has replaced tetM.

Figure 4:
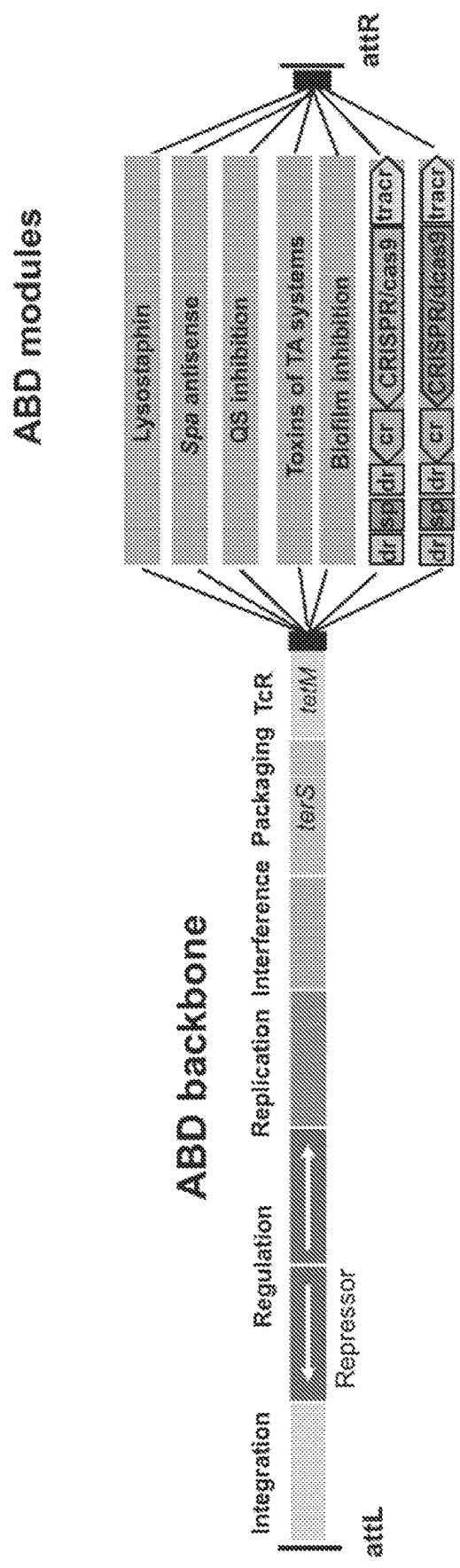
FIG. 4. ABD constructs. From attL to tetM is the ABD backbone. Black boxes represent the cloning site. Gray rectangles between cloning sites represent different modules that have been or will be added to the backbone. dr: direct repeat; sp: spacer; cr: crRNA leader; tracr: tracr RNA.
Figure 13:
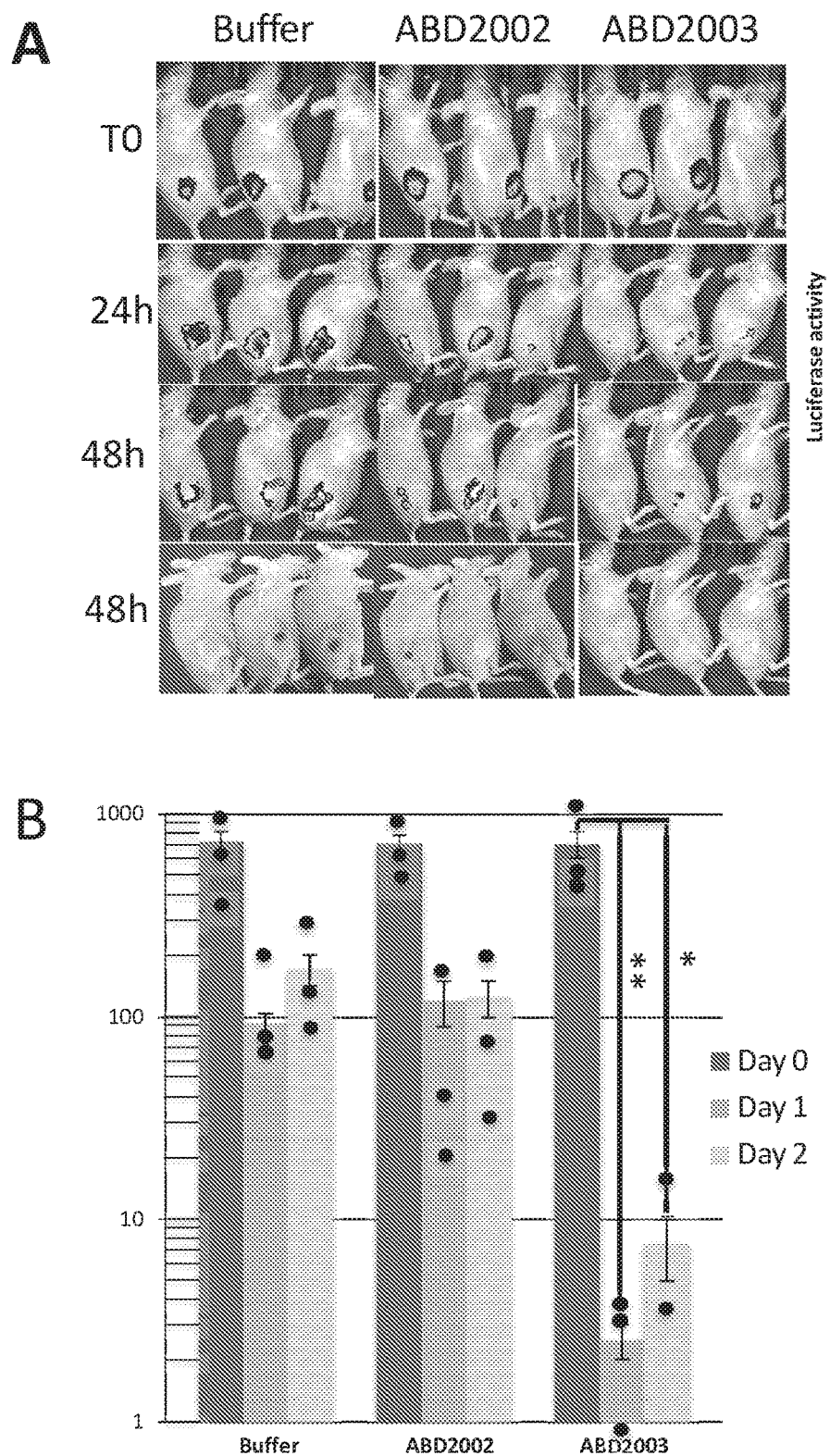
FIG. 13. Blockage of subcutaneous (SC) abscess formation by ABD2003 (SaPI2 containing CRISPR/cas9 with an agrA spacer). Bacteria, 4×10$^8$, were injected into the SC space of hairless mice through a 27-gauge teflon cannula, followed by 1.2×10$^9$ ABD2002 or 2003 particles, through the same cannula. Bacteria were imaged in the in vivo imaging system (IVIS) immediately and after 24 and 48 h. In panel (A) is shown the IVIS images for luciferase activity (Top 3 rows) and photographs of the abscesses of the same mice (bottom row). In panel (B) is shown a quantitative analysis of the luciferase signals. Error bars represent standard errors. **P=0.01; *P=0.05, determined by the one-tailed Fisher's exact test. Luciferase signals were quantitated using Living Image software (Perkin-Elmer, Inc.).
Figure 14:
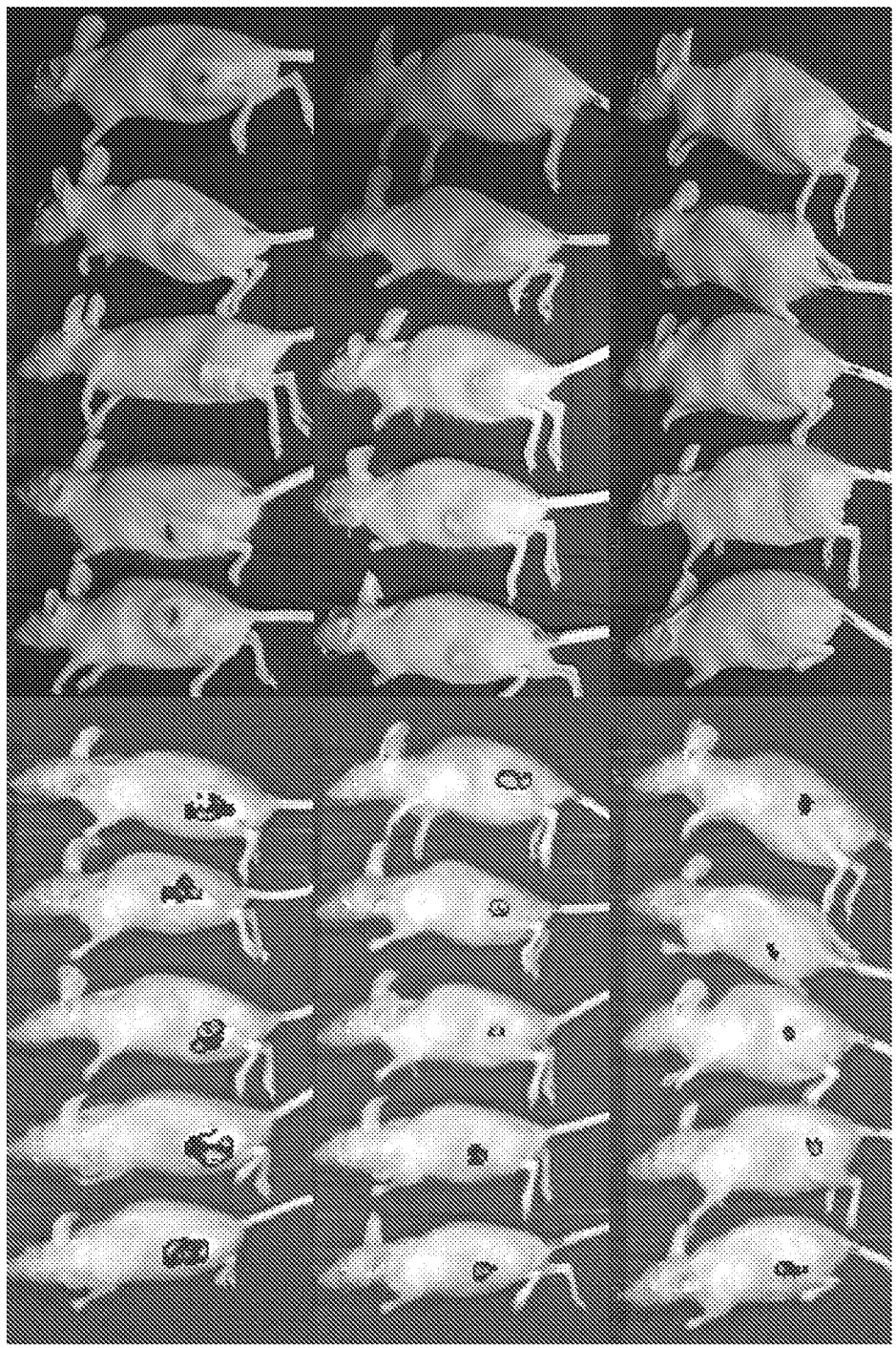
FIG. 14. Blockage of abscess formation by an agr-inhibiting ABD. Hairless mice were infected with $4 \times 10^8$ RN1 cells, in 50 µl PBS, through a teflon cannula, followed immediately by $4 \times 10^9$ ABD particles in 50 µl PBS, either ABD2005 (non-targeting) or ABD2006 (targeting the $agrP_2P_3$ promoter region), as indicated. Mice were imaged in the IVIS immediately and after 18 and 42 h. The 42h images are shown.
Figure 15:
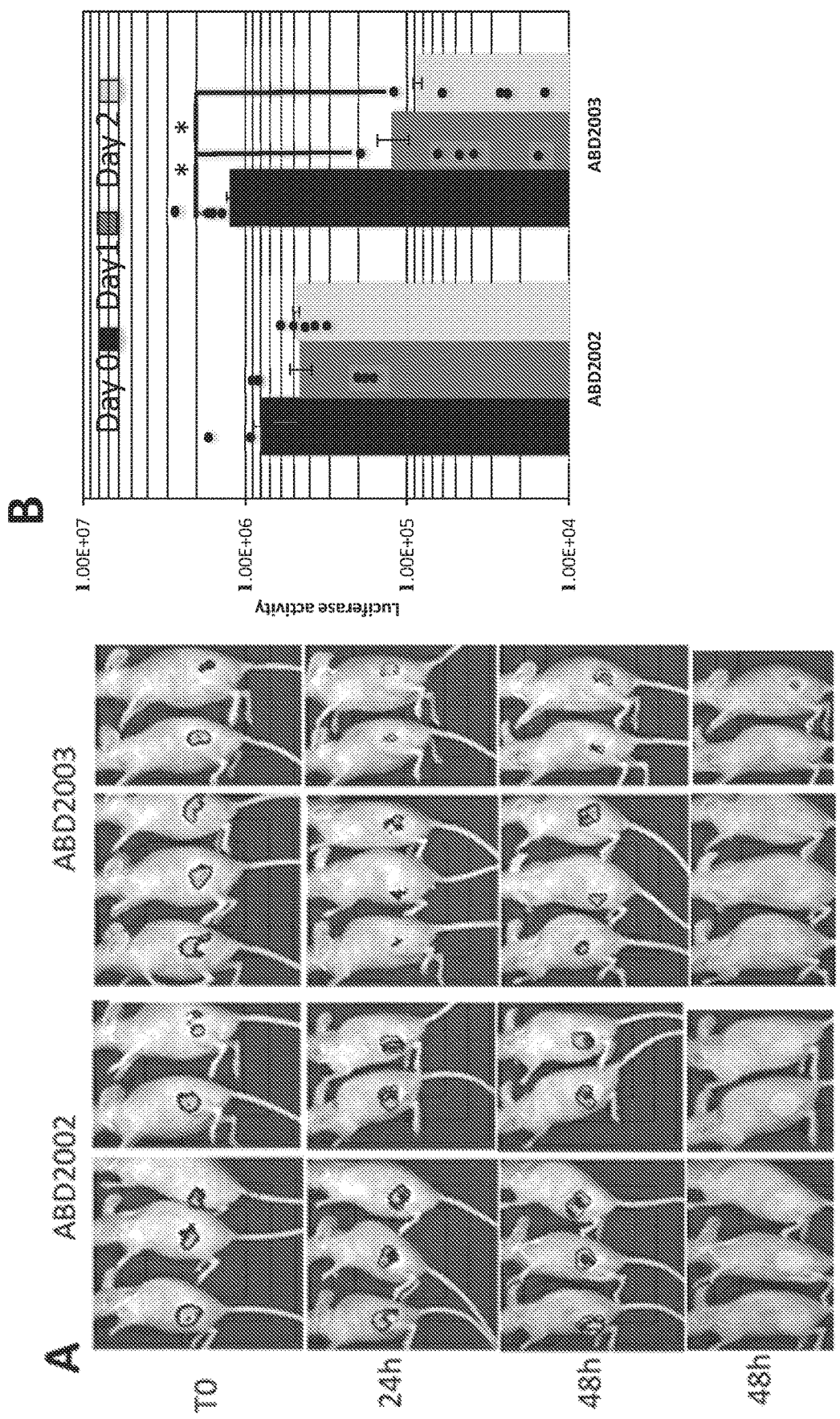
FIG. 15. Treatment of an SC murine abscess by IP administration of ABD particles. Mice were injected SC with $4 \times 10^8$ organisms, strain RN1 containing an $agrP_3$::lux fusion, followed immediately by $8.8 \times 10^9$ ABD particles IP. IP treatment with ABD particles at the same dose was repeated 1h later. Mice were imaged in the IVIS immediately after the first ABD injection, and again after 24 and 48 h. Panel A—IVIS images and abscess photographs; panel B—quantitative analysis of luciferase signals. Each bar represents the average of the luciferase signals for the five mice in each group at the three time points shown. Error bars represent standard deviations. Significance was evaluated by the one-tailed Fisher's exact test; *P=0.05. Abscesses at 48 h are the prominent white areas in the mouse flanks—present in all 5 of the ABD2002 mice but in only one of the ABD2003 mice. The difference in abscess formation is significant at the 5% level, using a one-tailed Fisher's exact test.
Figure 16:
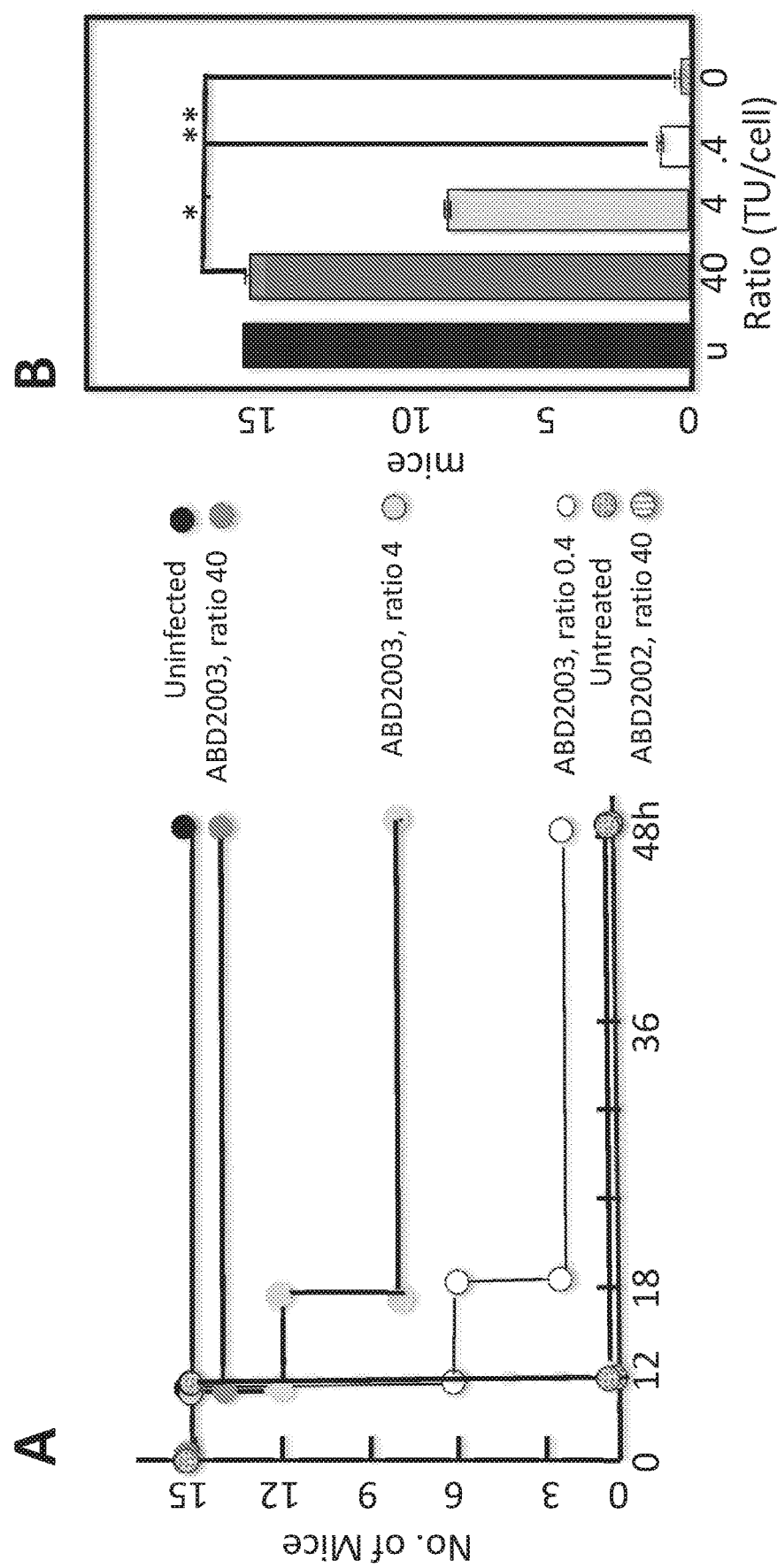
FIG. 16. Rescue by ABD2003 of mice given a lethal IP dose of staphylococci. Groups of 5 mice were infected IP with $5 \times 10^9$ cells (in 50 µl PBS) of RN1. This was followed immediately by IP injection of different numbers of ABD2003 particles in 250 µl PBS. Mice were monitored for 48h. In panel (A) is shown the time course of mouse deaths; In panel (B) is a graphical representation of the final results, in which the groups of mice were pooled and statistics calculated on the pooled groups. Error bars represent standard deviations for each set of 3 pools; *P=0.01; **P=0.004, calculated by the one-tailed Fisher's exact test.

We have demonstrated that the constructs illustrated in FIG. 4 and Table 3 (ABD2003 and ABD2006) with a CRISPR/Cas9 spacer targeting agrA or CRISPR/dCas9 with a spacer targeting agrP$_2$P$_3$, either kills a *staphylococcus* or blocks its expression of agr, respectively, in vitro (FIGS. 7 & 8); we have also demonstrated that ABD2009, in which the lysostaphin gene has been cloned to the basic SaPI2 backbone, kills staphylococci by lysis (FIG. 12); either ABD2003 or ABD2006 prevents the development of a murine staphylococcal subcutaneous abscess when injected immediately after inoculation of the subcutaneous tissue with a virulent *staphylococcus* (FIGS. 13 & 14), or when injected intraperitoneally (FIG. 15). Additionally, the CRISPR/cas9/agrA construct rescues mice given a lethal IP dose of staphylococci (FIG. 16). In these tests, the infecting bacteria are tagged with a luciferase gene that generates a light signal that is imaged with an in vivo imaging system (IVIS) (Perkin-Elmer) camera. Thus, the disclosure provides demonstrations of both prophylaxis and therapy using representative ABDs that were made and used according to the instant description. The skilled artisan will accordingly be able to adapt these demonstrations to make and use any embodiment of the invention that is described herein, given the benefit of the present disclosure.

While the disclosure has been particularly shown and described with reference to specific embodiments, it should be understood by those having skill in the art that various changes in form and detail may be made therein without departing from the spirit and scope of the present disclosure as disclosed herein.

What is claimed is:

1. A polynucleotide comprising a staphylococcal bacterial pathogenicity island nucleotide sequence (B-PINS) comprising modifications (a modified B-PINS), wherein the modifications comprise: i) a deletion or disruption of all virulence determinants of the B-PINS; ii) an insertion of at least one cargo sequence into the modified B-PINS, said cargo sequence comprising a sequence encoding a toxin that kills bacteria; and iii) and a deletion of staphylococcal capsid morphogenesis cpmA and cpmB genes, wherein the polynucleotide comprising the modified B-PINS is capable of being packaged within a bacterium into a phage-like particle that comprises bacteriophage capsid, tail and tail fiber proteins, and wherein the phage-like particle containing the modified B-PINS (an antibacterial drone "ABD") is capable of infecting bacteria such that the at least one cargo sequence is introduced into bacteria infected by the ABD, and wherein said cargo sequence is expressed within and kill the bacteria infected by the ABD but does not kill bacteria that produce the modified ABD.

2. The polynucleotide of claim 1 further comprising at least one additional cargo sequence that comprises a polynucleotide sequence encoding a bactericidal agent that is functional against a target in the bacteria infected by the ABD.

3. The polynucleotide of claim 2, wherein the bactericidal agent comprises one or a combination of: a) a sequence encoding an RNA that comprises specificity for the target, wherein the target comprises an essential gene or an RNA encoded by an essential gene b) a sequence encoding a protein that has specificity for the target and/or can participate in and/or cause its cleavage and/or inactivation.

4. The polynucleotide of claim 3, wherein a) comprises an anti-sense RNA.

5. The polynucleotide of claim 3, wherein a) comprises a Clustered Regularly Interspaced Short Palindromic repeats (CRISPR) guide RNA targeted to a sequence in the bacteria in the bacterial population.

6. The polynucleotide of claim 3, wherein the encoded protein of b) comprises a CRISPR-associated nuclease that is a Cas9 nuclease, a Cpf1 nuclease, or a dCas9.

7. The polynucleotide of claim 1, wherein the toxin comprises lysostaphin.

8. The polynucleotide of claim 1, wherein the toxin is secreted by the bacteria and is bactericidal against the bacteria and bacteria that are uninfected by the ADB.

9. The polynucleotide of claim 3, wherein the target is comprised by a bacterial chromosome or a bacterial plasmid.

10. The polynucleotide of claim 3, wherein the target confers antibiotic resistance.

11. An ABD of claim 1, wherein the ABD is present in a pharmaceutical composition.

12. A method comprising administering a pharmaceutical or other composition comprising ABDs of claim 11 to an individual in need thereof, wherein subsequent to the administration bacteria in the individual are killed or exhibit reduced virulence.

13. The method of claim 12, wherein the ABD comprises a sequence encoding a toxin that is cytostatic against bacteria, wherein the toxin is optionally lysostaphin.

14. A bacterial population comprising ABDs of claim 11.

15. The polynucleotide of claim 3, wherein the sequence encoding the protein of b) encodes a restriction enzyme.

* * * * *